United States Patent [19]
Bachi et al.

[11] Patent Number: 6,166,065
[45] Date of Patent: Dec. 26, 2000

[54] 2,3-DIOXABICYCLO[3.3.1]NONANE DERIVATIVES AND ANTIMALARIAL PHARMACEUTICAL COMPOSITIONS COMPRISING THEM

[75] Inventors: Mario Bachi, Rehovot, Israel; Gary H. Posner, Baltimore, Md.; Edward Korshin, Rehovot, Israel

[73] Assignees: Yeda Research and Development Co., Ltd., Rehovot, Israel; Johns Hopkins University, Baltimore, Md.

[21] Appl. No.: 09/508,428

[22] PCT Filed: Sep. 10, 1998

[86] PCT No.: PCT/IL98/00440

§ 371 Date: May 11, 2000

§ 102(e) Date: May 11, 2000

[87] PCT Pub. No.: WO99/12900

PCT Pub. Date: Mar. 18, 1999

[30] Foreign Application Priority Data

Sep. 11, 1997 [IL] Israel .......................................... 121749

[51] Int. Cl.[7] ........................ A61K 31/335; C07D 319/02
[52] U.S. Cl. ............................ 514/452; 549/360; 549/363
[58] Field of Search .................... 549/363, 360; 514/452

[56] References Cited

FOREIGN PATENT DOCUMENTS 0 311 955  4/1989  European Pat. Off. .

OTHER PUBLICATIONS

Xu et al., "Total Synthesis of (+)–Yingzhaosu A," Tetrahedron Letters, vol. 32, No. 41, pp. 5785–5788, 1991.
Jacquet et a, "Antimalarial activity of the bicyclic peroxide Ro 42–1611 (arteflene) in experimental models," Trop. Med. Parasitol, 45, (1994), 266–271.
Hofheinz et al., "Ro 42–1611 (arteflene), a new effective antimalarial: chemical structure and biological activity," Trop. Med. Parasitol, 45, 1994), 261–265.

*Primary Examiner*—Bernard Dentz
*Attorney, Agent, or Firm*—Browdy and Neimark

[57] ABSTRACT

2,3-Dioxabicyclo[3.3.1]nonane derivatives, carrying, at position 4, a sulfur-containing functionality selected from the group consisting of sulfonyl, sulfinyl and sulfenyl, adhered to C(4) vie methylene group, represented by structural formula (A) wherein: X is hydrogen, hydroxy, alkoxy, optionally substituted by alkoxy or acyloxy, aralkoxy optionally substituted by alkoxy or aryloxy, and M is hydrogen, hydroxy, alkoxy, alkenyloxy, acyloxy, optionally substituted by acyl or acyloxy, aralokoxy, arylalkenyloxy, oxalyloxy substituted by alkoxy, di(alkyl)amino or alkyl(aryl)amino, di(aralalkyl)amino or carbonyloxy substituted by arloxy, di(alkyl)amino, di(aralkyl)amino and alkyl(aryl) amino; or X and M together represent a carbon-carbon bond or an oxygen atom; L is hydrogen or L and M together represent a carbon-carbon bond; and either Z is a radical R—S(=O)$_n$— and Y is hydrogen, or Y is R—S(=O)$_n$— and Z is hydrogen, wherein R is alkyl optionally substituted by alkoxy or alkoxycarbonyl, cycloalkyl, or aryl or araklkyl optionally substituted by alkyl, halogen or CF$_3$; and n is 0, 1, or 2, are useful for the prevention and/or treatment of malaria.

12 Claims, No Drawings

2,3-DIOXABICYCLO[3.3.1]NONANE DERIVATIVES AND ANTIMALARIAL PHARMACEUTICAL COMPOSITIONS COMPRISING THEM

CROSS REFERENCE TO RELATED APPLICATION

The present application is the national stage under 35 U.S.C. 371 of PCT/IL98/00440, filed Sep. 10, 1998.

The invention described and claimed herein was made in part under a grant from the National Institutes of Health, NIH-AI-34885. The U.S. Government has certain rights in the invention.

FIELD OF THE INVENTION

The present invention is in the field of antiparasitic drugs and particularly relates to novel antimalarial 2,3-dioxabicyclo[3.3.1]nonane compounds.

BACKGROUND OF THE INVENTION

Malaria is the world's most widespread infectious disease. More than 300 million people are infected, and about 2 million die of it each year.[1] Curing malaria by treatment with alkaloids like quinine and chloroquine is becoming less effective due to the continuous emergence of malaria parasites resistant to these drugs.

A new approach to malaria chemotherapy, which is raising high expectations, is based on the use of cyclic peroxides.[2] Indeed, artemisinin, an endoperoxide sesquiterpene, was introduced in China as a drug in 1987.[3] In Western countries several compounds structurally related to artemisinin were clinically tested, but due to pharmacokinetic drawbacks and incomplete toxicological profiles, none of them were approved as a drug. Cyclic peroxide yingzhaosu A was isolated from a Chinese folk medicine, but no significant physiological and pharmacological data have so far been reported.[4]

Recently, scientists at Hoffmann-La Roche reported on the synthesis, antimalarial screening and clinical trials of 7-oxo-2,3-dioxabicyclo[3.3.1]nonanes, bearing at C(4) alkyl- or alkenyl substituents.[5–7] In vitro and in vivo antimalarial screening, as well as clinical trials of arteflene, the most active compound in this series, gave encouraging results.

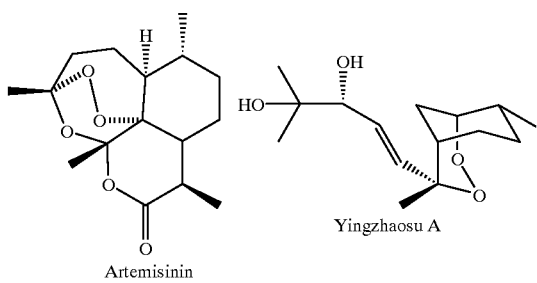

Artemisinin

Yingzhaosu A

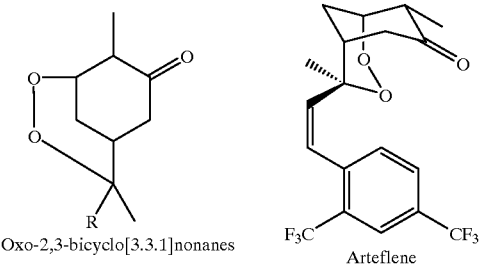

7-Oxo-2,3-bicyclo[3.3.1]nonanes

Arteflene

Biological evaluation of a variety of cyclic peroxides indicates that a number of them are effective non-toxic antiparasitic agents. However, parasitic infections, particularly malaria, remain a serious and widespread public health problem, and concern exists about possible side-effects of compounds developed to date. For example, neurotoxicity has been seen in rats which were administered high doses of artemether, and in mouse neuroblastoma cells treated with dihydroarte-mesinin.[8]

It would be highly desirable to develop improved therapeutic agents for prevention and treatment of malaria.

SUMMARY OF THE INVENTION

The object of the present invention is to provide novel compounds for the treatment of parasitic infections, particularly malaria.

To accomplish this goal, the present invention provides 2,3-dioxabicyclo[3.3.1]nonane derivatives, carrying, at position 4, a sulfur-containing functionality selected from the group consisting of sulfonyl, sulfinyl and sulfenyl, adhered to C(4) via methylene group, represented by general structural formula A.

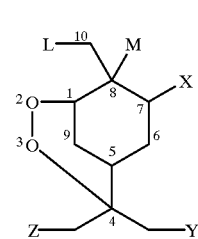

A wherein:

X is hydrogen; hydroxy; alkyloxy, optionally substituted by alkoxy or acyloxy; aralkoxy or acyloxy optionally substituted by alkoxy or aryloxy; and M is hydrogen; hydroxy; alkoxy; alkenyloxy; acyloxy optionally substituted by acyl or acyloxy; aralkoxy; arylalkenyloxy; oxalyloxy substituted by alkoxy, di(alkyl)amino or alkyl(aryl)amino; di(aralalkyl)amino or carbonyloxy substituted by aryloxy, di(alkyl)amino, di(aralkyl)amino and alkyl(aryl)amino; or X and M together represent a carbon-carbon bond or an oxygen atom;

L is hydrogen or L and M together represent a carbon-carbon bond; and either Z is a radical R—S(=O)$_n$— and Y is hydrogen, or Y is R—S(=O)$_n$— and Z is hydrogen, wherein R is alkyl optionally substituted by alkoxy or alkoxycarbonyl; cycloalkyl; or aryl or aralkyl optionally substituted by alkyl, halogen or CF$_3$; and n is 0, 1 or 2.

The term "alkyl" as used herein for R stands for a straight or branched C1–C20, preferably C4–C14, alkyl radical such as, but not being limited to, n-butyl, tert-butyl, 3-octyl, and n-dodecyl, and "substituted alkyl" includes radicals such as octyloxyethyl and ethoxycarbonylmethyl.

The term "cycloalkyl" as used herein for R stands for a C$_5$–C$_7$ cycloalkyl, preferably cyclohexyl.

The term "aryl" as used herein for R stands for a C6–C12 aryl, optionally mono or disubstituted by C1–C12 alkyl, halogen such as chloro and fluoro, or CF$_3$ such as, but not being limited to phenyl, biphenyl, naphthyl, 4-methylphenyl, 2,4-dimethylphenyl, 4-fluorophenyl, 2,4-dichlorophenyl, 2,4-difluorophenyl, 4-trifluoromethylphenyl, 2,4-[di(trifluoromethyl)]phenyl and 3,5-[di(trifluoromethyl)]phenyl.

The term "arylkyl" as used herein for R stands for a C7–C25, preferably C7–C19, radical optionally substituted by alkyl, halogen such as chloro and fluoro, or CF$_3$ such as, but not being limited to benzyl, 4-phenylbutyl, 4-(trifluoromethyl)-benzyl and (triphenyl)methyl.

The term "alkoxy" as used herein for X and M stands for a C1–C20, preferably C1–C14, alkoxy radical. With regard to X, the alkoxy group may be substituted by alkoxy or acyloxy, and examples are, but not being limited to, methoxy, hexyloxy, dodecyloxy, butoxyethoxy, (hexanoyloxy)ethoxy, and phenethyloxy. With regard to M, examples of alkoxy are methoxy, octyloxy.

The terms "acyl" and "alcyloxy" as used herein for X and M refer to C2–C20, preferably C2–C14, carboxylic acyl derived from a straight or branched, saturated or unsaturated aliphatic carbonylic acid or from an aromatic carboxylic acid. Examples of acyloxy radicals for X are, without being limited to, acetyloxy, benzoyloxy, biphenyl-4-carboxyloxy, di(phenyl)acetyloxy, butanoyloxy, octanoyloxy, dodecanoyloxy, methoxyacetyloxy, phenoxyacetyloxy. Examples of acyl and acyloxy radicals for M are, without being limited to, acetyloxy, acetylacetyloxy, 3-(acetyloxy)-but-2-enoyloxy.

The term "alkenyloxy" as used herein for M stands for a C3–C20, preferably C3–C14, alkenyloxy radical such as, but not being limited to, allyloxy, 3(methyl)but-2-enyloxy, cinnamyloxy.

Examples of substituted oxayloxy and carbonyloxy radicals for M are, without being limited to, ethoxyoxalyloxy, (methyl)-phenylaminooxalyloxy, di(benzyl)-aminooxalyloxy, phenoxycarbonyloxy.

When L and M together represent a carbon-carbon bond, this means that an alkenyl residue H$_2$C=is linked to the ring carbon at position 8, and when X and M together represent a carbon-carbon bond, this means that there is a double bond between the carbon atoms at positions 7 and 8 of the ring.

When X and M represent one oxygen atom, this means that they, together with the ring carbon atoms at positions 7 and 8, form an oxirane ring.

When n is 0, 1 or 2, the compounds are sulfides, sulfoxides and sulfones, respectively, and the sulfur-tethered appendages are, for example, without being limited to, alkylthio, cycloalkylthio, arylthio, aralkylthio, alkylsulfinyl, cycloalkylsulfinyl, arylsulfinyl, aralkylsulfinyl, alkylsulfonyl, arylsulfonyl, aralkylsulfonyl and substituted radicals as defined above for R.

The central molecular framework of the compounds of the invention consists of two cis-bridged 6-membered rings containing 4 or 5 stereogenic centers. The invention relates preferentially to compounds A represented by either three dimensional compounds of structure I characterized by stereogenic centers (1R, 5R) and compounds of structure II characterized by stereogenic centers (1S, 5S).

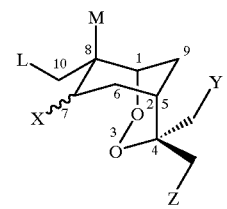

I

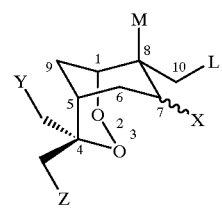

II

In I and II, either Y represents a sulfur-tethered appendage and Z represents hydrogen; or Z represents a sulfur-tethered appendage and Y represents hydrogen.

Structure I is subdivided into structures Ia and Ib, and structure II is subdivided into structures IIa and IIb.

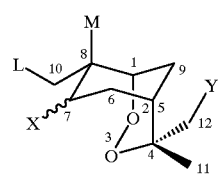

Ia

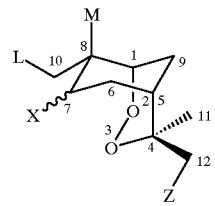

Ib

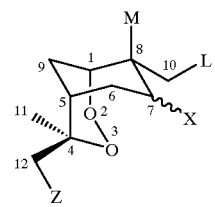

IIb

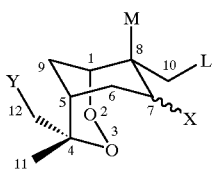

IIa

Throughout the specification C-4 epimers are given the same Arabic number and are differentiated by a and b. In sulfoxides, where there is an additional stereogenic center on the sulfur atom, epimers on sulfur are differentiated by 'e.g., a and a'.

The invention further relates to pharmaceutical compositions for the treatment of malaria comprising a compound of formula A and a pharmaceutically acceptable carrier.

In another embodiment, the invention relates to a method of treating malaria comprising administering to a patient afflicted with malaria an effective amount of a compound of formula A.

DETAILED DESCRIPTION OF THE INVENTION

| Abbreviations | |
|---|---|
| Ac | acetyl |
| Bn | benzyl |
| br. | broad (in NMR spectroscopy) |
| Bz | benzoyl |
| CI | chemical ionization (in mass-spectroscopy) |
| DBPO | di-tert-butyl peroxalate |
| DCI | desorption chemical ionization (in mass-spectroscopy) |
| DMAP | (4-dimethylamino)pyridine |
| DP | direct phase (in chromatography) |
| HPLC | high-performance liquid chromatography |
| HRMS | high-resolution mass spectrum |
| MCPBA | m-chloroperoxybenzoic acid |
| MPLC | medium-pressure liquid chromatography |
| $R_f$ | retention factor (in chromatography) |
| RP | reverse phase (in chromatography) |
| rt | room temperature |
| Tf | trifluoromethanesulfonyl (triflyl) |
| TLC | thin layer chromatography |
| TMS | trimethylsilyl |
| TOCO | thiol-oxygen cooxidation |
| v.s. | very strong (in IR-spectroscopy) |
| $\tau_R$ | retention time (in HPLC) |

The methodology applied for the synthesis of the novel antimalarial 2,3-dioxabicyclo[3.3.1]nonanes of type A involves one or more of the following processes:

(1) Submission of monoterpenes like R-(+)-limonene 1, S-(−)-limonene) 1' and carveol derivatives 3 to thiol oxygen cooxidation reactions (TOCO reactions), followed by treatment with a reducing agent, such as triphenylphosphine. This process is suitable for the preparation of compounds of type A (R represents an alkyl-, aralkyl- or aryl group, M represents hydroxyl, n=0) as described in General Procedure 1.

(2) Oxidation of the sulfide group in compounds of type A (R represents an alkyl, aralkyl- or aryl group, n=0) to the corresponding sulfones of type A (R represent an alkyl-, aralkyl- or aryl group, n=2) as described in General Procedure 2.

(3) Oxidation of the sulfide group in compounds A (R represents an alkyl-, aralkyl- or aryl group; n=0) to sulfoxides of type A (R represents an alkyl-, aralkyl- or aryl group; n=1), as described in General Procedure 3.

(4) Manipulations of functional groups in compounds of type A (R represents an alkyl-, aralkyl- or aryl group, n=0 or n=2) as described in General Procedures 4–8.

1

1'

3

General Procedure 1

Synthesis of 2,3-dioxabicyclo[3.3.1]nonane-8-ols A (R represents alkyl, aralkyl- and aryl; n=0; M=OH). Through a stirred solution of monoterpene (1,1' or 3) (ca. 3 equivalents, 0.02–0.10 M) and di-tert-butyl peroxalate (DBPO) (0.02–0.04 equivalents) in n-heptane -benzene mixture (ca. 2:1) oxygen gas is gently bubbled with simultaneous addition of a solution of thiol (1 equivalent) in benzene or heptane (5–20 mL) over a period 12 h (syringe pump). After the addition of thiol is completed the mixture is kept under oxygen for additional 12–14 h. It is then diluted with $CH_2Cl_2$, cooled to 0–5° C. and powdered $Ph_3P$ (1 equivalent) is added. The mixture is stirred for an additional 2 h at 0–5° C. and for 1 h at rt, solvents are evaporated at rt Flash chromatography affords the title compounds, which can be used for the preparation of additional antimalarial agents of type A as described in General Procedures 2–7.

General procedure 2

Preparation of sulfones A (n=2). A solution of a sulfide A (R represents alkyl, aralkyl or aryl; n=0) (1 equivalent, ca. 0.2 M) and MCPBA (ca. 2.2–2.5 equivalents) in EtOAc is stirred at rt for 4–10 h. After consumption of the intermediate sulfoxide (TLC monitoring) the mixture is poured into a saturated solution of $NaHCO_3$, extracted with an organic solvent, dried ($Na_2SO_4$ and $NaHCO_3$) and evaporated. Chromatography of the residue affords the title compounds.

General procedure 3

Preparation of sulfoxides A (n=1). To a solution of a sulfide A (R represents alkyl, aralkyl or aryl; n=0) (1 equivalent, ca. 0.05 M) in EtOAc at −30÷−50° C., a solution of MCPBA (ca. 1.05 equivalents, ca. 0.06 M solution) in EtOAc is added and the mixture is stirred at −30÷−40° C. until the starting material is consumed (monitoring by TLC). The mixture is poured into a saturated solution of $NaHCO_3$, extracted with an organic solvent, dried ($Na_2SO_4$ and $NaHCO_3$) and evaporated. Chromatography of the residue affords the title compounds.

General procedure 4

Synthesis of 2,3-dioxabicyclo[3.3.1]non-7-enes A (M and X together represent a carbon-carbon bond; n=0 or n=2) and 8-methylene-2,3-dioxabicyclo[3.3.1]nonanes A (L and M together represent a carbon-carbon bond; n=0 or n=2). To a mixture of $SOCl_2$ (ca. 4 equivalents) and pyridine (10 equivalents) in dry $CH_2Cl_2$ (ca. 40 mL/mmol substrate) at −30—40° C. is added during 1.5 h, a solution of a 2,3-dioxabicyclo[3.3.1]nonan-8-ol A (M=OH, X=H, n=0 or n=2) (1 equivalent, ca. 1 mmol/10 mL) in $CH_2Cl_2$. The temperature is raised to 25° C. and after stirring for 5 h, the reaction mixture is poured into ice-cold 0.1 M HCl (ca. 25 mL/mmol of substrate), extracted with hexane/EtOAc, washed with saturated $NaHCO_3$, dried ($Na_2SO_4+NaHCO_3$) and evaporated. Chromatography of the residue affords a mixture of the two title compounds.

General procedure 5

Synthesis of 2,3-dioxabicyclo[3.3.1]nonanes A (M represents a hydrogen atom; n=0 or n=2). To a mixture of a 2,3-dioxabicyclo[3.3.1]non-7-enes of type A (M and X together represent a carbon-carbon bond; n=0 or n=2) and/or 8-methylene-2,3-dioxabicyclo[3.3.1]nonanes A (L and M together represent a carbon-carbon bond; n=0 or n=2) (1 equivalent, ca. 0.01 M solution), and potassium azodicarboxylate (10–15 equivalents) in MeOH/CH$_2$Cl$_2$ at 0° C. is added during ca. 1 h, a solution of AcOH (20–30 equivalents) in CH$_2$Cl$_2$. The mixture is stirred for 2 days at rt, diluted with ether, filtered through Celite® and evaporated. Chromatography of the residue affords the title compounds.

General procedure 6

Synthesis of 8-acyloxy-2,3-dioxabicyclo[3.3.1]nonanes A (M represents an acyloxy function; n=0 or n=2). To a solution of a 2,3-dioxabicyclo[3.3.1]nonan-8-ol A (M represents a hydroxyl group, n=0 or n=2) (1 equivalent, ca. 0.5 M solution) and 2,6-lutidine (ca. 3 equivalents) in CH$_2$Cl$_2$ at 0° C. is added TMSOTf (ca. 2 equivalent). The mixture is stirred for 30 min at 0° C. and then at rt until the starting material is consumed. The reaction mixture is poured into cold water, extracted with an organic solvent, dried (Na$_2$SO$_4$+NaHCO$_3$) and evaporated to give A (M represents the OTMS group; n=0 or n=2) in practically quantitative yield. A mixture of the crude TMS-derivative (1 equivalent), acyl chloride (5–8 equivalents) and oven-dried CsF (3–5 equivalents) in acetonitrile (ca. 10 mL/mmol) is stirred for 5–10 days at rt The mixture is poured into a saturated NaHCO$_3$ solution, extracted with organic solvent, dried (Na$_2$SO$_4$+NaHCO$_3$) and evaporated. Chromatography of the residue affords the title compounds.

General procedure 7

Synthesis of 8-alkoxy-2,3-dioxabicyclo[3.3.1]nonanes A (M represents an aralkoxy or alkenyloxy function; n=2). To a suspension of a 2,3-dioxabicyclo[3.3.1]nonan-8-ol of type A (M represents a hydroxyl group; n=2) (1 equivalent, ca. 0.3 M solution) in dry ether, at 0° C. is added a concentrated solution of CCl$_3$C(=NH)OR (R represents an alkenyl or an (aryl)alkyl group) (3–4 equivalents) in CH$_2$Cl$_2$. Following formation of a homogeneous mixture, a solution of TfOH (ca. 0.03 equivalents, ca. 0.1 M) in dry ether is added. The reaction mixture is stirred for ca. 5 h at 0° C. Addition of solutions of trichloroacetimidate and TfOH is repeated until the starting hydroxysulfone is consumed. The mixture is then diluted with an organic solvent, excess of (Na$_2$SO$_4$+NaHCO$_3$) is added and the mixture is stirred overnight. Concentration in vacuo, followed by chromatography affords the title compounds.

General procedure 8

Synthesis of 7,8-epoxy-2,3-dioxabicyclo[3.3.1]nonanes A (M and X together represent an oxygen atom; n=2). A mixture of a 2,3-dioxabicyclo[3.3.1]non-7-ene A (M and X together represent a carbon-carbon bond; n=2) (1 equivalent, ca. 0.05 M solution) and MCPBA (ca. 1.1 equivalents) in CH$_2$Cl$_2$ is stirred at rt for 12 h, diluted with hexane/EtOAc, washed with saturated NaHCO$_3$, dried (Na$_2$SO$_4$+NaHCO$_3$) and evaporated. Chromatography of the residue affords the title compounds.

EXAMPLES

The compounds in the following Examples were prepared according to Schemes 1–15, presented hereinafter.

Scheme 1

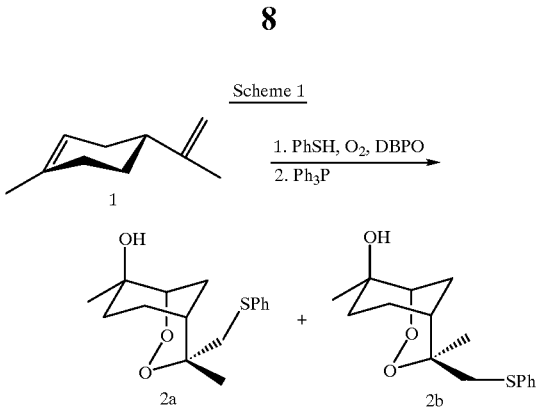

Scheme 2

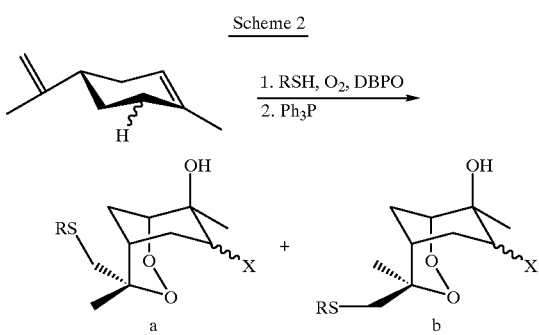

1', X = H;  2'a,b, X = H, R = Ph;
3a, X = β-OBz;  4a,b, X = β-OBz, R = Ph;
3a, X = β-OBz;  5a,b, X = β-OBz, R = n-Bu;
3b, X = α-OBz;  6a,b, X = α-OBz, R = Ph;
3c, X = α-OH;  7a, X = α-OH, R = Ph;

Scheme 3

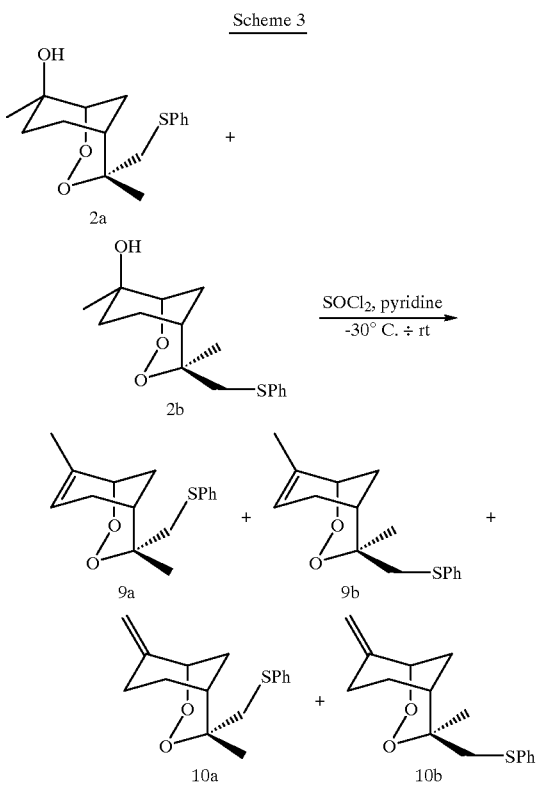

Scheme 4
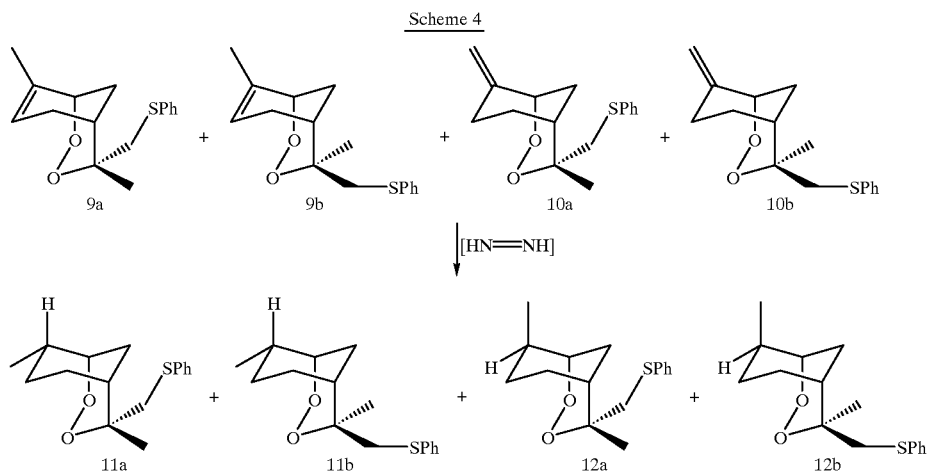
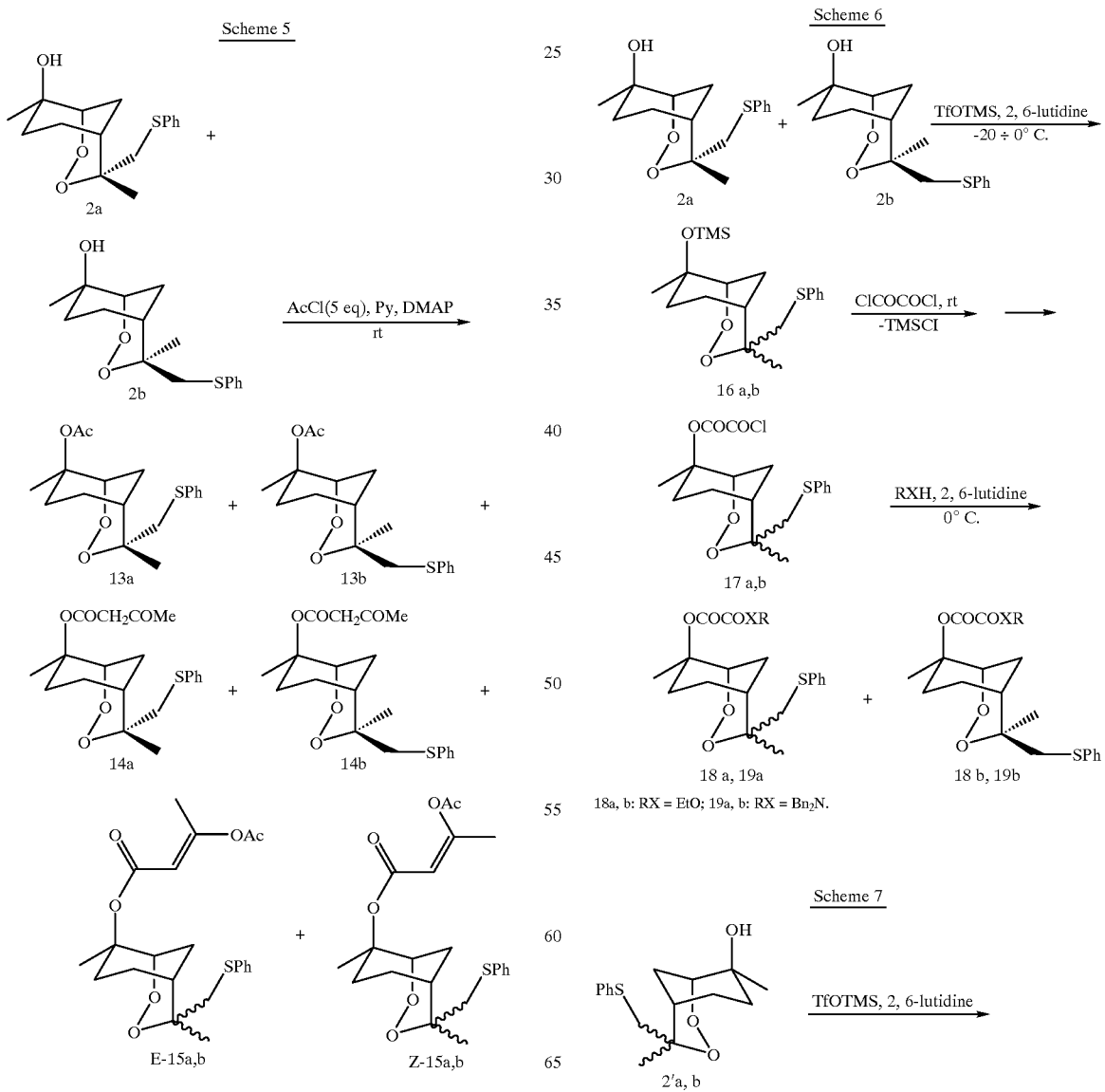

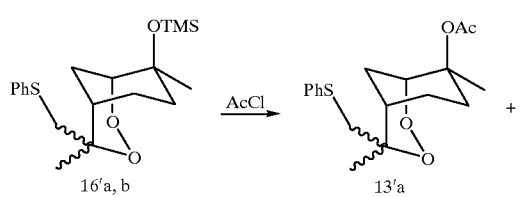

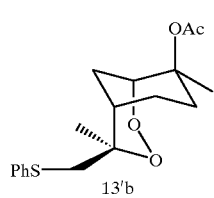

Scheme 8

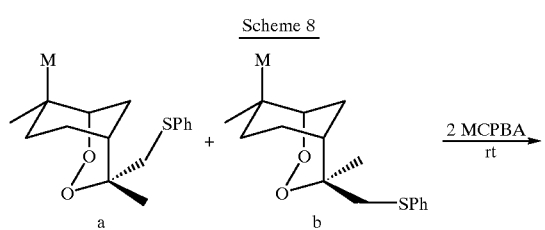

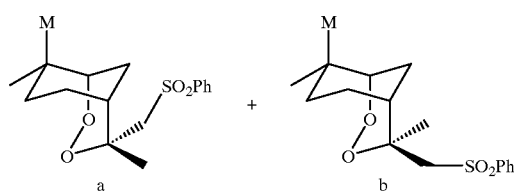

2a,b: R =OH;
11a,b: R =H;
13a,b: R = OAc;
14a,b: R = OCOCH$_2$COCH$_3$;
18a,b: R = OCOCOOEt;
19a,b: R = OCOCONBn$_2$;
20a,b: R = OCOPh;

21a,b: R =OH;
22a,b: R = H;
23a,b: R = OAc;
24a,b: R = OCOCH$_2$COCH$_3$;
25a,b: R = OCOCOOEt;
26a,b: R = OCOCONBn$_2$;
27a,b: R = OCOPh;

Scheme 9

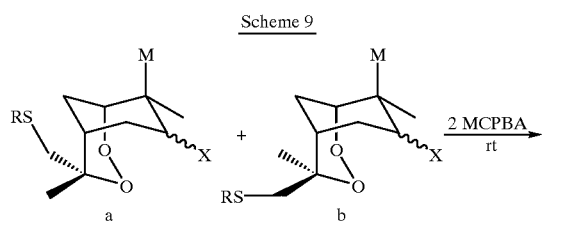

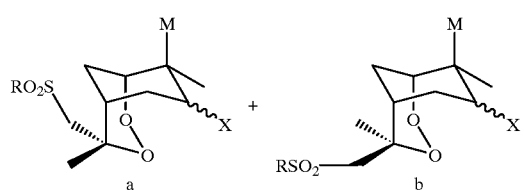

2′a,b: R = Ph, X = H, M = OH;
13′a,b: R = Ph, X = H, M = OAc;
4a,b: R = Ph, X = β-OBz, M = OH;
5a,b: R = n-Bu, X = β-OBz, M = OH;
6a,b: R = Ph, X = α-OBz, M = OH;

21′a,b: R = Ph, X = H, M = OH;
23′a,b: R = Ph, X = H, M = OAc;
29a,b: R = Ph, X = β-OBz, M = OH;
30a,b: R = n-Bu, X = β-OBz, M = OH;
31a,b: R = Ph, X = α-OBz, M = OH;

Scheme 10

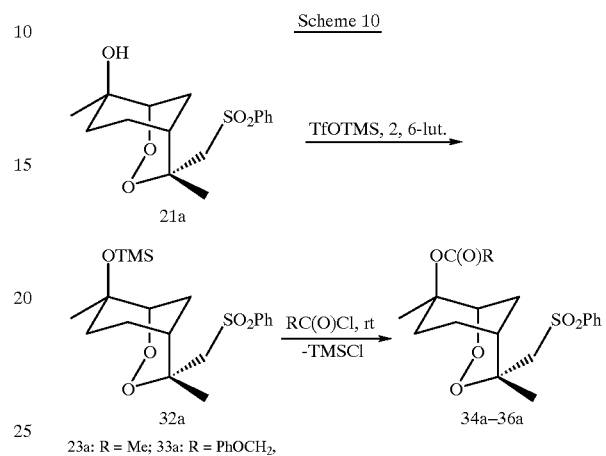

23a: R = Me; 33a: R = PhOCH$_2$,

Scheme 11

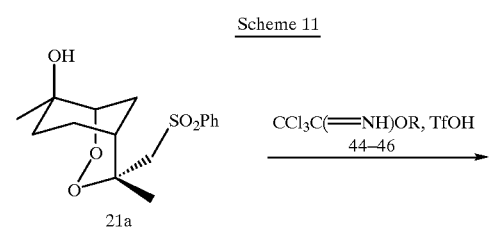

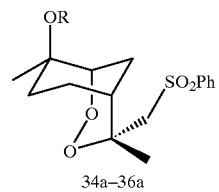

34a, 44: R = p-MeOC$_6$H$_4$CH$_2$;
35a, 45: R = CH$_2$CH=CMe$_2$;
36a, 46: R = trans-CH$_2$CH=CHPh

Scheme 12

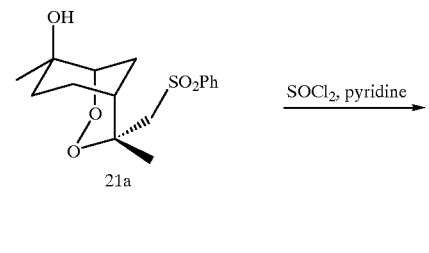

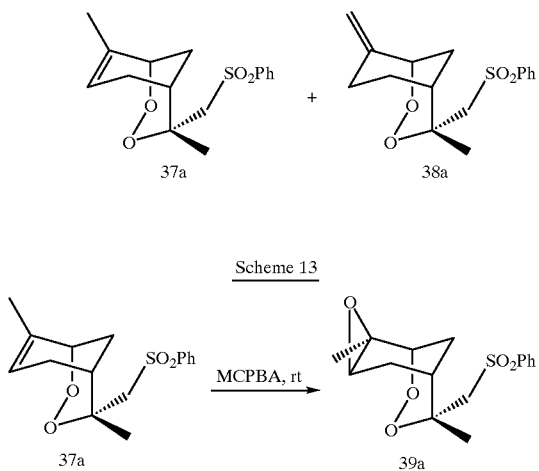

Scheme 13

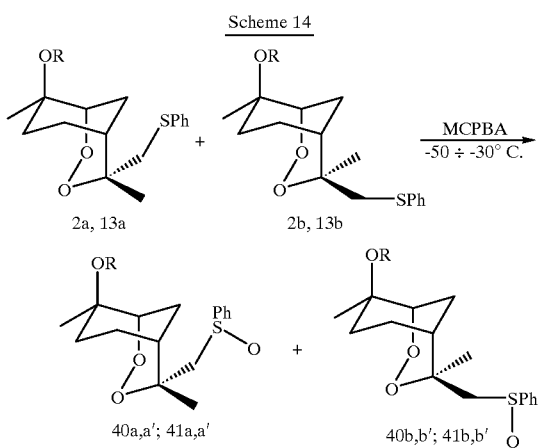

Scheme 14

2a,b: R = H;   40a,a′,b,b′: R = H;
13a,b: R = Ac   41a,a′,b,b′: R = Ac a and a′, b and b′ are epimers on the sulfur atom

EXAMPLE 1

Preparation of (1R,4R,5R,8R)-4,8-dimethyl-4-phenylthiomethyl-2,3-dioxabicyclo [3.3.1]nonan-8-ol (2a) and (1R,4S,5R,8R)-4,8-dimethyl-4-phenylthiomethyl-2,3-dioxabicyclo[3.3.1]nonan-8-ol (2b) (Scheme 1).

To a stirred solution of R-(+)-limonene 1 (6.13 g, 45 mmol) in a mixture of n-heptane (500 mL) and benzene (200 mL) was added in one portion di-tert-butyl peroxalate (DBPO) (105 mg, 0.45 mmol). Oxygen gas was bubbled through the mixture at rt, with simultaneous addition of a solution of thiophenol (PhSH) (1.653 g, 15 mmol) in benzene (20 mL) (syringe pump) over a period of 12 h. After the addition of PhSH was completed the mixture was exposed to oxygen for an additional 14 h. After addition of $CH_2Cl_2$ (100 mL) the mixture was cooled to 0–5° C. and powdered $Ph_3P$ (3.93 g, 15 mmol) was added in one portion. The mixture was then stirred for 2 h at 0–5° C. and for 1 h at rt, solvents were evaporated at rt Flash chromatography (silica gel 60, 230–400 mesh from Merck, gradient elution, EtOAc-hexane, from 1:49 to 3:7) followed by additional flash chromatography (EtOAc-hexane, 3:7) afforded a mixture of (1R,4R,5R,8R)-4,8-dimethyl-4-phenylthiomethyl-2,3-dioxabicyclo[3.3.1]nonan-8-ol (2a) and (1R,4S,5R,8R)-4,8-dimethyl-4-phenylthiomethyl-2,3-dioxabicyclo[3.3.1]nonan-8-ol (2b) (2a/2b ca. (55:45), 2.41 g (8.19 mmol, 54.6% yield), as a colorless or pale yellow oil, $R_f$ 0.29 (EtOAc-hexane 3:7), IR (neat): 690, 740, 1015, 1055, 1373, 1440, 1454, 1480, 1584, 2921, 2928, 2964, 3420 $cm^{-1}$. $^1H$ NMR ($CDCl_3$, 400 MHz) (δ): 1.25 (br. s, $Me^{11}$, 2a), 1.56 (d, $^4J_{11,12}$=0.6 Hz, $Me^{11}$, 2b), total 3 H; 1.39 (s, $Me^{10}$, 2b), 1.40 (s, $Me^{10}$, 2a), total 3 H; 1.58 (m, 1 H, $H_e^7$, 2a+2b); 1.76–1.85 (m, 2 H, $H_e^6$+$H_a^6$, 2a+2b); 1.81 (m, $H_e^5$, 2b), 1.91 (dddd, $^3J_{5e6e}$=$^3J_{5e9a}$=$^3J_{5e6a}$=$^3J_{5e9a}$=3.2 Hz, $H_e^5$, 2a), total 1 H; 1.98 (ddd, $^2J_{9a9e}$=13.6 Hz, $^3J_{9a5e}$=3.2 Hz, $^3J_{9a1e}$=2.0 Hz, $H_a^9$, 2a), 2.01 (ddd, $^2J_{9a9e}$=14.2 Hz, $^3J_{9a5e}$=3.2 Hz, $^3J_{9a1e}$=1.9 Hz, $H_a^9$,2b), total 1 H; 2.10 (ddd, $^2J_{9e9a}$=13.6 Hz, $^3J_{9e1e}$=5.5 Hz, $^3J_{9e5e}$=3.2 Hz, $H_e^9$,2a), 2.26 (ddd, $^2J_{9e9a}$=14.2 Hz, $J_{9e1e}$=4.4 Hz, $^3J_{9e5e}$=3.0 Hz, $H_e^9$, 2b), total 1 H; 2.31–2.41 (m, 1 H, $H_a^7$, 2a+2b); 2.96 (d, $^2J$=12.0 Hz, $H^{12}$, 2b), 3.35 (d, $^2J$=12.8 Hz, $H^{12}$, 2a), total 1 H; 3.03 (dd, $^2J$=12.0 Hz, $^4J_{12,11}$=0.6 Hz, $H'^{12}$, 2b), 3.71 (dd, $^2J$=12.8 Hz, $^4J_{12,11}$=0.5 Hz, $H'^{12}$,2a), total 1 H; 3.68 (m, $H^1$, 2a), 3.71 (m, $H^1$, 2b), total 1 H; 7.17–7.23 (m, 1 H, $H^{16}$, 2a+2b); 7.27–7.33 (m, 2 H, $H^{15}$, 2a+2b);

Scheme 15

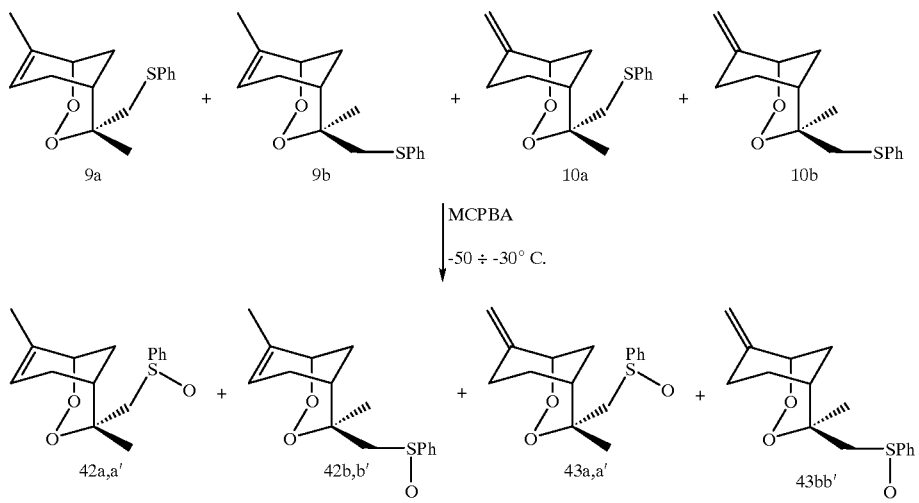

7.36–7.43 (m, 2 H, H$^{14}$,2a+2b). $^{13}$C NMR (CDCl$_3$, 100 MHz) ($\delta$): Isomer 2a: 21.89 (Me$^{11}$), 23.58 (C$^6$H$_2$), 24.17 (C$^9$H$_2$), 28.04 (Me$^{10}$), 29.23 (C$^5$H), 35.51 (C$^7$H$_2$), 40.68 (C$^{12}$H$_2$), 71.40 (C$^8$), 81.57 (C$^1$H), 83.77 (C$^4$), 126.14 (C$^{16}$H), 128.87 (2C$^{14}$H), 129.63 (2C$^{15}$H), 136.84 (C$^{13}$); Isomer 2b: 21.76 (Me$^{11}$), 23.30 (C$^6$H$_2$), 24.26 (C$^9$H$_2$), 28.04 (Me$^{10}$), 30.50 (C$^5$H), 35.84 (C$^7$H$_2$), 40.73 (C$^{12}$H$_2$), 71.35 (C$^8$), 82.02 (C$^1$H), 83.83 (C$^4$), 126.33 (C$^{16}$H), 128.93 (2C$^{14}$H), 129.63 (2C$^{15}$H, 136.42 (C$^{13}$). R-(+)-Limonene 1 (2.73 g, 20.0 mmol, 66.8%) was recovered in the first chromatography

EXAMPLE 2

Preparation of (1S,4S,5S,8S)-4,8-dimethyl-4-phenylthiomethyl-2,3-dioxabicyclo [3.3.1]nonan-8-ol (2'a) and (1S,4R,5S,8S)-4,8-dimethyl-4-phenylthio-methyl-2,3-dioxabicyclo[3.3.1]nonan-8-ol (2'b) (Scheme 2).

The title compounds were obtained in 53.7% yield (8.0 mmol) from S(−)-limonene 1' using the procedure for the preparation of compounds 2a,b from R(+)-limonene. $^1$H NMR and IR spectra are consistent with those described for (1R,4R,5R,8R)- and (1R,4S,5R,8R)-diastereomers 2a,b.

EXAMPLE 3

Preparation of (1R,4S,5S,7S,8S)-7-benzoyloxy-4,8-dimethyl-4-phenylthiomethyl-2,3-dioxabicyclo[3.3.1]nonan-8-ol (4a) and (1R,4R,5S,7S,8S)-7-benzoyloxy-4,8-dimethyl-4-phenylthio-methyl-2,3-dioxabicyclo[3.3.1]nonan-8-ol (4b) (Scheme 2).

Oxygen was bubbled through a solution of the $\beta$-benzoate 3a (350 mg, 1.36 mmol) and DBPO (4.3 mg, 0.018 mmol) in benezene-n-heptane (20 mL, 1:1) for 10 h with simultaneous addition of a solution of PhSH (50 mg, 0.45 mmol) in heptane (10 mL) (syringe pump). After completion of the thiol addition, the mixture was kept under oxygen for an addition 15 h, diluted with CH$_2$Cl$_2$ (10 mL), cooled to 4° C. and Ph$_3$P (118 mg, 0.45 mmol) was added in 4 portions. The mixture was stirred at 4° C. for 1 h and at rt for an additional 1 h, the solvents were evaporated, and flash chromatography (hexane-EtOA, 3:1) afforded a mixture (42 mg, 22.3% yield) of (1R,4S,5S,7S,8S)-7-benzoyloxy-4,8-dimethyl-4-phenylthiomethyl-2,3-dioxabicyclo[3.3.1]nonan-8-ol 4a (less polar isomer) and (1R,4R,5S,7S,8S)-7-benzoyloxy-4,8-dimethyl-4-phenylthiomethyl-2,3-dioxabicyclo[3.3.1] nonan-8-ol 4b (more polar isomer, (4a/4b ca. 50:50), R$_f$ 0.26 (EtOAc-hexane, 1:3), colorless semisolid. IR (neat): 3547, 1713, 1271, 711 cm$^{-1}$. Additional flash chromatography afforded a sample of crystalline 4a (less polar isomer), mp 139–140° C. $^1$H NMR (400 MHz, CDCl$_3$, $\delta$): 1.37 (br. s, 3 H, Me$^{11}$), 1.44 (s, 3 H, Me$^{10}$), 1.83 (ddd, 1 H, $^2$J=13.1 Hz, $^3$J$_{6a7a}$=11.6 Hz, $^3$J$_{6a5e}$=3.3 Hz, H$_a^6$), 2.08 (m, 2 H, H$_a^9$+H$_e^9$), 2.20 (m, 1 H, H$_e^5$), 2.37 (m, 1 H, H$_e^6$), 3.35 (d, 1 H, $^2$J=12.9 Hz, H$^{12}$), 3.73 (br. d, 1 H, $^2$J=12.9 Hz, H'$^{12}$), 3.96 (dd, 1 H, $^3$J$_{1e9e}$=$^3$J$_{1e9a}$=2.4 Hz, H$_e^1$), 5.76 (dd, 1 H, $^3$J$_{7a6a}$=11.6 Hz, $^3$J$_{7a6e}$=6.3 Hz, H$_a^7$), 7.20 (m, 1 H, H$^{16}$), 7.30 (m, 2 H, H$^{15,15'}$), 7.42 (m, 2 H, H$^{14,14'}$), 7.48 (m, 2 H, H$^{meta-benz.}$), 7.60 (m, 1 H, H$^{para-benz.}$), 8.03 (m, 1 H, H$^{ortho-benz.}$). $^{13}$C NMR (100 MHz, CDCl$_3$,$\delta$): 22.30 (Me$^{11}$), 23.68 (C$^9$H$_2$), 24.46 (Me$^{10}$), 29.23 (C$^6$H$_2$), 31.31 (C$^5$H), 40.54 (C$^{12}$H$_2$), 72.81 (C$^8$), 74.75 (C$^6$H), 82.75 (C$^1$H), 83.79 (C$^4$), 126.43 (C$^{16}$H), 128.54 (2CH), 129.03 (2CH), 129.48 (2CH), 129.94 (2CH), 130.07 (C$^{1-benz.}$), 133.24 (C$^{p-benz.H}$), 136.56 (C$^{13}$), 165.59 (C=O). More polar isomer 4b: $^1$H NMR (400 MHz, CDCl$_3$, $\delta$): 1.43 (s, 3H, Me$^{10}$), 1.58 (br.s, 3 H, Me$^{11}$), 1.77 (ddd, 1 H, $^2$J=12.8 Hz, $^3$J$_{6a7a}$=11.2 Hz, $^3$J$_{6a5e}$=3.4 Hz, H$_a^6$), 2.07–2.36 (m, 4 H, H$_e^5$+H$_e^6$+H$_{e,a}^9$), 3.03 (d, 1 H, $^2$J=12.3 Hz, H$^{12}$), 3.24 (br. d, 1 H, $^2$J=12.3 Hz, H'$^{12}$), 3.99 (m, 1 H, H$_e^1$), 5.78 (dd, 1 H, $^3$J$_{7a6a}$=11.2 Hz, $^3$J$_{7a6e}$=6.3 Hz, H$_a^7$), 7.21 (m, 1 H, H$^{16}$), 7.30 (m, 2 H, H$^{15,15'}$), 7.42 (m, 2 H, H$^{14,14'}$), 7.48 (m, 2 H, H$^{meta-benz.}$), 7.59 (m, 1 H, H$^{para-benz.}$), 8.03 (m, 1 H, H$^{ortho-benz.}$). $^{13}$C NMR (100 MHz, CDCl$_3$,$\delta$): 21.40 (Me$^{11}$), 23.80 (C$^9$H$_2$), 24.46 (Me$^{10}$), 28.99 (C$^6$H$_2$), 32.53 (C$^5$H), 40.70 (C$^{12}$H$_2$), 72.83 (C$^8$), 74.81 (C$^7$H), 83.23 (C$^1$H), 83.88 (C$^4$), 126.51 (C$^{16}$H), 128.52 (2CH), 129.03 (2CH), 129.48 (2CH), 129.90 (2CH), 130.08 (C$^{1-benz.}$), 133.20 (C$^{p-benz.H}$), 135.99 (C$^{13}$), 165.52 (C=O).

EXAMPLE 4

Preparation of (1R,4S,5S,7S,8S)-7-benzoyloxy-4-n-butylthiomethyl-4,8-dimethyl-2,3-dioxabicyclo[3.3.1]nonan-8-ol (5a) and (1S,4R,5S,7S,8S)-7-benzoyloxy-4-n-butylthiomethyl-4,8-dimethyl-2,3-dioxabicyclo[3.3.1]nonan-8-ol (5b) Scheme 2).

Oxygen was bubbled through a solution of the $\beta$-benzoate 3a (993 mg, 3.87 mmol) and DBPO (23 mg, 0.1 mmol) in hexane-benzene (50 mL, 4:1) with simultaneous addition (syringe pump) during 10 h a solution of n-BuSH (180 mg, 2.0 mmol) in hexane (20 mL). After completion of the addition the mixture was kept under oxygen for an additional 14 h, cooled to 5° C., and Ph$_3$P (526 mg, 2.0 mmol) was added. The reaction mixture was stirred for 2 h at 5° C., for additional 1 h at rt and then evaporated. Flash chromatography (hexane-EtOAc, 9:1→7:3) afforded a mixture of diastereomeric (1S,4S,5S,7S,8S)-7-benzoyloxy-4-n-butylthiomethyl-4,8-dimethyl-2,3-dioxabicyclo[3.3.1]nonan-8-ol 5a and (1S,4R,5S,7S,8S)-7-benzoyloxy-4-n-butylthiomethyl-4,8-dimethyl-2,3-dioxabicyclo[3.3.1]nonan-8-ol 5b (59 mg of ~85% purity, ca. 6.5% yield; 5a/5b ca. 55:45) as a pale yellow viscous liquid, R$_f$ 0.26 (hexane-EtOAc, 4:1). $^1$H NMR (400 MHz, CDCl$_3$, $\delta$): 0.91 (t, $^3$J=7.3 Hz, Me$^{16}$CH$_2$, 5b), 0.92 (t, $^3$J=7.3 Hz, Me$^{16}$CH$_2$, 5a), total 3 H; 1.36 (br. s, Me$^{11}$, 5a), 1.58 (br. s, Me$^{11}$, 5b), total 3 H, 1.42 (m, 2 H, MeC$^{15}$H$_2$), 1.43 (s, Me$^{10}$, 5b), 1.44 (s, Me$^{10}$, 5a), total 3 H; 1.60 (m, 2 H, C$^{14}$H$_2$CH$_2$S), 1.78 (ddd, $^2$J=13.3 Hz, $^3$J$_{6a7a}$=11.6 Hz, $^3$J$_{6a5e}$=3.4 Hz, H$_a^6$, 5b), 1.82 (ddd, $^2$J=13.2 Hz, $^3$J$_{6a7a}$=11.8 Hz, $^3$J$_{6a5e}$=3.5 Hz, H$_a^6$, 5a), 1 H total; 1.96–2.52 (m, total 4 H, H$_e^5$+H$_e^6$+H$_{e,a}^9$, 5a+5b), 2.59 (br. t, $^3$J=7.3 Hz, CH$_2$S, 5a), 2.61 (br. t, $^3$J=7.3 Hz, C$^{13}$H$_2$S, 5b), total 2 H; 2.60 (br. d, $^2$J=12.2 Hz, H$^{12}$,5b), 2.80 (br. d, $^2$J=12.2 Hz, H'$^{12}$,5b), 2.96 (br. d, $^2$J=13.2 Hz, H$^{12}$, 5a), 3.20 (br. d, $^2$J=13.2 Hz, H'$^{12}$, 5a), total 2 H; 3.97 (br. s, 1 H, H$_e^1$, 5a +5b), 5.76 (m, 1 H, H$_a^7$, 5a+5b), 7.46 (m, 2 H, H$^{m-benz.}$, 5a+5b), 7.59 (m, 1 H, H$^{p-benz.}$, 5a+5b), 8.03 (m, 2 H, H$^{o-benz.}$, 5a+5b); $^{13}$C NMR (100 MHz, CDCl$_3$, $\delta$): Isomer 5a: 13.67 (Me$^{16}$), 21.89 (C$^{15}$H$_2$), 22.09 (Me$^{11}$), 23.79 (C$^9$H$_2$), 24.44 (Me$^{10}$), 29.33 (C$^6$H$_2$), 31.58 (C$^5$H), 31.82 (C$^{14}$H$_2$), 33.47 (C$^{13}$H$_2$), 38.16 (C$^{12}$H$_2$), 72.81 (C$^8$), 74.79 (C$^7$H), 82.73 (C$^1$H), 83.81 (C$^4$), 128.50 (2C$^{m-benz.}$H), 129.46 (2C$^{o-benz.H}$), 130.05 (C$^{1-benz.}$), 133.20 (C$^{p-benz.H}$), 165.58 (C=O); Isomer 5b: 13.62 (Me$^{16}$), 20.66 (Me$^{11}$), 21.85 (C$^{15}$H$_2$), 23.89 (C$^9$H$_2$), 24.44 (Me$^{10}$), 28.99 (C$^6$H$_2$), 31.54 (C$^{14}$H$_2$), 32.59 (C$^5$H), 33.67 (C$^{13}$H$_2$), 38.88 (C$^{12}$H$_2$), 72.80 (C$^8$), 74.96 (C$^7$H), 83.15 (C$^1$H), 83.92 (C$^4$), 128.50 (2C$^{m-benz.H}$), 129.46 (2C$^{o-benz.H}$), 130.09 (C$^{1-benz.}$), 133.17 (C$^{p-benz.H}$), 165.58 (C=O).

EXAMPLE 5

Preparation of (1S,4S,5S,7R,8S)-7-benzoyloxy-4,8-dimethyl-4-phenylthiomethyl-2,3-dioxabicyclo[3.3.1]nonan-8-ol (6a) and (1R,4S,5R,8R)-7-benzoyloxy-4,8-dimethyl-4-phenylthiomethyl-2,3-dioxabicyclo[3.3.1]nonan-8-ol (6b) (Scheme 2).

Oxygen was bubbled through a solution of the α-benzoate 3b (690 mg, 2.70 mmol) and DBPO (8.5 mg, 0.036 mmol) in hexane-benzene (50 mL, 7:3) with simultaneous addition (syringe pump) of a solution of PhSH (99 mg, 2.0 mmol) in hexane (20 mL) during 10 h. After completion of the thiol addition, the mixture was kept under oxygen for an additional 14 h, cooled to 4° C., and Ph$_3$P (236 mg, 0.90 mmol) was added. The reaction mixture was stirred for 2 h at 5° C. and at rt for additional 1 h. The solvents were then evaporated, and flash chromatography (hexane-EtOAc, 9:1→1:1) afforded a mixture of diastereomeric (1S,4S,5S,7R,8S)-7-benzoyloxy-4,8-dimethyl-4-phenylthiomethyl-2,3-dioxabicyclo[3.3.1]nonan-8-ol 6a and (1S,4R,5S,7R,8R)-7-benzoyloxy-4,8-dimethyl-4-phenylthiomethyl-2,3-dioxabicyclo[3.3.1]nonan-8-ol 6b (24 mg of ca. 94% purity, 6% yield, 6a/6b ca. 65:35), R$_f$ 0.42 (EtOAc-heaxane, 35:65) as a pale yellow oil. $^1$H NMR (400) MHz, CDCl$_3$, δ): 1.23 (br. s, Me$^{11}$, 6a), 1.59 (br. s, Me$^{11}$, 6b), total 3 H; 1.41 (s, Me$^{10}$, 6b), 1.42 (s, Me$^{10}$, 6a), total 3 H; 1.91–2.37 (m, total 5 H, H$_3^5$+H$_{a,e}^6$+H$_{a,e}^9$, 6a+6b); 3.00 (d, $^2$J=12.1 Hz, H$^{12}$, 6b), 3.14 (br. d, $^2$J=12.1 Hz, H$^{12}$, 6b), 3.39 (d, $^2$J=12.8 Hz, H$^{12}$, 6a), 3.80 (br. d, $^2$J=12.8 Hz, H$^{12}$, 6a), total 2 H; 3.82 (m, H$_e^1$, 6a), 3.88 (dd, $^3$J$_{1e9e}$=4.1 Hz, $^3$J$_{1e9a}$=1.5 Hz, H$_e^1$, 6b), total 1 H; 5.26 (dd, 1 H, $^3$J$_{7e6e}$=5.0 Hz, $^3$J$_{7e6a}$=1.7 Hz, H$_e^7$, 6b), 5.27 (dd, 1 H, $^1$J$_{7e6e}$=5.0 Hz, $^3$J$_{7e6a}$=1.5 Hz, H$_e^7$, 6a), total 1 H; 7.09 (m, 1 H), 7.22 (m, 6 b), 7.29 (m, 6a), total 2 H; 7.41–7.47 (m,), 7.54–7.58 (m,), total 5 H; 8.13 (m, 2 H), $^{13}$C NMR (100 MHz, CDCl$_3$, δ): Isomer 6a: 22.30 (Me$^{11}$), 23.42 (C$^9$H$_2$), 23.47 (Me$^{10}$), 28.81 (C$^6$H$_2$), 29.36 (C$^5$H), 40.78 (C$^{12}$H$_2$), 73.83 (C$^8$), 74.36 (C$^7$H), 80.85 (C$^1$H), 82.74 (C$^4$), 126.36 (C$^{16}$H), 128.48 (2CH), 129.00 (2CH), 129.81 (2CH), 129.90 (2CH), 130.15 (C$^{1-benz.}$), 133.11 (C$^{p-benz.}$H), 136.71 (C$^{13}$), 166.33 (C=O); Isomer 6b: 21.68 (Me$^{11}$), 23.35 (Me$^{10}$), 23.56 (C$^9$H$_2$), 28.68 (C$^6$H$_2$), 30.86 (C$^5$H), 40.37 (C$^{12}$H$_2$), 73.68 (C$^8$), 74.51 (C$^7$H), 81.38 (C$^1$H), 82,83 (C$^4$), 126.12 (C$^{16}$H), 128.52 (2CH), 128.88 (2CH), 129.06 (2CH), 129.81 (C$^{1-benz.}$), 129.90 (2CH), 133.18 (C$^{p-benz.}$H), 136.25 (C$^{13}$), 166.25 (C=O).

EXAMPLE 6

Preparation of (1R,4S,5R,8R)-7-benzoyloxy-4,8-dimethyl-4-phenylthiomethyl-2,3-dioxabicyclo[3.3.1]nonan-8-ol (7a) (Scheme 2).

Oxygen was bubbled through a solutionof α-carveol 3c (2.284 g, 15 mmol) and DBPO (47 mg, 0.2 mmol) in benzene-n-hexane (250 mL, 1:1) with simultaneous addition (syringe pump) of a solution of PhSH (550 mg, 5.0 mmol) in hexane (20 mL) during 12 h. After completion of the thiol addition, the mixture was kept under oxygen for an additional 12 h, cooled to 5° C. and Ph$_3$P (1.31 g, 5.0 mmol) was added in 3 portions. The mixture was stirred at 5° C. for 2 h and for an additional 2 hr at rt, the solvents were evaporated, and flash chromatography (hexane-EtOAc, 3:1→1:1) afforded (1R,4S,5R,8R)-7-benzoyloxy-4,8-dimethyl-4-phenylthiomethyl-2,3-dioxabicyclo[3.3.1]nonan-8-ol monohydrate 7a (194 mg, 11.8% yield) as colorless needles, mp 108–109° C. (hexane-EtOAc, 5:1), R$_f$ 0.20 (EtOAc-hexane, 50:50). $^1$H NMR (400 MHz, CDCl$_3$, δ); 1.36 (br. s, 3 H, Me$^{11}$), 1.45 (s, 3 H, Me$^{10}$), 1.96–2.06 (m, total 3 H, H$_e^5$+H$_{a,e}^9$), 2.09 (ddd, 1 H, $^2$J=16.0 Hz, $^3$J$_{6a5e}$=3.7 Hz, $^3$J$_{6a7e}$=1.4 Hz, H$_a^6$), 2.18 (ddd, 1 H, $^2$J=16.0 Hz, $^3$J$_{6e7e}$=5.5 Hz, $^3$J$_{6e5e}$=4.4 Hz H$_e^6$), 3.37 (d, 1 H, $^2$J=12.9 Hz, H$^{12}$), 3.55 (br. dd, 1 H, $^3$J$_{7e,OH}$=13.2 Hz, $^3$J$_{7e6e}$=5.5 Hz, H$_e^7$), 3.76 (dd, 1 H, $^2$J=12.9 Hz, $^4$J$_{12',11}$=0.6 Hz, H$^{12}$), 3.76 (m, 1 H, H$_e^1$), 4.09 (d, 1 H, $^3$J$_{HO,7e}$=13.2 Hz, OH, exch. with CD$_3$COOD), 7.22 (m, 1 H, H$^{16}$), 7.32 (m, 2 H, 2H$^{15}$), 7.42 (m, 2 H, 2 H$^{14}$). $^{13}$C NMR (100 MHz, CDCl$_3$, δ): 22.22 (Me$^{11}$), 22.91 (C$^9$H$_2$), 24.57 (Me$^{10}$), 29.95 (C$^5$H), 30.92 (C$^6$H$_2$), 40.55 (C$^{12}$H$_2$), 72.98 (C$^7$H), 74.21 (C$^8$), 82.19 (C$^1$H), 83.86 (C$^4$), 126.56 (C$^{16}$H), 129.03 (2C$^{15}$H), 130.07 (2C$^{14}$H), 136.35 (C$^{13}$). Anal. Calcd for C$_{16}$H$_{22}$O$_4$S×H$_2$O: C, 58.51; H 7.36; S, 9.76. Found: C, 58.48; H 7.34; S, 9.27.

EXAMPLE 7

Preparation of (1R,4R,5R)-4,8-dimethyl-4-phenylthiomethyl-2,3-dioxabicyclo[3.3.1]nonan-7-ene (9a), (1R,4S,5R)-4,8-dimethyl-4-phenylthiomethyl-2,3-dioxabicyclo[3.3.1]nonan-7-ene (9b), (1R,4R,5R)-4,8-dimethyl-8-methylidene-4-phenylthiomethyl-2,3-dioxabicyclo[3.3.1]nonan (10a) and (1R,4S,5R)-4-methyl-8-methylidene-4-phenylthiomethyl-2,3-dioxabicyclo[3.3.1]nonan (10b) (Scheme 3).

To a mixture of SOCl$_2$ (1.90 g, 16.0 mmol) and pyridine (3.165 g, 40.0 mmol) in CH$_2$Cl$_2$ (150 mL) at −30÷−40° C. was added during 1.5 h a solution of hydroxysulfides 2a,b (1.10 g, 3.74 mmol, ratio 2a/2b ca. 55:45) in CH$_2$Cl$_2$ (30 mL). The temperature raised to 25° C. and the mixture was stirred for additional 4 h. The resulting mixture was poured into ice-cold 0.1 M HCl (100 mL), extracted with hexane-EtOAc (9:1, 2×300 mL), the organic layer was washed with saturated NaHCO$_3$ (2×80 mL), dried (Na$_2$SO$_4$+NaHCO$_3$) and evaporated. The residue was purified by flash chromatography (hexane-EtOAc, 95:5) to give a mixture of unsaturated sulfides 9a,b and 10a,b (798 mg, total 80%, consisting of 9a, ca. 47%, 9b, 39%, 10a; 8%; and 10b, 6% according the integration of the C$^1$H peaks in 400 MHz $^1$H NMR spectrum). $^1$H NMR (400 MHz, CDCl$_3$, δ): 1.20 (d, $^4$J=0.7 Hz, Me$^{11}$ 9a), 1.29 (d, $^4$J=0.6 Hz, Me$^{11}$ 10a), 1.57 (d, $^4$J=0.5 Hz, Me$^{11}$ 10b), 1.58 (d, $^4$J=0.8 Hz, Me$^{11}$ 9b), total 3 H; 1.55 (ddd, $^2$J=13.1 Hz, $^3$J$_{9a5e}$=3.0 Hz, $^3$J$_{9a1e}$=2.0 Hz, H$_q^9$9a), 1.63 (dddd, $^2$J=13.0 Hz, $^3$J$_{9a5e}$=2.9 Hz, $^3$J$_{9a1e}$=2.4 Hz, $^4$J=0.5 Hz, H$_a^9$9b), 1 H; 1.79–1.81 (m, ca. 3 H, Me$^{10}$9a,b), 1.93 (m, H$_e^5$9b), 2.04 (m, H$_e^5$9a), total ca. 1 H; 2.15–2.37 (m), 2.48 (dddd, $^2$J=13.0 Hz, $^3$J$_{9e5e}$=$^3$J$_{9e1e}$=3.6 Hz, $^4$J$_{9e6e}$=1.6 Hz, H$_e^9$9b), total 3 H; 2.90 (d, $^2$J=11.8 Hz, H$^{12}$ 9b) and 2.99 (dd, $^2$J=11.8 Hz, $^4$J$_{12,11}$=0.8 Hz, H$^{'12}$ 9b), 3.00 (d, $^2$J=12.0 Hz, H$^{12}$ 10b) and 3.10 (dd, $^2$J=12.0 Hz, $^4$J$_{12,11}$=0.5 Hz, H$^{'12}$ 10b), 3.30 (d, $^2$J=12.2 Hz, H$^{12}$ 10a), 3.33 (d, $^2$J=12.7 Hz, H$^{12}$ 9a) and 3.79 (dd, $^2$J=12.7 Hz, $^4$J$_{12,11}$=0.7 Hz, H$^{'12}$ 9a), total 2 H; 4.10 (m, $^3$J$_{1e9e}$=3.6 Hz, $^3$J$_{1e9a}$=2.0 Hz, H$_e^1$, 9a), 4.13 (br. dd, $^3$J$_{1e9e}$=3.6 Hz, $^3$J$_{1e9a}$=2.4 Hz, H$_e^1$ 9b), 4.34 (br. dd, $^3$J$_{1e9e}$=4.0 Hz, $^3$J$_{1e9a}$=1.4 Hz, H$_e^1$, 10a), 4.40 (br. dd, $^3$J$_{1e9e}$=4.3 Hz, $^3$J$_{1e9a}$=1.7 Hz, H$_e^1$10b), total 1 H; 4.89–4.93 (m, HH'C$^{10}$=10a,b), 5.73 (m, H$^7$9b), 5.75 (m, H$^7$9a), total ca. 1 H; 7.18–7.46 (m, 5 H).

By an additional preparative RP HPLC (column LiChrosorb® RP-8 (7 μm) 250–25; eluent-MeCN-H$_2$O, 60:40) single diastereomer (1R,4R,5R)-4,8-dimethyl-4-phenylthiomethyl-2,3-dioxabicyclo[3.3.1]non-7-ene 9a (ca. 97% purity) was isolated: a colorles waxy substance, mp 60–63° C. $^1$H NMR (400 MHz, CDCl$_3$, δ): 1.20 (d, 3 H, $^4$J=0.6 Hz, Me$^{11}$), 1.55 (ddd, 1 H, $^2$J=13.1 Hz, $^3$J$_{9a5e}$=3.0 Hz, $^3$J$_{9a1e}$=2.0 Hz, H$_a^9$), 1.80 (ddd, 3 H, $^5$J$_{10,6a}$=2.7 Hz, $^5$J$_{10,6e}$=$^4$J$_{10,7}$=1.6 Mz, Me$^{10}$), 2.04 (m, 1 H, H$_e^5$), 2.21 (dddq, 1 H, $^2$J=19.0 Hz, $^3$J$_{6a7}$=5.4 Hz, $^3$J$_{6a5e}$=$^5$J$_{6a10}$=2.7 Hz, H$_a^6$), 2.30 (dddd, 1 H, $^2$J=13.1 Hz, $^3$J$_{9e5e}$=$^3$J$_{9e1e}$=3.6 Hz, $^4$J$_{9e6e}$=1.6 Hz, H$_e^9$), 2.33 (dddq, 1 H, $^2$J=19.0 Hz, $^3$J$_{6e7}$=6.4 Hz, $^3$J$_{6e5e}$=$^5$J$_{6e10}$=1.6 Hz, H$_e^6$), 3.34 (d, 1 H, $^2$J=12.7 Hz, H$^{12}$), 3.79 (br. dd, $^2$J=12.7 Hz, $^4$J$_{12',11}$=0.7 Hz, H$^{'12}$), 4.10 (m, 1 H, $^3$J$_{1e9e}$=3.6 Hz, $^3$J$_{1e9a}$=2.0 Hz, H$_e^1$), 5.76 (m, 1 H, H$^7$), 7.19 (m, 1 H, H$^{16}$), 7.29 (m, 2 H, H$^{15,15'}$), 7.42 (m, 2 H, H$^{14,14'}$). $^{13}$C NMR (100 MHz, CDCl$_3$, δ); 21.17 Me$^{10}$), 22.72 (Me$^{11}$), 26.38 (C$^9$H$_2$), 27.56 (C$^6$H$_2$), 28.52 (C$^5$H), 40.73 (C$^{12}$H$_2$), 76.21 (C$^1$H), 83.37 (C$^4$), 126.15 (C$^{16}$H), 126.82 (C$^7$H), 128.90 (2C$^{15}$H), 129.69 (2C$^{14}$H), 131.26 (C$^8$=), 136.96 (C$^{13}$).

EXAMPLE 8

Preparation of (1R,4R,5R,8S)-4,8-dimethyl-4-phenylthiomethyl-2,3-dioxabicyclo[3.3.1]non-7-ene (11a), (1R,4R,5R)-4,8-dimethyl-4-phenylthiomethyl-2,3-dioxabicyclo[3.3.1]nonane (11b), (1R,4S,5R,8S)-4,8-dimethyl-4-phenylthiomethyl-2,3-dioxabicyclo[3.3.1]nonane (12a) and (1R,4S,5R,8R)-4,8-dimethyl-4-phenylthiomethyl-2,3-dioxabicyclo[3.3.1]nonane (12b) (Scheme 4).

To a mixture of unsaturated sulfides 9a,b and 10a,b (total 120 mg, 0.43 mmol; ratio 9a: 9b: 10a: 10b ca. 54:34:6.5:5.5) and potassium azodicarboxylate (1.00 g, 5.15 mmol) in MeOH (3 mL) and $CH_2Cl_2$ (2 mL) at 0° C. for 45 min was added a solution of AcOH (620 mg, 10.32 mmol) in $CH_2Cl_2$ (2 mL). Temperature was slowly raised to 25° C. (2 h) and the reaction mixture was stirred for an additional 48 h. The mixture was diluted with ether (50 mL), filtered through Celite® and evaporated. The residue was separated by several consecutive MPLC (hexane-EtOAc, 98:2) to give starting material 9a,b (70 mg, 0.25 mmol; 9a/9b ca. 61:39), sulfides 12a (4 mg), 12b (3 mg), and two fractions consisted of mixtures of 11a,b with different ratio of isomers: (4 mg, 11a/11b 83:17) and (19 mg, 11a/11b 53:47). 11a,b: $^1$H NMR (CDCl$_3$, 400 MHz) (δ): 1.09 (d, $^3J$=6.7 Hz, Me$^{10}$, 11b), 1.10 (d, $^3J$=6.7 Hz, Me$^{10}$, 11a), total 3 H; 1.24 (br. s, Me$^{11}$, 11a), 1.55 (d, $^4J_{11,12}$=0.7 Hz, Me$^{11}$, 11b), total 3 H; 1.41 (ddd, $^3J$=13.3 Hz, $^3J_{9a5e}$=3.0 Hz, $^3J_{9a1e}$=1.7 Hz, $H_a^9$ 11a), 1.48 (ddd, $^2J$=13.1 Hz, $^3J_{9a5e}$=3.2 Hz, $^3J_{9a1e}$=1.7 Hz, $H_a^9$ 11b), total 1 H; 1.58–1.69 (m, 2 H, $H_e^6$+$H_a^6$, 11a+11b); 1.75–1.85 (m, 1 H, $H_a^8$, 11a+11b); 1.90–1.94 (m, 1 H, $H_e^5$, 11a+11b); 1.94–2.05 (m, $H_e^7$+$H_a^7$, s11a+11b); 2.28 (dddd, $^3J_{9e9a}$=13.3 Hz, $^3J_{9e1e}$=$^3J_{9e5e}$=4.0 Hz, $^4J_{9e6e}$=2.6 Hz, $H_e^9$, 11a), 2.45 (dddd, $^2J_{9e9a}$=13.1 Hz, $^3J_{9e1e}$=$^3J_{9e5e}$=3.8 Hz, $^4J_{9e6e}$=2.9 Hz, $H_e^9$, 11b), total 1 H; 2.94 (d, $^2J$=11.9 Hz, H$^{12}$, 11b) and 3.05 (dd, $^2J$=11.9 Hz, $^4J_{12,11}$=0.7 Hz, H$^{'12}$, 11b), 3.31 (d, $^2J$=12.7 Hz, H$^{12}$, 11a), and 3.73 (dd, $^2J$=12.7 Hz, $^4J_{12,11}$=0.7 Hz, H$^{'12}$,11a), total 2 H; 3.83 (m, $^3J_{1e9e}$=4.0 Hz, $^3J_{1e9a}$=1.7 Hz, $H_e^1$, 11a), 3.86 (m, $^3J_{1e9e}$=3.8 Hz, $^3J_{1e9a}$=1.7 Hz, $H_e^1$, 11b), total 1 H; 7.17–7.43 (m, 5 H, 11a+11b). Isomer 11a: $^{13}$C NMR (CDCl$_3$, 100 MHz) (δ): 18.56 (Me$^{10}$), 22.05 (Me$^{11}$), 27.06 (CH$_2$), 29.19 (C$^5$H), 29.56 (CH$_2$), 29.59 (CH$_2$), 35.62 (C$^8$H), 40.91 (C$^{12}$H$_2$), 79.23 (C$^1$H), 83.36 (C$^4$), 126.07 (C$^{16}$H), 128.90 (2C$^{15}$H), 129.59 (2C$^{14}$H), 136.90 (C$^{13}$). Isomer 12a: $^1$H NMR (CDCl$_3$, 400 MHz) (δ): 1.02 (d, 3 H, $^3J$=7.4 Hz, Me$^{10}$), 1.25 (d, 3H, $^4J_{11,12}$=0.6 Hz, Me$^{11}$), 1.29 (br.dd, 1H, $^2J$=14.0 Hz, $^3J_{7e6e}$=5.8 Hz, $H_e^7$), 1.62 (ddd, 1H, $^2J$=13.6 Hz, $^3J_{9a5e}$=3.1 Hz, $^3J_{9a1e}$=1.8 Hz, $H_a^9$), 1.74 (dddd, $^2J$=$^3J_{6a7a}$=14.0 Hz, $^3J_{6a5e}$=6.2 Hz, $^3J_{6a7e}$=3.4 Hz, $H_a^6$), 1.84 (m, 1H, $^2J$=14.0 Hz, $H_e^6$), 1.87 (m, 1H, $H_e^5$); 2.02 (dddd, 1H, $^2J_{9e9a}$=13.6 Hz, $^3J_{9e5e}$=6.2 Hz, $^3J_{9e1e}$=3.6 Hz, $^4J_{9e6e}$=1.3 Hz, $H_e^9$), 2.39 (br.dq, 1H, $^3J_{8e,10}$=7.4 Hz, $^3J_{8e7a}$=7.2 Hz, $H_e^8$), 2.55 (dddd, 1H, $^2J$~$^3J_{7a6a}$=14.0 Hz, $^3J_{7a8e}$~$^3J_{7a6e}$=7.2 Hz, $H_a^7$),3.29 (d, 1H, $^2J$=12.8 Hz, H$^{12}$), 3.75 (br.dd, $^2J$=12.8 Hz, $^4J_{12',11}$=0.7 Hz, H$^{12}$), 3.79 (M, 1H, $^3J_{1e9e}$=3.6 Hz, $^3J_{1e9a}$=$^3J_{1e8e}$=1.8 Hz, $H_e^1$), 7.18 (m, 1H, H$^{16}$), 7.28 (m, 2H, H$^{15,15'}$), 7.41 (m, 2H, H$^{14,14'}$); $^{13}$C NMR (CDCl$_3$, 100 MHz) (δ): 19.18 (Me$^{10}$), 22.06 (Me$^{11}$), 23.38 (C$^6$H$_2$), 24.02 (C$^9$H$_2$), 27.17 (C$^7$H$_2$), 29.61 (C$^5$H), 32.98 (C$^8$H), 40.83 (C$^{12}$H$_2$), 80.32 (C$^1$H), 83.66 (C$^4$), 126.11(C$^{16}$H), 128.90 (2C$^{15}$H), 129.66 (2C$^{14}$H), 136.92(C$^{13}$). Isomer 12b: $^1$H NMR (CDCl$_3$, 400 MHz) (δ):1.025 (d, 3H, $^3J$=7.4 Hz, Me$^{10}$), 1.29 (br.dd, 1H, $^2J$=13.6 Hz, $^3J_{7e6e}$~6.0 Hz, $H_e^7$), 1.54 (d, 3H, $^4J_{11,12}$=0.7 Hz, Me$^{11}$), 1.64–1.82 (m, 4H, $H_e^5$+$H_e^6$+$H_a^6$+$H_a^9$), 2.20 (dddd, 1H, $^2J_{9e9a}$=13.4 Hz, $^3J_{9e5e}$=6.6 Hz, $^3J_{9e1e}$=3.9 Hz, $^4J_{9e6e}$=1.3 Hz, $H_e^9$), 2.37 (br.dq, 1H, $^3J_{8e,10}$=7.4 Hz, $^3J_{8e7a}$=6.8 Hz, H$_3^8$), 2.53 (dddd, 1H, $^2J$~$^3J_{7a6a}$=13.6 Hz, $^3J_{7a8e}$~$^3J_{7a6e}$=6.8 Hz, $H_a^7$), 2.97 (d, 1H, $^2J$=12.0 Hz, H$^{12}$), 3.09 (br.dd, $^2J$=12.0 Hz, $^4J_{12',11}$=0.7 Hz, H$^{12}$), 3.84 (ddd, 1H, $^3J_{1e9e}$=3.9 Hz, $^3J_{1e9a}$=$^3J_{1e8e}$=1.8 Hz, $H_e^1$), 7.19 (m, 1H, H$^{16}$), 7.28 (m, 2H, H$^{15,15'}$), 7.37 (m, 2H, H$^{14,14'}$). $^{13}$C NMR (CDCl$_3$, 100 MHz) (δ): 19.02 (Me$^{10}$), 21.96 (Me$^{11}$), 23.05 (C$^6$H$_2$), 24.05 (C$^9$H$_2$), 27.51 (C$^7$H$_2$), 31.14 (C$^5$H), 32.89 (C$^8$H), 40.78 (C$^{12}$H$_2$), 80.76 (C$^1$H), 83.65 (C$^4$), 126.29(C$^{16}$H), 128.97 (2C$^{15}$H), 129.62 (2C$^{14}$H), 136.86(C$^{13}$).

EXAMPLE 9

Synthesis of (1R,4R,5R,8R)-8-acetoxy-4,8-dimethyl-4-phenylthiomethyl-2,3-dioxabicyclo[3.3.1]nonane (13a), (1R,4S,5R,8R)-8-acetoxy-4,8-dimethyl-4-phenylthiomethyl-2,3-dioxabicyclo[3.3.1]nonane (13b), (1R,4R,5R,8R)-8-acetylacetoxy-4,8-dimethyl-4-phenylthiomethyl-2,3-dioxabicyclo[3.3.1]nonane (14a) and (1R,4S,5R,8R)-8-acetylacetoxy-4,8-dimethyl-4-phenylthiomethyl-2,3-dioxabicyclo[3.3.1]nonane (14b) (Scheme 5).

To a solution of sulfides 2a and 2b (1.15 g, 3.91 mmol, 2a/2b 55:45), pyridine (1.54 g, 19.5 mmol) and DMAP (49 mg, 0.4 mmol) in dry $CH_2Cl_2$ (30 mL) at 0° C. was added a solution of AcCl (1.22 g, 15.6 mmol) in $CH_2Cl_2$ (5 mL). The mixture was stirred for 1 h at 0° C. and for 12 h at rt The dark reaction mixture was poured into water (100 mL), extracted with hexane-EtOAc (7:3 mixture, 3×100 mL), dried (Na$_2$SO$_4$+NaHCO$_3$) and evaporated. The residue was separated by flash chromatography (gradient elution, hexane-EtOAc, 9:1→7:3) to give: (i) unreacted hydroxysulfides 2a and 2b (292 mg, 0.99 mmol, 25.4%); (ii) a mixture of diastereomers (1R,4R,5R,8R)-8-acetoxy-4,8-dimethyl-4-phenylthiomethyl-2,3-dioxabicylo[3.3.1]nonane 13a and (1R,4S,5R,8R)-8-acetoxy-4,8-dimethyl-4-phenylthiomethyl-2,3-dioxabicyclo[3.3.1]nonane 13b (518 mg, 1.54 mmol, 52.9% yield, 13a/13b ca. 55:45) as a colorless viscous liquid, R$_f$ 0.67 (hexane-EtOAc 7:3); (iii) a mixture of diastereomers (1R,4R,5R8R)-8-acetylacetoxy-4,8-dimethyl-4-phenylthiomethyl-2,3-dioxabicyclo[3.3.1]nonane 14a and (1R,4S,5R,8R)-8-acetylacetoxy-4,8-dimethyl-4-phenylthiomethyl-2,3-dioxabicyclo [3.3.1]nonane 14b (152 mg, 12.6% yield, 14a/14b ca. 54:46; keto/enol ca. 91:9) as a colorless oil, R$_f$ 0.40 (hexane-EtOAc 7:3); (iv) a mixture of diastereomers of E-enolacetates E-15a,b (48 mg, 0.105 mmol, 3.6% yield, E-15a/E-15b ca. 54:46) as a yellowish viscous oil, R$_f$ 0.61 (hexane-EtOAc 7:3); (v) a mixture of diastereomers of Z-enolacetates Z-15a,b (41 mg, 0.090 mmol, 3.1% yield, Z-15a/Z-15b ca. 52:48) as a yellowish viscous oil, R$_f$ 0.50 (hexane-EtOAc 7:3). Spectral data for 13a,b: IR (neat); 692, 742, 1022 v.s, 1054, 1204, 1223, 1254 v.s, 1371 v.s, 1453, 1732 v.s, 2935 cm$^{-1}$. $^1$H NMR (CDCl$_3$, 400 MHz) (δ): 1.24 (br.s, Me$^{11}$, 13a), 1.56 (br.s, Me$^{11}$, 13b), total 3H; 1.65 (s, Me$^{10}$, 13b), 1.66 (s, Me$^{10}$, 13a), total 3H; 1.67–1.89 (m, 3H, $H_e^6$+$H_a^6$+$H_a^9$, 13a+13b); 1.74 (m, $H_e^5$, 13b), 1.90 (dddd, $^3J_{5e6e}$=$^3J_{5e9e}$=6.6 Hz, $^3J_{5e6a}$=$^3J_{5e9a}$=3.3 Hz, $H_e^5$, 13a), total 1H; 2.07 (ddd, $^2J_{9e9a}$=14.1 Hz, $^3J_{9e5e}$=6.6 Hz, $^3J_{9e1e}$=3.4 Hz, $H_e^9$,13a), 2.27 (m, $H_e^9$, 13b), total 1H, 2.12–2.20 (m, 1H, $H_e^7$, 13a+13b); 2.25 (ddd, $^2J_{7a7e}$=15.0 Hz, $J_{7a6a}$=13.2 Hz, $^3J_{7a6e}$=6.0 Hz, $H_a^7$, 13b), 2.28 (ddd, $^2J_{7a7e}$=14.3 Hz, $J_{7a6a}$=13.3 Hz, $^3J_{7a6e}$=6.0 Hz, $H_a^7$, 13a), total 1H; 2.95 (H$^{12}$,13b)) and 3.02 ($^4J_{12,11}$=0.4 Hz, H$^{'12}$,13b), (ABq, $^2J$=12.0 Hz), 3.30 (d,$^2J$=12.8 Hz, H$^{12}$,13a) and 3.72 (dd, $^2J$=12.8 Hz, $^4J_{12,11}$= 0.5 Hz, H$^{'12}$,13a), total 2H;4.40 (dd, $^3J_{1e9e}$=3.4 Hz, $^3J_{1e9a}$= 1.0 Hz, H$^1$,13a), 4.44 (dd, $^3J_{1e9e}$=3.4 Hz, $^3J_{1e9a}$=0.8 Hz, H$^1$, 13B), total 1H; 7.17–7.23 (m, 1H, H$^{16}$,13a+13b); 7.29 (m, 2H, H$^{15}$, 13a+13b); 7.37 (m, 2H, H$^{14}$, 13a+13b). $^{13}$C NMR (CDCl$_3$, 100 MHz) (δ): Isomer 13a: 22.03 (Me$^{11}$), 22.42 (Me$^{10}$), 22.55 (Me$^{17}$C=O), 23.50 (C$^6$H$_2$), 23.97 (C$^9$H$_2$), 28.52 ($C^5H$), 32.88 ($C^7H_2$), 40.71 ($C^{12}H_2$), 77.46 ($C^1H$), 82.76 ($C^8$), 83.85 ($C^4$), 126.24 ($C^{16}H$), 128.91 ($2C^{14}H$), 129.76 ($2C^{15}H$), 136.73 ($C^{13}$), 170.13 (C=O); Isomer 13b: 21.77 ($Me^{11}$),22.53 ($Me^{10}$), 22.55 ($Me^{17}C$=O) 23.22 ($C^6H_2$), 24.09 ($C^9H_2$), 29.89($C^5H$), 33.20 ($C^7H_2$), 40.81 ($C^{12}H_2$), 77.91 ($C^1H$), 82.67 ($C^8$), 83.73 ($C^4$), 126.43 ($C^{16}H$), 128.96 ($2C^{14}H$), 129.73 ($2C^{15}H$), 136.29 ($C^{13}$), 170.13 (C=O). Spectral data for 14a,b: $^1H$ NMR (CDCl$_3$, 400 MHz) ($\delta$): 1.23 (br.s, $Me^{11}$, 14a), 1.55 (br.s, $Me^{11}$,14b), total 3H; 1.68 (s, $Me^{10}$,14b), 1.69 (s,$Me^{10}$,14a), total 3H; 1.70–1.93 (m, 4H); 2.08 (ddd, $^2J_{9e9a}$=14.0 Hz, $^3J_{9e5e}$=6.5 Hz, $^3J_{9e1e}$=3.5 Hz, $H_e^9$, 14), 2.15–2.33 (m), total 3H; 2.25 (s, $Me^{18}C$=O, 14a), 2.26 (s,$Me^{18}C$=O,14b), total 3H;2.95 ($H^{12}$, 14b) and 3.00 (br.,$H'^{12}$, 14b), (ABq, $^2J$=12.6 Hz),3.31 (d, $^2J$=12.8 Hz, $H^{12}$,14a) and 3.69 (br.d, $^2J$=12.8 Hz, $H^{12}$, 14a), total 2H;3.40 (s, $C^{17}H_2C$=O, 14a), 3.41 (s, $C^{17}H_2C$=O, 14b), total 2H; 4.37 (br.d, $^3J_{1e9e}$=3.5 Hz, $H_e^1$, 14a$_{keto}$), 4.41 (br.d, $^3J_{1e9e}$=3.6 Hz, $H_e^1$,14b$_{keto}$), 4.45 (br.d, $^3J_{1e9e}$=3.5 Hz, $H_e^1$, 14a$_{enol}$), 4.49 (br.d, $^3J_{1e9e}$=3.5 Hz, $H_e^1$, 14b$_{enol}$), total 1H; 4.92 (br.s, HC=, 14a$_{enol}$), 4.94 (br.s, HC=,14b$_{enol}$); 7.26–7.42 (m, 5H$_{arom.}$, 14a+14b); 1.205 (br.s, HO$_{enol}$, 14a+14b). $^{13}$C NMR (CDCl$_3$, 100 MHz) ($\delta$): Isomer 14a: 21.89 ($Me^{11}$), 22.48 ($Me^{10}$), 23.28 ($C^6H_2$), 23.74 ($C^9H_2$), 28.43 ($C^5H$), 30.15 ($Me^{18}C$=O),32.67 ($C^7H_2$), 40.59 ($C^{12}H_2$),51.18 ($C^{17}H_2$), 77.30 ($C^1H$), 83.76 ($C^4$), 84.25 ($C^8$), 90.60 ($HC^{17}=_{enol}$),126.16 ($^{16}CH$),128.83 ($2C^{14}H$), 129.65 ($2C^{15}H$), 136.62 ($C^{13}$), 165.83 ($OC^{20}$=O), 200.57 ($C^{19}$=O); Isomer 14b: 21.64 ($Me^{11}$),22.49 ($Me^{10}$), 22.98 ($C^6H_2$), 23.85 ($C^9H_2$), 29.74 ($C^5H$), 30.15 ($Me^{18}C$=O), 33.02 ($C^7H_2$), 40.75 ($C^{12}H_2$), 51.18 ($C^{17}H_2$), 77.72 ($C^1H$), 83.82 ($C^4$), 84.17 ($C^8$), 90.60 ($HC^{17}=_{enol}$), 126.37 ($C^{16}H$), 128.88 ($2C^{14}H$), 129.68 ($2C^{15}H$), 136.18 ($C^{13}$), 165.84 ($OC^{20}$=O), 200.57 ($C^{19}$=O).

EXAMPLE 10

Preparation of (1R,4R,5R,8R)-8-ethoxyoxalyloxy-4,8-dimethyl-4-phenylthiomethyl-2,3- dioxabicyclo [3.3.1] nonane (18a) and (1R,4S,5R,8R)-8-ethoxyoxalyloxy-4,8-dimethyl-4-phenylthiomethyl-2,3-dioxabicyclo [3.3.1] nonane (18b) (Scheme 6).

(a) To a solution of hydroxysulfides 2a,b (153 mg, 0.52 mmol) and 2,6-lutidine (155 mg, 1.45 mmol) in CH$_2$Cl$_2$ (3mL) at 0° C. was added neat TfOTMS (260 mg, 1.10 mmol) and the reaction mixture was stirred at 0° C. for 30 min, the temperature was raised to 20° C. After 30 min the reaction mixture was poured into the cold water (4° C., 30 mL) and extracted with EtOAc-hexane (1:4, 2×30 mL), washed with cold saturated NaHCO$_3$ (15 mL), dried (Na$_2$SO$_4$), and evaporated to give the crude TMS-derivative 16a,6 (16a/16b ca. 56:44) (204 mg, ca. quant. yield) as a mobile pale yellow liquid. IR(neat): 2954, 2928, 1453, 1446, 1372, 1250 v.s., 1125, 1060 v.s, 1040 v.s, 858 v.s, 840 v.s, 748, 739, 690 cm$^{-1}$. $^1H$ NMR (CDCl$_3$, 400 MHz): 0.108 and 0.111 (s, Me$_3$Si), total 9H; 1.22 (br.s, $Me^{11}$ 16a) and 1.53 (d, $Me^{11}$, $^4J$=0.5 Hz, 16b), total 3H; 1.38 (s, $Me^{10}$ 16b) and 1.39 (s, $Me^{10}$ 16a), total 3H; 1.60–1.65 (m, 1H, $H_e^7$ 16a+16b), 1.67–1.82 (m, 3H), 1.84 (dddd, $^3J_{5e9e}$=$^3J_{5e6e}$=6.0 Hz, $^3J_{5e9a}$=$^3J_{5e6a}$=3.0 Hz, $H_e^5$ 16a), 1.97–1.99 (m, 1H), 2.06 (ddd, $^2J$=13.0 Hz, $^3J_{9e5e}$=3.0 Hz, $^3J_{9a1e}$=2.5 Hz, $H_a^9$ 16a), 2.13–2.25 (m), total 2H; 2.945 and 3.015 ($^4J_{12,11}$=0.5 Hz) (ABq, $^2J$=12.0 Hz, $H^{12}$+$H^{12}$+$H'^{12}$ 16b), 3.32 (d, $^2J$=12.0 Hz, $H^{12}$ 16a) and 3.68 (dd, $^2J$=12.7 Hz, $^4J_{12',11}$=0.6 Hz, $H'^{12}$ 16a), total 12H; 3.59 (br.dd, $^3J_{1e9e}$=$^3J_{1e9a}$=2.5 Hz, $H_e^1$ 16a), 3.63 (m, $H_e^1$ 16b), total 1H; 7.26–7.42 (m, 5H).

(b) The mixture of TMS-derivative 16a,b (202 mg, ca. 0.52 mmol) and oxalyl chloride (3mL) was stirred at rt for 18 h, evaporated under vacuum for 3 h (0.2 mm Hg) to afford the crude chloride 17a,b (17a/17bca. 56:44) as a viscous pale brown oil. IR (neat): 2965, 2937, 1796 v.s, 1754 v.s, 1481, 1452, 1441, 1376, 1275 v.s, 1224, 1118, 1053, 1015 v.s, 977 v.s, 954, 823 v.s, 808, 741 v.s, and 692 cm$^{-1}$. $^1H$ NMR (CDCl$_3$, 250 MHz, $\delta$):1.26 (br.s, $Me^{11}$ 17a) and 1.58 (br.s, $Me^{11}$ 17b), total 3H; 1.78 (s, $Me^{10}$ 17b) and 1.79 (s, $Me^{10}$ 17a), total 3H; 1.68–2.02 (m, 4H), 2.15 (ddd, $^2J$=13.8 Hz, $^3J_{9e5e}$=6.6 Hz, $^3J_{9e1e}$=3.4 Hz, $H_e^9$ 17a), 2.30–2.44 (m), total 3H; 2.965 and 3.00 (br.) (ABq, $^2J$=12.1 Hz, $H^{12}$+$H'^{12}$ 17b), 3.33 (d, $^2J$=13.0 Hz, $H^{12}$ 17a) and 3.70 (dd, $^2J$=13.0 Hz, $^4J_{12',11}$=0.5 Hz, $H'^{12}$ 17a), total 2H; 4.28 (br.dd, $^3J_{1e9e}$=3.4 Hz, $^3J_{1e9a}$=1.0 Hz, $H_e^1$ 17a), 4.32 (br.dd, $^3J_{1e9e}$=3.4 Hz, $^3J_{1e9a}$=1.0 Hz, $H_e^1$ 17b), total 1H; 7.18–7.45 (m, 5H).

(c) To a solution of crude chloride 17a,b in CH$_2$Cl$_2$ (3 mL) at 0° C. was added a solution of EtOH (79 mg, 1.7 mmol) and 2,6-lutidine (214 mg, 2.0 mmol) in CH$_2$Cl$_2$ (2 mL) and the reaction mixture was stirred overnight at 4° C. The mixture was poured into cold water (50 mL), extracted with EtOAc-hexane (1:4, 2×50 mL), dried (Na$_2$SO$_4$) and evaporated. Flash chromatography (hexane-EtOAc, 85:15) of the residue gave the esters 18a,b (18a/18b ca. 57:43) (140 mg, 0.355 mmol, 68% yield) as a viscous pale yellow liquid, R$_f$ 0.41 (hexane-EtOAc, 4:1). IR(neat): 29.84, 2938, 1765 v.s, 1742 v.s, 1451, 1441, 1374, 1320 v.s, 1185 v.s, 1090, 1053, 1013 v.s, 741 v.s, 692 cm$^{-1}$. $^1H$ NMR (CDCl$_3$, 250 MHz, $\delta$): 1.26 (br.s, $Me^{11}$ 18a) and 1.57 (br.s, $Me^{11}$ 18b), total 3H; 1.373 (t, $^3J$=7.1 Hz, $Me^{18}CH_2$ 18a), 1.378 (t, $^3J$=7.1 Hz, $Me^{18}CH_2$ 18b), total 3H; 1.75 (s, $Me^{10}$ 18b) and 1.76 (s, $Me^{10}$ 18a), total 3H; 1.68–1.96 (m, 4H), 2.11 (ddd, $^2J$=13.6 Hz, $^3J_{9e5e}$=6.2 Hz, $^3J_{9e1e}$=3.4 Hz, $H_e^9$ 18a), 2.27–2.39 (m), total 3H; 2.96 and 3.015 (br.) (ABq, $^2J$=12.1 Hz, $H^{12}$+$H'^{12}$ 18b), 3.32 (d, $^2J$=12.9 Hz, $H^{12}$ 18a) and 3.71 (br.d, $^2J$=12..9 Hz, $H'^{12}$ 18a), total 2H; 4.325 (q, $^3J$=7.1 Hz, $C^{17}H_2O$ 18a), 4.331 (q, $^3J$=7.1 Hz, $C^{17}H_2O$ 18b), total 2H; 4.34 (m, $H_e^1$ 18a), 4.38 (m, $H_e^1$ 18b), total 1H; 7.17–7.44 (m, 5H).

EXAMPLE 11

Preparation of (1R,4R,5R,8R)-8-dibenzylaminooxalyloxy-4,8-dimethyl-4-phenylthiomethyl-2,3-dioxabicyclo[3.3.1]nonane (19a) and (1R,4S,5R,8R)-8-dibenzylaminooxalyloxy-4,8-dimethyl-4-phenylthiomethyl-2,3-dioxabicyclo[3.3.1]nonane (19b) (Scheme 6).

To a solution of chloride 17 a,b, prepared from hydroxysulfides 2a,b (112 mg, 0.38 mmol) as described above, in CH$_2$Cl$_2$ (3 mL) at 0° C. was added a solution of dibenzylamine (156 mg, 0.8 mmol) and 2,6-lutidine (160 mg, 1.5 mmol) in CH$_2$Cl$_2$ (2 mL). The mixture was stirred for 8 h at 0° C., poured into cold water (50 mL), extracted with hexane-EtOAc (3:1, 2×50 mL), organic layer was washed with saturated KHSO$_4$ (15 mL) and NaHCO$_3$ (15 mL), dried (Na$_2$SO$_4$) and evaporated. Flash chromatography (hexane-EtOAc, 85:15) of the residue gave the amides 19a,b (19a/19b ca. 59:41) (160 mg, 0.293 mmol, 77% yield based on the alcohols 2a,b) as a colorless oil, R$_f$ 0.38 (hexane-EtOAc, 4:1). IR (neat):1728 v.s, 1661 v.s, 1452 v.s, 1440 v.s, 1374, 1287, 1265, 1170 v.s, 1081, 1053, 1014 v.s, 738 v.s, 694 v.s. cm$^{-1}$. $^1H$ NMR (CDCl$_3$, 250 MHz, $\delta$): 1.24 (br.s, $Me^{11}$ 19a) and 1.57 (br.s, $Me^{11}$ 19b), total 3H; 1.71 (br.s, 3H, $Me^{10}$ 19a+19b), 1.62–1.90 (m, 4H), 2.06 (ddd, $^2J$=13.4 Hz, $^3J_{9e5e}$=6.2 Hz, $^3J_{9e1e}$=3.5 Hz, $H_e^9$ 19a), 2.18–2.42 (m), total 3H; 2.95 and 3.00 (br.) (ABq, $^2J$=12.1 Hz, $H^{12}$+$H'^{12}$ 19b), 3.32 (d, $^2J$=13.0 Hz, $H^{12}$ 19a) and 3.68 (br.d, $^2J$=13.0 Hz, $H'^{12}$ 19a), total 2H; 4.33 (br.d, $^3J_{1e9e}$=3.4 Hz, $H_e^1$ 19a) and 4.39 (m, $H_e^1$ 19b), total 1H; 4.38 (br.s, 2H, NC$^{17}H_2$), 4.52 (br.s, 2H, NC$^{18}H_2$), 7.22–7.41 (m, 15H).

EXAMPLE 12

Preparation of (1S,4S,5S,8S)-8-acetoxy-4,8-dimethyl-4 phenylthio-methyl-2,3-dioxabicyclo [3.3.1]nonane (13'a)

and (1S,4R,5S,8S)-8-acetoxy-4,8-dimethyl-4-phenylthiomethyl-2,3-dioxabicyclo[3.3.1]nonane (13'b) (Scheme 7).

To a neat TMS-derivative 16'a,b, prepared from 2'a,b (0.854 mmol, 252 mg) and TMSOTf as described in Example 9, was added AcCl (2.0 mL) and the mixture was stirred at rt for 50 h. The mixture was evaporated to give the crude acetoxysulfide 13'a,b (293 mg, 0.841 mmol, practically quantitative yield) as a pale yellow oil. $^1$H NMR spectrum of 13'a,b is consistent with that of 13a,b.

EXAMPLE 13

Preparation of (1R,4R,5R,8R)-4,8-dimethyl-4-phenylsulfonylmethyl-2,3-dioxabicyclo [3.3.1]nonan-8-ol (21a) and (1R,4S,5R,8R)-4,8-dimethyl-4-phenylsulfonylmethyl-2,3-dioxabicyclo[3.3.1]nonan-8-ol (21b) (Scheme 8).

To a solution of sulfides 2a and 2b (55/45) (2.10 g, 7.13 mmol) in EtOAc (40 mL) at rt was added a solution of MCPBA (5.12 g of ca. 60%, 17.8 mmol) in EtOAc (100 mL) and the reaction mixture was stirred for 8 h. Then it was diluted with hexane (140 mL), washed with saturated NaHCO$_3$ (2×100 mL), the combined water washings were extracted with EtOAc-hexane (1:1, 200 mL). The organic extract was dried (Na$_2$SO$_4$ and NaHCO$_3$), evaporated and the residue was chromatographed (hexane-EtOAc, 1:1) to afford a mixture of diastereomers 21a and 21b (2.129 g, 91% yield; 21a/21b ca. 55:45). The diastereomers were separated by MPLC (hexane-EtOAc, 1:1). Less polar isomer 21a, mp 112–113° C. (hexane-EtOAc, 5:1), R$_f$ 0.38 (EtOAc-hexane, 1:1). $^1$H NMR (400 MHz, CDCl$_3$, δ): 1.33 (s, 3H, Me$^{10}$), 1.49 (br.s, 3H, Me$^{11}$), 1.58 (ddd, 1H, $^2$J=14.2 Hz, $^3$J$_{7e6e}$=5.4 Hz, $^3$J$_{7e6a}$=0.9 Hz, H$_e^7$), 1.80–1.93 (m, 2H, H$_e^6$+H$_a^6$), 2.10 (ddd, 1H, $^2$J=13.9 Hz, $^3$J$_{9a5e}$=3.0 Hz, $^3$J$_{9a1e}$=2.0 Hz, H$_a^9$), 2.21 (ddd, 1H, $^2$J=13.9 Hz, $^3$J$_{9e5e}$=6.1 Hz, $^3$J$_{9e1e}$=3.5 Hz, H$_e^9$), 2.27 (m, 1H, H$_e^5$), 2.27 (ddd, 1H, $^2$J=14.2 Hz, $^3$J$_{7a6a}$=13.8 Hz, $^3$J$_{7a6e}$=6.6 Hz, H$_a^7$), 3.26 (d, 1H, $^2$J=14.3 Hz, H$^{12}$), 3.66 (dd, 1H, $^3$J$_{1e9e}$=3.5 Hz, $^3$J$_{1e9a}$=2.0 Hz, H$_e^1$), 4.21 (br.d, 1H, $^2$J=14.3 Hz, H'$^{12}$), 7.57 (dddd, 2H, $^3$J$_{15,14}$=$^3$J$_{15,16}$=7.4 Hz, $^4$J$_{1514'}$=$^4$J$_{15'14}$=1.3 Hz, H$^{15,15'}$), 7.65 (dddd, 1H, $^3$J$_{16,15}$=$^3$J$_{16,15'}$=7.4 Hz, $^4$J$_{1614}$=$^4$J$_{1614'}$=1.3 Hz, H$^{16}$), 7.93 (ddd, 2H, $^3$J$_{14,15}$=$^3$J$_{14,15'}$=7.4 Hz, $^4$J$_{14,16}$=1.3 Hz, H$^{14,14'}$); $^{13}$C NMR (100 MHz, CDCl$_3$, δ):22.87 (Me$^{11}$), 23.45 (C$^6$H$_2$), 24.64 (C$^9$H$_2$), 27.97 (Me$^{10}$), 30.05 (C$^5$H), 35.70 (C$^7$H$_2$), 61.02 (C$^{12}$H$_2$), 71.30 (C$^8$), 81.96 (C$^1$H), 82.71 (C$^4$), 127.51 (2C$^{14'}$H), 129.33 (2C$^{15}$H), 133.71 (C$^{16}$H), 141.08 (C$^{13}$). Anal. Calcd for C$_{16}$H$_{22}$O$_5$S: C, 58.87; H, 6.79; S, 9.82. Found: C, 58.87; H, 6.84; S, 9.73. More polar isomer 21b: a colorless oil R$_f$ 0.34 (EtOAc-hexane, 1:1). $^1$H NMR (400 MHz, CDCl$_3$, δ): 1.28 (s, 3H, Me$^1$), 1.58 (br.dd, 1H, $^2$J=14.0 Hz, $^3$J$_{7e6e}$=5.2 Hz, H$_e^7$), 1.70 (br.s, 1H, OH), 1.79 (br.s, 3H, Me$^{11}$), 1.85–1.99 (m, 2H, H$_e^6$+H$_a^6$), 2.03 (ddd, 1H, $^2$J=13.4 Hz, $^3$J$_{9a5e}$=3.2 Hz, $^3$J$_{9a1e}$=1.7 Hz, H$_a^9$), 2.08 (dddd, 1H, $^3$J$_{5e6e}$=$^3$J$_{5e9e}$=6.2 Hz, $^3$J$_{5e6a}$=$^3$J$_{5e9a}$=3.2 Hz, H$_e^5$), 2.12 (ddd, 1H, $^2$J=$^3$J$_{7a6a}$=14.0 Hz, $^3$J$_{7a6e}$=6.7 Hz, H$_a^7$), 2.26 (ddd, 1H, $^2$J=13.4 Hz, $^3$J$_{9e5e}$=6.2 Hz, $^3$J$_{9e1e}$=3.3 Hz, H$_e^9$), 3.14 (d, 1H, $^2$J=14.0 Hz, H$^{12}$), 3.33 (br.d, 1H, $^2$J=14.0 Hz, H'$^{12}$), 3.68 (dd, 1H, $^3$J$_{1e9e}$=3.3 Hz, $^3$J$_{1e9a}$=1.7 Hz, H$_e^1$), 7.56 (dddd, 2H, $^3$J$_{15,14}$=$^3$J$_{15,16}$=7.4 Hz, $^4$J$_{1515'}$=$^4$J$_{15'14}$=1.4 Hz, H$^{15,15'}$), 7.66 (dddd, 1H, $^3$J$_{16,15}$=$^3$J$_{16,15'}$=7.4 Hz, $^4$J$_{1614}$=$^4$J$_{1614'}$=1.4 Hz, H$^{16}$), 7.92 (ddd, 2H, $^3$J$_{14,15}$=$^3$J$_{14,15'}$=$^3$J$_{14',15'}$=7.4 Hz, $^4$J$_{14,16}$=1.3 Hz, H$^{14,14'}$); $^{13}$C NMR (100 MHz, CDCl$_3$, δ):21.84 (Me$^{11}$), 23.57 (C$^9$H$_2$), 23.85 (C$^6$H$_2$), 28.01 (Me$^{10}$), 31.53 (C$^5$H), 35.54 (C$^7$H$_2$), 60.55 (C$^{12}$H$_2$), 71.19 (C$^8$), 82.45 (C$^1$H), 82.94 (C$^4$), 127.62 (2C$^{14}$H), 129.33 (2C$^{15}$H), 133.83 (C$^{16}$H), 141.21 (C$^{13}$).

EXAMPLE 14

Preparation of (1R,4R,5R,8S)-4,8-dimethyl-4-phenylsulfonylmethyl-2,3-dioxabicyclo[3.3.1]nonane (22a) and (1R,4S,5R,8S)-4,8-dimethyl-4-phenylsulfonylmethyl-2,3-dioxabicyclo[3.3.1]nonane (22b) (Scheme 8).

To a solution of sulfides 11 a,b (18.0 mg, 0.065 mmol, 11a/11b 54:46) in EtOAc (0.5 mL) was added MCPBA (52 mg of ca. 60%, 0.18 mmol) and the mixture was stirred for 8 h at rt The mixture was poured into saturated NaHCO$_3$ (10 mL), extracted with hexane-EtOAc (7:3, 40 mL), organic extract was washed with saturated NaHCO$_3$ (10 mL0 and the water washings were extracted with hexane-EtOAc (7:3, 30 mL). The combined organic layer was dried (Na$_2$SO$_4$+ NaHCO$_3$) and evaporated. Flash chromatography (hexane-EtOAc, 80:20) afforded a mixture of diastereomeric sulfones 22 a,b (18.0 mg, 90% yield, ratio 22a/22b ca. 55:45). The sulfones were separated by semi-preparative DP HPLC (column-LiChrospher® Si 60 (10 μm) 250–10; eluent i-PrOH-hexane 2:98). Less polar isomer 22 a, colorless semisolid, τ$_R$ 16.7 min (column-LiChrospher® Si 60 (5 μm) 250–4; eluent EtOAc-hexane 12:88). $^1$H NMR (CDCl$_3$, 250 MHz) (δ): 1.09 (d, 3H, $^3$J=6.4 Hz, Me$^{10}$), 1.53 (br.s, 3H, Me$^{11}$),1.58(ddd, 1H, $^2$J=13.4 Hz, $^3$J$_{9a5e}$=3.0 Hz, $^3$J$_{9a1e}$=1.7 Hz, H$_a^9$), 1.64–2.13 (m, 5H, H$_e^6$+H$_a^6$+H$_e^7$+H$_a^8$), 2.36 (br.dddd, 1H, $^3$J$_{5e9e}$=$^3$J$_{5e6e}$=6.0 Hz, $^3$J$_{5e9a}$=$^3$J$_{5e6a}$=3.0 Hz, H$_e^5$), 2.48 (br.ddd, 1H, $^2$J$_{9e9a}$=13.4 Hz, $^3$J$_{9e5e}$=6.0 Hz, $^3$J$_{9e1e}$=3.6 Hz, H$_e^9$), 3.25 (d, 1H, $^2$J=14.3 Hz, H$^{12}$), 3.86 (br.dd, 1H, $^3$J$_{1e9e}$=3.6 Hz, $^3$J$_{1e9a}$=1.7 Hz, H$_e^1$), 4.31 (br.dd, 1H, $^2$J=14.3 Hz, $^4$J=0.6 Hz, H'$^{12}$), 7.60 (m, 2H, H$^{15,15'}$), 7.66 (m, 1H, H$^{16}$), 7.97 (m, 2H, H$^{14,14'}$); DCI HRMS obsd 311.12940, calcd for C$_{16}$H$_{23}$O$_4$S (M+H) 311.13171. More polar isomer 22b, colorless solid, mp 129–130° C., τ$_R$ 17.7 min. (column-LiChrospher® Si 60 (5μm) 250–4; eluent EtOAc-hexane 12:88). $^1$H NMR (CDCl$_3$, 400 MHz) (δ): 1.01 (d, 3H, $^3$J=6.4 Hz, Me$^{10}$), 1.46 (ddd, 1H, $^2$J=13.3 Hz, $^3$J$_{9a5e}$=3.1 Hz, $^3$J$_{9a1e}$=2.0 Hz, H$_a^9$), 1.65 (m, 1H), 1.68–1.82 (m, 3H, H$_e^6$+H$_a^6$+H$_e^7$+H$_a^7$); 1.80 (d, 3H, $^4$J$_{11,12'}$=0.5 Hz, Me$^{11}$), 2.07–2.14 (m, 2H, H$_e^5$+H$_a^8$), 2.47 (dddd, 1H, $^2$J$_{9e9a}$=13.3 Hz, $^3$J$_{9e1e}$=4.4 Hz, $^3$J$_{9e5e}$=$^4$J$_{9e6e}$=3.2 Hz, H$_e^9$), 3.14 (d, 1H, $^2$J=14.0 Hz, H$^{12}$), 3.37 (br.dd, 1H, $^2$J=14.0 Hz, $^4$J$_{12'11}$=0.5 Hz, H'$^{12}$), 3.85 (br.dd, 1H, $^3$J$_{1e9e}$=4.4 Hz, $^3$J$_{1e9a}$=2.0 Hz, H$_e^1$), 7.57 (m, 2H, H$^{15,15'}$), 7.66 (m, 1H, H$^{16}$), 7.93 (m, 2H, H$^{14,14'}$); $^{13}$C NMR (100 MHz, CDCl$_3$, δ): 18.49 (Me$^{10}$), 22.06(Me$^{11}$), 27.33 (CH$_2$), 28.96 (CH$_2$), 29.61 (C$^7$H$_2$), 31.56 (C$^5$H), 35.53 (C$^8$H), 60.60 (C$^{12}$H$_2$), 80.06 (C$^1$H), 82.53 (C$^4$), 127.64 (2C$^{14}$H), 129.32 (2C$^{15}$H), 133.76 (C$^{16}$H), 141.37 (C$^{13}$). CI HRMS (CH$_4$) obsd 311.12650, calcd for C$_{16}$H$_{23}$O$_4$S (M+H)311.13171.

EXAMPLE 15

Prerparation of (1R,4R,5R,8R)-8-acetoxy-4,8-dimethyl-4-phenylsulfonylmethyl-2,3-dioxabicyclo [3.3.1]nonane (23a) and (1R,4S,5R,8R)-8-acetoxy-4,8-dimethyl-4-phenylsulfonylmethyl-2,3-dioxabicyclo[3.3.1]nonane (23b) (Scheme 8).

To a solution of sulfides 13a and 13b (55/45) (55 mg, 0.163 mmol) in EtOAc (1 mL) at 0° C. was added a solution of MCPBA (103 mg of ~60%, 0.35 mmol) in EtOAc (1.5 ml) and the reaction mixture was stirred for 4 h at rt The reaction mixture was poured into saturated NaHCO$_3$ (10 mL), extracted with EtOAc-hexane (1:2, 2×30 mL). The organic extract was dried (Na$_s$SO$_4$ and NaHCO$_3$), evaporated and the residue was separated by MPLC (hexane-EtOAc, 7:3) to give the sulfones 23a (31 mg) and 23b (26 mg) (total yield 97%). Less polar isomer 23a, mp 96–98° C., R$_f$ 0.37 (hexane-benzene-EtOAc 11:6:3). $^1$H NMR (400 MHz, CDCl$_3$, δ): 1.51 (br.s, 3H, Me$^{11}$), 1.62 (s, 3H, Me$^{10}$), 1.78 (dddd, 1H, $^2$J=14.5 Hz, $^3$J$_{6a7a}$=13.4 Hz, $^3$J$_{6a7e}$=6.8 Hz, $^3$J$_{6a5e}$=3.4 Hz, H$_a^6$), 1.88 (ddd, 1H, $^2$J=14.0 Hz, $^3$J$_{9a5e}$=3.4 Hz, $^3$J$_{9a1e}$=1.2 Hz, H$_a^9$), 1.90 (dddd, 1H, $^2$J=14.5 Hz, $^3J_{6e5e}$ 6.8 Hz, $^3J_{6e7e}=^3J_{6e7a}=2.8$ Hz, $H_e^6$), 2.01 (s, 3H, Me$^{17}$CO), 2.14 (m, 1H, $H_e^7$), 2.19 (m, 1H, $H_a^7$), 2.26 (ddd, 1H, $^2J=14.0$ Hz, $^3J_{9e5e}=6.5$ Hz, $^3J_{9e1e}=3.2$ Hz, $H_e^9$), 2.30 (br.dddd, 1H, $^3J_{5e9e}=^3J_{5e6e}=6.8$ Hz, $^3J_{5e9a}^3J_{5e6a}=3.4$ Hz, $H_e^5$), 3.25 (d, 1H, $^2J=14.3$ Hz, H$^{12}$), 4.22 (dd, 1H, $^2J=14.3$ Hz, $^4J_{12',11}=0.4$ Hz, H'$^{12}$), 4.45 (br.dd, $^3J_{1e9e}=3.2$ Hz, J$_{1e9a}=$ 1.2 Hz, $H_e^1$), 7.58 (m, 2H, H$^{15,15'}$), 7.66 (m, 1H, H$^{16}$), 7.94 (m, 2H, H$^{14,14'}$). $^{13}$C NMR (100 MHz, CDCl$_3$, δ): 22.42 (Me$^{17}$CO), 22.49 (Me$^{10}$), 23.09 (Me$^{11}$), 23.39 (C$^6$H$_2$), 24.52 (C$^9$H$_2$), 29.42 (C$^5$H), 33.26 (C$^7$H$_2$), 60.98 (C$^{12}$H$_2$), 77.80 (C$^1$H), 82.54 (C$^8$), 8.272 (C$^4$), 127.52 (2C$^{14}$H), 129.35 (2C$^{15}$H), 133.75 (C$^{16}$H), 141.08 (C$^{13}$), 170.20 (C=O). HRMS (CI, CH$_4$): obsd 369.13300, calcd for C$_{18}$H$_{25}$O$_6$S (M+1) 369.13719. Anal. Calcd for C$_{18}$H$_{24}$O$_6$S: C, 58.68; H, 6.56; S, 8.70. Found: C, 58.64; H, 6.55; S, 8.34. More polar isomer 23b, a colorless solid, mp 101–102° C., R$_f$ 0.31 (hexane-benzene-EtOAc 11:6:3). $^1$H NMR (400 MHz, CDCl$_3$, δ):1.56 (s, 3H, Me$^{10}$), 1.79 (ddd, 1H, $^2J=13.6$ Hz, $^3J_{9a5e}=3.4$ Hz, $^3J_{9a1e}=1.4$ Hz, $H_a^9$), 1.80 (br.s, 3H, Me$^{11}$), 1.84 (dddd, 1H, $^2J=14.0$ Hz, $^3J_{6a7a}=14.0$ Hz, $^3J_{6a7e}=6.0$ Hz, $^3J_{6a5e}=3.4$ Hz, $H_a^6$), 1.96 (m, 1H, $H_e^6$), 2.00 (s, 3H, Me$^{17}$CO), 2.04 (m, 1H, $H_a^7$), 2.10 (dddd, 1H, $^3J_{5e9e}=^3J_{5e6e}=6.8$ Hz, $^3J_{5e9a}=^3J_{5e6a}=3.4$ Hz, $H_e^5$), 2.16 (br.dd, 1H, $^2J=14.5$ Hz, $^3J_{7e6e}=6.0$ Hz, $H_e^7$), 2.29 (ddd, 1H, $^2J=13.6$ Hz, $^3J_{9e5e}=6.8$ Hz, $^3J_{9e1e}=3.6$ Hz, $H_e^9$), 3.12 (d, 1H, $^2J=14.0$ Hz, H$^{12}$), 3.32 (br.d, 1H, $^2J=14.0$ Hz, H'$^{12}$), 4.42 (br.d, $^3J_{1e9e}=3.6$ Hz, J$_{1e9a}=1.4$ Hz, $H_e^1$), 7.57 (m, 2H, H$^{15,15'}$), 7.66 (m, 1H, H$^{16}$), 7.92 (m, 2H, H$^{14,14'}$); $^{13}$C NMR (100 MHz, CDCl$_3$, δ): 21.94 (Me$^{11}$), 22.43 (Me$^{17}$CO), 22.53 (Me$^{10}$), 23.40 (C$^9$H$_2$), 23.78 (C$^6$H$_2$), 30.92 (C$^5$H), 32.92 (C$^7$H$_2$), 60.50 (C$^{12}$H$_2$), 78.45 (C$^1$H), 82.35 (C$^8$), 82.97 (C$^4$), 127.61 (2C$^{14}$H), 129.37 (2C$^{15}$H), 133.89 (C$^{16}$H), 141.15 (C$^{13}$), 170.16 (C=O). Anal. Calcd for C$_{18}$H$_{24}$O$_6$S: C, 58.68; H, 6.56; S, 8.70 Found: C, 58.72; H, 6.57; S, 8.51.

EXAMPLE 16

Preparation of (1R,4R,5R,8R)-8-acetylacetoxy-4,8-dimethyl-4-phenylsulfonylmethyl-2,3-dioxabicyclo[3.3.1]nonane (24a) and (1R,4S,5R,8R)-8-acetylacetoxy-4,8-dimethyl-4-phenylsulfonylmethyl-2,3-dioxabicyclo [3.3.1] nonane (24b) (Scheme 8).

To a solution of sulfides 14a and 14b (55/45) (130 mg, 0.34 mmol) in EtOAc (6 mL) at 0° C. was added MCPBA (276 mg of ca. 60%, 0.96 mmol) and the mixture was stirred for 6 hr at rt The reaction mixture was poured into saturated NaHCO$_3$ (20 mL), extracted with EtOAc-hexane (2:3, 3×25 mL). The organic extract was dried (Na$_2$SO$_4$ and NaHCO$_3$), evaporated and the residue was purified by flash chromatography (hexane-EtOAc, 3:2) to afford a mixture of diastereomeric 24a and 24b (94 mg, total yield 66.7%, 24a/24b ca. 55:45). The sulfones were separated by MPLC (hexane-EtOAc, 3:2). Less polar isomer 24a, colorless oil. $^1$H NMR (400 MHz, CDCl$_3$, δ): 1.52 (br.s, 3H, Me$^{11}$), 1.66 (s, 3H, Me$^{10}$), 1.80 (dddd, 1H, $^2J=14.0$ Hz, $^3J_{6a7a}=13.7$ Hz, $^3J_{6a7e}=$ 6.5 Hz, $^3J_{6a5e}=3.4$ Hz, $H_a^6$), 1.91 (m, 1H, $H_a^9$), 1.93 (m, 1H, $H_e^6$), 2.15–2.25 (m, 2H, $H_e^7+H_a^7$), 2.26 (s, 3H, Me$^{18}$C=O), 2.28 (ddd, 1H, $^2J=13.0$ Hz, $^3J_{9e5e}=6.4$ Hz, $^3J_{9e1e}=3.6$ Hz, $H_e^9$), 2.31 (dddd, 1H, $^3J_{5e9e}=6.4$ Hz, $^3J_{5e9a}=^3J_{5e6a}=3.2$ Hz, $H_e^5$), 3.27 (d, 1H, $^2J=14.4$Hz, H$^{12}$), 3.242 (s, ca. 2H, C$^{17}$H$_2$CO$_{keto\ form}$), 4.20 (br.d, ca. 1H, $^2J=14.4$ Hz, H'$^{12}_{keto}$), 4.23 (br.d, $^2J=14.0$ Hz, H'$^{12}_{enol}$), total 1H; 4.43 (br.d, ca. 1H, $^3J_{1e9e}=3.6$ Hz, $H_e^9{}_{keto}$), 4.50 (br.d, $^3J_{1e9e}=4.0$ Hz, $H_e^9{}_{enol}$), total 1H; 4.94 (br.s, HC=$_{enol}$), 7.58 (m, 2H, H$^{15,15'}$), 7.67 (m, 1H, H$^{16}$), 7.94 (m, 2H, H$^{14,14'}$), 12.05 (br.s, HO$_{enol}$) (ratio keto/enol ca. 93:7 in ca. 2% solution in CDCl$_3$). $^{13}$C NMR (100 MHz, CDCl$_3$, δ): 22.53 (Me$^{10}$), 23.01 (Me$^{11}$), 23.27 (C$^6$H$_2$), 24.39 (C$^9$H$_2$), 29.39 (C$^5$H), 30.28 (Me$^{18}$CO), 33.13 (C$^7$H$_2$), 51.29 (C$^{17}$H$_2$), 60.95 (C$^{12}$H$_2$), 77.73 (C$^1$H), 82.75 (C$^4$), 84.17 (C$^8$), 127.53 (2C$^{14}$H), 129.36 (2C$^{15}$H), 133.76 (C$^{16}$H), 141.05 (C$^{13}$), 165.99 (OC$^{20}$=O), 200.48 (MeC$^{19}$=O). HRMS (CI, CH$_4$): obsd 411.15100, calcd for C$_{20}$H$_{27}$O$_7$S (M+1) 411.14775; obsd 439.17800, calcd for C$_{22}$H$_{31}$O$_7$S (M+29) 439.17905. More polar isomer 24b, colorless oil. $^1$H NMR (400 MHz, CDCl$_3$, δ): 1.60 (s, 3H, Me$^{10}$), 1.80 (br.s, 3H, Me$^{11}$),1.81–1.88 (m, 2H, $H_a^6+H_a^9$), 1.93 (d, $^4J=0.4$ Hz, Me$^{18}$C=$_{enol}$), 1.95 (m, 1H, $H_e^6$), 2.07 (ddd, 1H, $^2J=^3J_{7a6a}=$ 14.5 Hz, $^3J_{7a6e}=6.0$ Hz, $H_a^7$), 2.10 (dddd, 1H, $^3J_{5e9e}=^3J_{5e6e}=$ 6.8 Hz, $^3J_{5e9a}=^3J_{5e6a}=3.4$ Hz, $H_e^5$), 2.18 (ddd, 1H, $^2J=14.5$ Hz, $^3J_{7e6e}=6.0$ Hz, $H_e^7$), 2.25 (s, 3H, Me$^{18}$C=O), 2.30 (br.ddd, 1H, $^2J=13.8$ Hz, $^3J_{9e5e}=6.8$ Hz, $^3J_{9e1e}=3.6$ Hz, $H_e^9$), 3.13 (d, 1H, $^2J=14.0$ Hz, H$^{12}$), 3.32 (dd, ca. 1H, $^2J=14.0$ Hz, $^4J_{12',11}=0.3$ Hz, H'$^{12}_{keto}$), 3.33 (br.d, $^2J=14.0$ Hz, H'$^{12}_{enol}$), total 1H; 3.41 (s, ca. 2H, C$^{17}$H$_2$CO$_{keto\ form}$), 4.39 (br.d, ca. 1H, $^3J_{1e9e}=3.6$ Hz, $H_e^9{}_{keto}$), 4.49 (br.d, $^3J_{1e9e}=3.8$ Hz, $H_e^9{}_{enol}$), total 1H; 4.93 (br.s, HC=$_{enol}$), 7.58 (m, 2H, 2H$^{15}$), 7.66 (m, 1H, H$^{16}$), 7.92 (m, 2H, 2H$^{14}$), 12.04 (br.s, HO$_{enol}$) (ratio keto/enol ca. 95:5 in ca. 2% solution in CDCl$_3$). $^{13}$C NMR (63 MHz, CDCl$_3$, δ): 21.89 (Me$^{11}$), 22.56 (Me$^{10}$), 23.25 (C$^9$H$_2$), 23.65 (C$^6$H$_2$), 30.30 (Me$^{18}$CO), 30.84 (C$^5$H), 32.82 (C$^7$H$_2$), 51.29 (C$^{17}$H$_2$), 60.51 (C$^{12}$H$_2$), 78.35 (C$^1$H), 83.03 (C$^4$), 83.97 (C$^8$), 127.62 (2C$^{14}$H), 129.38 (2C$^{15}$H), 133.91 (C$^{16}$H), 141.12 (C$^{13}$), 165.95 (OC$^{20}$=O), 200.58 (MeC$^{19}$=O). DCI HRMS: obsd 411.14210, calcd for C$_{20}$H$_{27}$O$_7$S (M+1)411.14775.

EXAMPLE 17

Preparation of (1R,4R,5R,8R)-8-ethoxyoxyalyloxy-4,8-dimethyl-4-phenylsulfonylmethyl-2,3-dioxabicyclo [3.3.1] nonane (25a) and (1R,4S,5R,8R)-8-ethoxyoxyalyloxy-4,8-dimethyl-4-phenylsulfonylmethyl-2,3-dioxabicyclo [3.3.1] nonane (25b) (Scheme 8).

To a solution of sulfides 18a,b (118 mg, 0.30 mmol) in EtOAc (4 mL) at 5° C. was added a solution of MCPBA (216 mg of ca. 60%, 0.75 mmol) in EtOAc (3 mL). The mixture was stirred for 5 h at rt, poured into saturated Na HCO$_3$ (30 mL) and extracted with hexane-EtOAc (3:1, 3×40 mL). Organic extract was dried (Na$_2$SO$_4$) and evaporated. Flash chromatography (hexane-EtOAc, 75:25) of the residue gave a mixture of diastereomeric sulfones 25a,b (120 mg, 94% yield, 25a/25b ca. 57:43) as a colorless oil. The sulfones were separated by MPLC (hexane-EtOAc 75:25). Less polar isomer 25a, a colorless oil. IR (neat): 2987, 2940, 1767 v.s, 1737 v.s, 1448 v.s, 13.76 v.s, 1310, 1187 v.s, 1152 v.s, 1095 v.s, 1086 v.s, 1013 v.s, 751,724 v.s, 690 cm$^{-1}$. $^1$H NMR (CDCl$_3$, 400 MHz, δ): 1.37 (t, 3H, $^3J=7.1$ Hz, Me$^{18}$CH$_2$), 1.53 (br.s, 3H, Me$^{11}$), 1.72 (s, 3H, Me$^{10}$), 1.82 (dddd, 1H, $^2J=14.2$ Hz, $^3J_{6a7a}=13.2$ Hz, $^3J_{6a7e}=6.8$ Hz, $^3J_{6a5e}=3.5$ Hz, $H_a^6$), 1.94 (ddddd, 1H, $^2J=14.2$ Hz, $^3J_{6e7e}=5.2$ Hz, $^3J_{6e7a}=$ $^3J_{6e5e}=^4J_{6e9e}=2.6$ Hz, $H_e^6$), 1.97 (ddd, 1H, $^2J=14.0$ Hz, $^3J_{9a5e}=2.6$ Hz, $^3J_{9a1e}=1.4$ Hz, $H_a^9$), 2.24–2.37 (m, 4H, $H_e^5+H_e^7+H_a^7+H_3^9$), 3.27 (d, 1H, $^2J=14.3$ Hz, H$^{12}$), 4.21 (br.d, 1H, $^2J=14.3$ Hz, H'$^{12}$), 4.33 (q, 2H, $^3J=7.1$ Hz, C$^{17}$H$_2$O), 4.36 (br.dd, 1H, $^eJ_{1e9e}=3.6$ Hz, $^3J_{1e9a}=1.4$ Hz, $H_e^1$), 7.59 (m, 2H, 2H$^{15}$), 7.67 (m, 1H, H$^{16}$), 7.94 (m, 2H, 2H$^{14}$). $^{13}$C NMR (100 MHz, CDCl$_3$, δ):13.92 (me$^{18}$CH$_2$), 22.34 (Me$^{10}$), 23.05 (Me$^{11}$), 23.23 (C$^6$H$_2$), 24.46 (C$^9$H$_2$), 29.32 (C$^5$H), 32.49 (C$^7$H$_2$), 60.96 (C$^{12}$H$_2$), 63.03 (C$^{17}$H$_2$), 77.74 (C$^1$H), 82.91 (C$^4$), 86.58 (C$^8$), 127.57 (2C$^{14}$H), 129.41 (2C$^{15}$H), 133.83 (C$^{16}$H), 141.03(C$^{13}$), 156.66 (C=O), 158.08 (C=O). Anal. Calcd for C$_{20}$H$_{26}$O$_8$S: S, 7.52. Found: S, 7.13. More polar isomer 25b, a colorless oil. IR (neat): 1763 v.s, 1740 v.s, 1448, 1376, 1322 v.s, 1197 v.s, 1181 v.s, 1154 v.s, 1087, 1014 v.s, 734 v.s, 690 cm$^{-1}$. $^1$H NMR (400 MHz, CDCl$_3$, δ): 1.36 (t, 3H, $^3J=7.1$ Hz, Me$^{18}$CH$_2$), 1.66 (s, 3H, Me$^{10}$), 1.80–1.89 (m, 1H, H$_a^6$), 1.82 (br.s, 3H, Me$^{11}$), 1.88 (ddd, 1H, $^2J$=14.2 Hz, $^3J_{9a5e}$=3.4 Hz, $^3J_{9a1e}$=1.8 Hz, H$_a^9$), 1.99 (m, 1H, H$_e^6$), 2.13 (m, 1H, H$_e^5$), 2.14 (ddd, 1H, $^2J$=$^3J_{7a6a}$=14.6 Hz, $^3J_{7a6e}$=2.0 Hz, H$_a^7$), 2.33 (br.dd, 1H, $^2J$=14.6 Hz, $^3J_{7e6e}$=6.2 Hz, H$_e^7$), 2.34 (ddd, 1H, $^2J$=14.2 Hz, $^3J_{9e5e}$=6.4 Hz, $^3J_{9e1e}$=3.6 Hz, H$_e^9$), 3.12 (d, 1H, $^2J$=14.0 Hz, H$^{12}$), 3.32 (br.d, 1H, $^2J$=14.0 Hz, H'$^{12}$), 4.32 (q, 2H, $^3J$=7.1 Hz, C$^{17}$H$_2$O), 4.34 (m, 1H, H$_e^1$), 7.57 (m, 2H, H$^{15, 15'}$), 7.67 (m, 1H, H$^{16}$), 7.92 (m, 2H, H$^{14, 14'}$); $^{13}$C NMR (63 MHz, CDCl$_3$, δ): 13.87 (Me$^{18}$), 21.87 (Me$^{11}$), 22.29 (Me$^{10}$), 23.30 (C$^9$H$_2$), 23.53 (C$^6$H$_2$), 30.70 (C$^5$H), 32.14 (C$^7$H$_2$), 60.41 (C$^{12}$H$_2$), 63.01 (C$^{17}$H$_2$O), 78.26 (C$^1$H), 83.12 (C$^4$), 86.31 (C$^8$), 127.58 (2C$^{14}$H), 129.37 (2C$^{15}$H), 133.92 (C$^{16}$H), 141.02 (C$^{13}$), 156.56 (C=O), 158.00 (C=O).

EXAMPLE 18

Preparation of (1R,4R,5R,8R)-8-dibenzylaminooxalyloxy-4,8-dimethyl-4-phenylsulfonylmethyl-2,3-dioxabicyclo[3.3.1]nonane (26a) and (1R,4S,5R,8R)-dibenzylaminooxalyloxy-4,8-dimethyl-4-phenylsulfonylmethyl-2,3-dioxabicyclo[3.3.1]nonane (26b) (Scheme 8).

To a solution of sulfides 19 a,b (137 mg, 0.25 mmol) in EtOAc (5 mL) was added a solution of MCPBA (201 mg of ca. 60%, 0.7 mmol) in EtOAc (2 mL). The mixture was stirred for 5 h at rt, poured into saturated NaHCO$_3$ (30 mL) and extracted with hexane-EtOAc (1:1, 3×50 mL). The organic extract was dried (Na$_2$SO$_4$) and evaporated. Flash chromatography (hexane-EtOAc, 75:25) of the residue afforded the diastereomers 26a,b (143.5 mg, 99% yield, 26a/26b ca. 60:40) as a colorliess oil. The sulfones were separated by MPLC (hexane-EtOAc, 70:30). Less polar isomer 26a, a colorless glass; IR (neat): 1736 v.s, 1670 v.s, 1653 v.s, 1496, 1453 v.s, 1377, 1318 v.s, 1272, 1181 v.s, 1171 v.s, 1150 v.s, 1083 v.s, 1013, 912, 723 v.s, 700 v.s, 690 v.s. cm$^{-1}$. $^1$H NMR (CDCl$_3$, 400 MHz, δ): 1.50 (br.s, 3H, Me$^{11}$), 1.67 (s, 3H, Me$^{10}$), 1.72 (m, 1H, H$_a^6$), 1.82–1.92 (m, 2H, H$_e^6$+H$_a^9$), 2.18–2.28 (m, 4H, H$_e^5$+H$_e^7$+H$_a^7$+H$_e^9$), 3.27 (d, 1H, $^2J$=14.3 Hz, H$^{12}$), 4.17 (br.d, 1H, $^2J$=14.3 Hz, H'$^{12}$), 4.35 (br.s, 2H, NC$^{17}$H$_2$), 4.36 (m, 1H, H$_e^1$), 4.50 (br.s, 2H, NC$^{18}$H$_2$), 7.19–7.26 (m, 4H), 7.31–7.41 (m, 6H), 7.59 (m, 2H, 2H$^{15}$), 7.67 (m, 1H, H$^{16}$), 7.94 (m, 2H, 2H$^{14}$). $^{13}$C NMR (100 MHz, CDCl$_3$, δ): 22.46 (Me$^{10}$), 22.93 (Me$^{11}$), 23.12 (C$^6$H$_2$), 24.33 (C$^9$H$_2$), 29.25 (C$^5$H), 32.90 (C$^7$H$_2$), 46.22 (NC$^{17}$H$_2$), 50.02 (NC$^{18}$H$_2$), 60.89 (C$^{12}$H$_2$), 77.60 (C$^1$H), 82.78 (C$^4$), 86.51 (C$^8$), 127.38 (2CH), 127.53 (2C$^{14}$H), 127.87 (CH), 128.25 (CH), 128.46 (2CH), 128.78 (2CH), 128.93 (2CH), 129.36 (2C$^{15}$H), 133.79 (C$^{16}$H), 134.81 (Cq), 135.34 (Cq), 140.98 (C$^{13}$), 162.14 (C=O), 162.18 (C=O). Anal. Calcd for C$_{32}$H$_{35}$NO$_7$S: C, 66.53; H, 6.11; N, 2.42; S, 5.55. Found: C, 65.36; H, 6.09; N, 2.10, S, 5.28. More polar isomer 26b, a colorless glass. IR (neat): 2982, 2935 v.s, 1733 v.s, 1663 v.s, 1654 v.s, 1450 v.s, 1379, 1322 v.s, 1312 v.s, 1176 v.s, 1153 v.s, 1084, 1015, 913, 734 v.s, 700 cm$^{-1}$. $^1$H NMR (400 MHz, CDCl$_3$, δ): 1.61 (s, 3H, Me$^{10}$), 1.76 (m, 1H, H$_a^9$), 1.77 (m, 1H, H$_a^9$), 1.79 (s, 3H, Me$^{11}$), 1.92 (m, 1H, H$_e^6$), 2.03 (dddd, 1H, $^3J_{5e6e}$=$^3J_{5e9e}$=6.4 Hz, $^3J_{5e6a}$=$^3J_{5e9a}$=3.2 Hz, H$_e^5$), 2.09 (ddd, 1H, $^2J$=$^3J_{7a6a}$=14.2 Hz, $^3J_{7a6e}$=6.0 Hz, H$_a^7$), 2.23 (br.dd, 1H, $^2J$=14.6 Hz, $^3J_{7e6e}$=5.8 Hz, H$_e^7$), 2.27 (ddd, 1H, $^2J$=13.8 Hz, $^3J_{9e5e}$=6.4 Hz, $^3J_{9e1e}$=3.3 Hz, H$_e^9$), 3.11 (d, 1H, $^2J$=14.0 Hz, H$^{12}$), 3.29 (br.d, 1H, $^2J$=14.0 Hz, H'$^{12}$), 4.34 (m, 1H, H$_e^1$), 4.35 (br.s, 2H, NC$^{17}$H$_2$), 4.485 and 4.51 (ABq, 2H, $^2J$=14.7 Hz, NC$^{18}$H$_2$), 7.19–7.24 (m, 4H), 7.30–7.40 (m, 6H), 7.57 (m, 2H, 2H$^{15}$), 7.66 (m, 1H, H$^{16}$), 7.92 (m, 2H, 2H$^{14}$). $^{13}$C NMR (100 MHz, CDCl$_3$, δ): 21.84 (Me$^{11}$), 22.49 (Me$^{10}$), 23.24 (C$^9$H$_2$), 23.50 (C$^6$H$_2$), 30.71 (C$^5$H), 32.71 (C$^7$H$_2$), 46.27 (NC$^{17}$H$_2$), 50.04 (NC$^{18}$H$_2$), 60.49 (C$^{12}$H$_2$), 78.19 (C$^1$H), 83.11 (C$^4$), 86.30 (C$^8$), 127.36 (2CH), 127.63 (2C$^{15}$H), 127.90 (CH), 128.26 (CH), 128.48 (2CH), 128.80 (2CH), 128.95 (2CH), 129.38 (2C$^{14}$H), 133.93 (C$^{16}$H), 134.84 (Cq), 135.35 (Cq), 141.09 (C$^{13}$), 162.10 (C=O), 162.21 (C=O).

EXAMPLE 19

Preparation of (1R,4R,5R,8R)-4,8-dimethyl-8-phenoxycarbonyloxy-4-phenylsulfonylmethyl-2,3-dioxabicyclo[3.3.1]nonane (27a) and (1R,4S, 5R,8R)-4,8-dimethyl-8-phenoxycarbonyloxy-4-phenylsulfonylmethyl-2,3-dioxabicyclo[3.3.1]nonane (27b) (Scheme 8).

The mixture of diastereomeric (1R,4R, 5R,8R)-4,8-dimethyl-8-phenoxycarbonyloxy-4-phenylthiomethyl-2,3-dioxabicyclo [3.3.1]nonane 20a and (1R,4S,5R,8R)-4,8-dimethyl-8-phenoxycarbonyloxy-4-phenylthiomethyl-2,3-dioxabicyclo[3.3.1]nonane 20b (75 mg, 0.181 mmol, 25% yield, ratio 20a/20b ca. 56:44) was prepared by phenoxycarbonylation of hydroxysulfides 2a,b. The sulfides 20a,b, a colorless solid, mp 64–67° C. $^1$H NMR (CDCl$_3$, 250 MHz, δ): 1.29 (br.s, Me$^{11}$ 20a) and 1.61 (br.s, Me$^{11}$ 20b), total 3H; 1.777 (br.s, Me$^{10}$ 20b) and 1.784 (br.s, Me$^{10}$ 20a), total 3H; 1.80–2.05 (m, 4H); 2.18 (ddd, $^2J$=13.8 Hz, $^3J_{9e5e}$=5.8 Hz, $^3J_{9e1e}$=3.5 Hz, H$_e^9$ 20a), 2.29–2.48 (m, totla 3H; 3.00 and 3.06 (br.) (ABq, $^2J$=12.1 Hz, H$^{12}$+H'$^{12}$ 20b), 3.36 (d, $^2J$=12.9 Hz, H$^{12}$ 20a) and 3.75 (br.d, $^2J$=12.9 Hz, H'$^{12}$ 20a), total 2H; 4.41 (dd, $^3J_{1e9e}$=3.5 Hz, $^3J_{1e9a}$=1.1 Hz, H$_e^1$ 20a) and 4.44 (dd, $^3J_{1e9e}$=3.9 Hz, $^3J_{1e9a}$=1.4 Hz, H$_e^1$ 20b), total 1H; 7.16–7.48 (m, 10H). $^{13}$C NMR (CDCl$_3$, 63 MHz) (δ): Isomer 20a: 22.01 (Me$^{11}$), 22.28 (Me$^{10}$), 23.37 (C$^6$H$_2$), 23.95 (C$^9$H$_2$), 28.47 (C$^5$H), 32.38 (C$^7$H$_2$), 40.73 (C$^{12}$H$_2$), 77.50 (C$^1$H), 84.03 (C$^4$), 85.36 (C$^8$), 121.07 (2C$^{o\text{-}phen.}$H), 125.90 (C$^{p\text{-}phen.}$H), 126.33 (C$^{16}$H), 128.95 (2C$^{14}$H), 129.39 (2C$^{m\text{-}phen.}$H), 129.84 (2C$^{15}$H), 136.66 (C$^{13}$), 150.88 (C$^{1\text{-}phen.}$), 151.37 (C=O); Isomer 20b: 21.78 (Me$^{11}$), 22.28 (Me$^{10}$), 23.08 (C$^6$H$_2$), 24.08 (C$^9$H$_2$), 29.80 (C$^5$H), 32.70 (C$^7$H$_2$), 40.83 (C$^{12}$H$_2$), 77.95 (C$^1$H), 84.03 (C$^4$), 85.29 (C$^8$), 121.07 (2C$^{o\text{-}phen.}$H), 125.90 (C$^{p\text{-}phen.}$H), 126.52 (C$^{16}$H), 129.00 (2C$^{14}$H), 129.39 (2C$^{m\text{-}phen.}$H), 129.84 (2C$^{15}$H), 136.22 (C$^{13}$), 150.88 (C$^{1\text{-}phen.}$), 151.37 (C=O).

To a solution of sulfides 20a,b (60 mg, 0.145 mmol) in EtOAc (1.2 mL) was added MCPBA (108 mg of ca. 60%, 0.38 mmol). The mixture was stirred for 6 h at rt, diluted with hexane-EtOAc (3:1, 50 mL), washed with saturated NaHCO$_3$ (2×10 mL) and the water washings were extracted with hexane-EtOAc (3:1, 50 mL). The combined organic extract was dried (Na$_2$SO$_4$+NaHCO$_3$) and evaporated. MPLC (hexane-EtOAc, 80:20) of the residue afforded the diastereomeric sulfones 27a (31.7 mg) and 27b (24.5 mg) (total 60.2 mg, 93% yield). Less polar isomer 27a, a colorless solid, mp 99–100° C., R$_f$=0.30 (hexane-EtOAc, 75:25). $^1$H NMR (CDCl$_3$, 400 MHz, δ): 1.54 (br.s, 3H, Me$^{11}$), 1.72 (s, 3H, Me$^{10}$), 1.83–1.99 (m, 2H, H$_e^6$+H$_a^6$), 2.02 (ddd, 1H, $^2J$=13.8 Hz, $^3J_{9a5e}$=2.8 Hz, $^3J_{9a1e}$=1.6 Hz, H$_a^9$), 2.28–2.39 (m, 4H, H$_e^5$+H$_e^7$+H$_a^7$+H$_e^9$), 3.28 (d, 1H, $^2J$=14.3 Hz, H$^{12}$), 4.23 (br.d, 1H, $^2J$=14.3 Hz, H'$^{12}$), 4.42 (br.dd, 1H, $^3J_{1e9e}$=4.0 Hz, $^3J_{1e9a}$=1.6 Hz, H$_e^1$), 7.15 (m, 2H, 2H$^{o\text{-}phen.}$), 7.24 (m, 1H, H$^{p\text{-}phen.}$), 7.39 (m, 2H, 2H$^{m\text{-}phen.}$), 7.59 (m, 2H, 2H$^{15}$), 7.67 (m, 1H, H$^{16}$), 7.94 (m, 2H, 2H$^{14}$). $^{13}$C NMR (100 MHz, CDCl$_3$, δ): 22.25 (Me$^{10}$), 23.08 (Me$^{11}$), 23.27 (C$^6$H$_2$), 24.51 (C$^9$H$_2$), 29.38 (C$^5$H), 32.75 (C$^7$H$_2$), 60.99 (C$^{12}$H$_2$), 77.86 (C$^1$H), 82.84 (C$^4$), 85.12 (C$^8$), 121.10 (2C$^{o\text{-}phen.}$H), 126.00 (C$^{p\text{-}phen.}$H), 127.57 (2C$^{14}$H), 129.40 (2C$^{15}$H), 129.39 (2C$^{m\text{-}phen.}$H), 133.81 (C$^{16}$H), 141.05 (C$^{13}$), 150.89 (C$^{1\text{-}phen.}$), 151.43 (C=O). Anal. Calcd for C$_{23}$H$_{26}$O$_7$S: C, 61.87; H, 5.87; S, 7.18. Found: C, 62.21; H, 5.76; S, 6.95. More polar isomer 27b, a colorless solid, mp 109–111° C., R$_f$=0.26

(hexane-EtOAc, 75:25). $^1$H NMR (CDCl$_3$, 400 MHz, δ): 1.66 (s, 3H, Me$^{10}$), 1.84 (br.s, 3H, Me$^{11}$), 1.87–1.97 (m, 2H, H$_e^6$+H$_a^9$), 2.02 (m, 1H, H$_e^6$), 2.15 (ddd, 1H, $^2$J=$^3$J$_{7a6a}$=15.0 Hz, $^3$J$_{7a6e}$=6.0 Hz, H$_a^7$), 2.18–2.39 (m, 1H, H$_e^5$), 2.31 (br.dd, 1H, $^2$J=15.0 Hz, $^3$J$_{7e6e}$=6.0 Hz, H$_e^7$), 2.37 (ddd, 1H, $^2$J=13.8 Hz, $^3$J$_{9e5e}$=6.4 Hz, $^3$J$_{9e1e}$=3.5 Hz, H$_e^9$), 3.14 (d, 1H, $^2$J=14.0 Hz, H$^{12}$), 3.34 (br.d, 1H, $^2$J=14.0 Hz, H$'^{12}$), 4.40 (br.dd, 1H, $^3$J$_{1e9e}$=3.5 Hz, H$_e^1$), 7.15 (m, 2H, 2H$^{o\text{-}phen.}$), 7.24 (m, 1H, H$^{p\text{-}phen.}$), 7.38 (m, 2H, 2H$^{m\text{-}phen.}$), 7.59 (m, 2H, 2H$^{15}$), 7.68 (m, 1H, H$^{16}$), 7.94 (m, 2H, 2H$^{14}$). $^{13}$C NMR (63 MHz, CDCl$_3$, δ): 21.94 (Me$^{11}$), 22.28 (Me$^{10}$), 23.41 (C$^9$H$_2$), 23.67 (C$^6$H$_2$), 30.83 (C$^5$H), 32.49 (C$^7$H$_2$), 60.50 (C$^{12}$H$_2$), 78.47 (C$^1$H), 83.17 (C$^4$), 84.93 (C$^8$), 121.09 (2C$^{o\text{-}phen.}$H), 126.01 (C$^{p\text{-}phen.}$H), 127.65 (2C$^{14}$H), 129.42 (2C$^{15}$H), 129.47 (2C$^{m\text{-}phen.}$H), 133.95 (C$^{16}$H), 141.15 (C$^{13}$), 150.89 (C$^{1\text{-}phen.}$), 151.42 (C=O). Anal. Calcd. for C$_{23}$H$_{26}$O$_7$S: C, 61.87; H, 5.87; S, 7.18. Found: C, 61.78; H, 5.98; S, 7.19.

EXAMPLE 20

Preparation of (1S,4S,5S,8S)-4,8-dimethyl-4-phenylsulfonylmethyl-2,3-dioxabicyclo[3.3.1]nonan-8-ol (21'a) and 1S,4R,5S,8S)-4,8-dimethyl-4-phenylsulfonylmethyl-2,3-dioxabicyclo[3.3.1]nonan-8-ol (21'b) (Scheme 9).

The title compounds were prepared by oxidation of sulfides 2'a,b as described in example 13 for the corresponding (1R, 5R, 8R)-epimers 21a,b. $^1$H NMR spectra in CDCl$_3$ of individual diastereomers 21'a,b and 21a,b (example 13) are identical. 21'a is a colorless solid, mp 112–113° C. (hexane-EtOAc), 21'b is a colorless oil, total yield of 21'a,b 90%.

EXAMPLE 21

Preparation of 1S,4S5S,8S)-8-acetoxy-4,8-dimethyl-4 phenylsulfonylmethyl-2,3-dioxabicyclo[3.3.1]nonane (23'a) and (1S,4R,5S,8S)-8-acetoxy-4,8-dimethyl-4-phenylsulfonylmethyl-2,3-dioxabicyclo[3.3.1]nonane (23'b) (Scheme 9).

To TMS-derivative 16'a,b, prepared from 2'a,b (0.854 mmol, 252 mg) and TMSOTf as described in example 10, was added AcCl (2.0 mL) and the mixture was stirred at rt for 50 h. The mixture was evaporated and the crude acetyloxysulfide 13'a,b was dissolved in EtOAc (8 mL) and oxidized by MCPBA (526 mg of ca. 70%, 2.135 mmol) at rt for 6 h. Workup as in example 15 followed by flash chromatography (silica gel, hexane-EtOAc 3:1) afforded a mixture of sulfones 23'a,b (265 mg, 84%). The mixture was separated by MPLC (hexane-EtOAc, 3:1) to give the individual epimers 23'a as a colorless solid, mp 96–98° C. and 23'b, as a colorless solid, mp 101–102° C. NMR Spectra are consistent with those described above for (1R, 5R, 8R)-epimers 23a and 23b (example 15).

EXAMPLE 22

Preparation of (1S,4S,5S,7S,8S)-7-benzoyloxy-4,8-dimethyl-4-phenylsulfonylmethyl-2,3-dioxabicyclo[3.3.1]nonan-8-ol (29a) and (1S,4R,5S,7S,8S)-7-benzoyloxy-4,8-dimethyl-4-phenylsulfonylmethyl-2,3-dioxabicyclo[3.3.1]nonan-8-ol (29b) (Scheme 9).

To a solution of sulfides 4a, and 4b (80 mg, 0.193 mmol) in EtOAc (2 mL) at 0° C. was added a solution of MCPBA (94 mg of ca. 85%, 0.46 mmol) in EtOAc (2 mL). The mixture was stirred for 2 h at 0–5° C. and for 4 h at rt, diluted with EtOAc (10 mL) and washed with saturated NaHCO$_3$ (3×5 mL). Water washings were extracted with EtOAc (2×10 mL), the combined organic extract was dried (Na$_2$SO$_4$) and evaporated. Flash chromatography (hexane-EtOAc, 65:35) of the residue gave a mixture of diastereomeric sulfones 29a and 29b (80.5 mg, 93% yield) as colorless oil. The diastereomers were separated by MPLC (hexane-EtOAc, 60:40). Less polar isomer 29b, a colorless solid, mp 132–133° C., R$_f$ 0.42 (hexane-EtOAc, 60:40). $^1$H NMR (400 MHz, CDCl$_3$, δ): 1.36 (s, 3H, Me$^{10}$), 1.90 (br.s, 3H, Me$^{11}$), 1.93 (ddd, 1H, $^2$J=13.8 Hz, $^3$J$_{6a7a}$=12.0 Hz, $^3$J$_{6a5e}$=3.5 Hz, H$_a^6$), 2.16 (ddd, 1H, $^2$J=13.8 Hz, $^3$J$_{9a5e}$=3.3 Hz, $^3$J$_{9a1e}$=2.0 Hz, H$_a^9$), 2.30 (dddd, 1H, $^2$J=13.8 Hz, $^3$J$_{9e1e}$=$^3$J$_{9e5e}$=3.6 Hz, $^4$J$_{9e6e}$=2.9 Hz, H$_e^9$), 2.34 (br.s., 1H, OH), 2.43 (dddd, 1H, $^3$J$_{5e9e}$=3.6 Hz, $^3$J$_{5e6a}$=3.5 Hz, $^3$J$_{5e9a}$=3.3 Hz, $^3$J$_{5e6e}$=2.9 Hz, $^4$J$_{5e1e}$=1.5 Hz, H$_e^5$), 2.57 (dddd, 1H, $^2$J=13.8 Hz, $^3$J$_{6e7a}$=6.1 Hz, $^3$J$_{6e5e}$=$^4$J$_{6e9e}$=2.9 Hz, H$_e^6$), 3.16 (d, 1H, $^2$J=13.9 Hz, H$^{12}$), 3.58 (br.d, 1H, $^2$J=13.9 Hz, H$'^{12}$), 3.97 (ddd, 1H, $^3$J$_{1e9e}$=3.6 Hz, $^3$J$_{1e9a}$=2.0 Hz, $^4$J$_{1e5e}$=1.5 Hz, H$_e^1$), 5.57 (dd, 1H $^3$J$_{7a6a}$=12.0 Hz, $^3$J$_{7a6e}$=6.1 Hz, H$_a^7$), 7.50 (m, 2H), 7.58–7.63 (m, 3H), 7.67 (m, 1H), 7.97–8.05 (m, 4H). $^{13}$C NMR (100 MHz, CDCl$_3$, δ): 21.71 (Me$^{11}$), 23.27 (C$^9$H$_2$), 24.31 (Me$^{10}$), 29.49 (C$^6$H$_2$), 33.61 (C$^5$H), 60.24 (C$^{12}$H$_2$), 72.70 (C$^8$), 74.58 (C$^7$H), 82.91 (C$^4$), 83.80 (C$^1$H), 127.79 (2C$^{14}$H), 128.55 (2CH$^{m\text{-}benz.}$), 129.39 (2C$^{15}$H), 129.49 (2CH$^{o\text{-}benz.}$), 129.97 (C$^{1\text{-}benz.}$), 133.30 (CH$^{p\text{-}benz.}$), 133.91 (C$^{16}$H), 141.02 (C$^{13}$), 165.69 (C=O). Anal. Calcd. for C$_{23}$H$_{26}$O$_7$S: C, 61.87; H, 5.87; S 7.18. Found: C, 61.60; H 5.91; S 7.43. More polar isomer 29a, a colorless solid, mp 182–183° C., R$_f$ 0.36 (hexane-EtOAc, 60:40). $^1$H NMR (400 MHz, CDCl$_3$, δ): 1.41 (s, 3H, Me$^{10}$), 1.64 (br.s, 3H, Me$^{11}$), 1.88 (ddd, 1H, $^2$J=13.3 Hz, $^3$J$_{6a7a}$=11.8 Hz, $^3$J$_{6a5e}$=3.6 Hz, H$_a^6$), 2.25 (ddd, 1H, $^2$J=14.0 Hz, $^3$J$_{9a1e}$=$^3$J$_{9a5e}$=2.8 Hz, H$_a^9$), 2.28 (dddd, 1H, $^2$J=14.0 Hz, $^3$J$_{9e5e}$=3.2 Hz, $^3$J$_{9e1e}$=2.8 Hz, $^4$J$_{9e6e}$=2.2 Hz, H$_e^9$), 2.38 (br.s., 1H, OH), 2.39 (dddd, 1H, $^2$J=13.3 Hz, $^3$J$_{6e7a}$=6.2 Hz, $^3$J$_{6e5e}$=3.2 Hz, $^4$J$_{6e9e}$=2.2 Hz, H$_e^6$), 2.61 (br.dddd, 1H, $^3$J$_{5e6a}$=3.6 Hz, $^3$J$_{5e9e}$=$^3$J$_{5e9a}$= $^3$J$_{5e6e}$=3.2 Hz, H$_e^5$), 3.31 (d, 1H, $^2$J=14.3 Hz, H$^{12}$), 4.23 (br.d, 1H, $^2$J=14.3 Hz, H$'^{12}$), 3.97 (br.dd, 1H, $^3$J$_{1e9e}$=$^3$J$_{1e9a}$=2.8 Hz, H$_e^1$), 5.71 (dd, 1H, $^3$J$_{7a6a}$=11.8 Hz, $^3$J$_{7a6e}$=6.2 Hz, H$_a^7$), 7.48 (m, 2H), 7.58–7.62 (m, 3H), 7.68 (m, 1H), 7.96 (m, 2H), 8.04 (m, 2H). $^{13}$C NMR (100 MHz, CDCl$_3$, δ): 23.28 (Me$^{11}$), 24.19 (C$^9$H$_2$), 24.41 (Me$^{10}$), 29.13 (C$^6$H$_2$), 32.10 (C$^5$H), 60.87 (C$^{12}$H$_2$), 72.71 (C$^8$), 74.51 (C$^7$H), 82.51 (C$^4$), 83.14 (C$^1$H), 127.59 (2C$^{14}$H), 128.56 (2CH$^{m\text{-}benz.}$), 129.42 (2C$^{15}$H), 129.51 (2CH$^{o\text{-}benz.}$), 129.93 (C$^{1\text{-}benz.}$), 133.31 CH$^{p\text{-}benz.}$), 133.87 (C$^{16}$H), 140.96 (C$^{13}$), 165.61 (C=O). Anal. Calcd for C$_{23}$H$_{26}$O$_7$S: C, 61.87; H, 5.87; S 7.18. Found: C, 61.60; H 5.81; S 6.87.

EXAMPLE 23

Preparation of (1S,4S,5S,7S,8S)-7-benzoyloxy-4-n-butylsulfonylmethyl-4,8-dimethyl-2,3-dioxabicyclo[3.3.1] nonan-8-ol (30a) and (1S,4R,5S,7S,8S)-7-benzoyloxy-4-n-butylsulfonylmethyl-4,8-dimethyl-2,3-dioxabicyclo [3.3.1] nonan-8-ol (30b) (Scheme 9).

To a solution of sulfides 5a and 5b (37.5 mg, 0.095 mmol, 5a/5b~55:45) in EtOAc (1 mL) at 0° C. was added a solution of MCPBA (49 mg of ca. 85%, 0.24 mmol) in EtOAc (1.5 mL). The mixture was stirred for 3 h at 0–5° C. and for additional 3 h at rt, diluted with EtOAc (10 mL) and washed with saturated NaHCO$_3$ (2×10 mL). Water washings were extracted with EtOAc (15 mL, organic extract was dried (Na$_2$SO$_4$, NaHCO$_3$) and evaporated. Flash chromatography (hexane-EtOAc, 70:30) of the residue afforded the separated diastereomeric sulfones 30a (19.5 mg) and 30b (17.2 mg) (total 36.7 mg, 91% yield). Less polar isomer 30b, a colorless oil, R$_f$ 0.36 (hexane-EtOAc, 60:40). $^1$H NMR (400 MHz, CDCl$_3$, δ): 0.99 (t, 3H, $^3$J=7.4 Hz, Me$^{16}$CH$_2$), 1.44 (s, 3H, Me$^{10}$), 1.50 (tq, 2H, $^3$J=$^3$J=7.4 Hz, MeC$^{15}$H$_2$CH$_2$), 1.86–1.95 (m, 3H, $H_a^6$+$CH_2C^{14}H_2CH_2S$), 1.88 (s, 3H, $Me^{11}$), 2.16 (ddd, 1H, $^2J$=13.0 Hz, $^3J_{9a1e}$=2.5 Hz, $^3J_{9a5e}$=1.9 Hz, $H_a^9$), 2.28 (ddddd, 1H, $^3J_{5e9e}$=3.5 Hz, $^3J_{5e6e}$=2.9 Hz, $^3J_{5e6a}$=2.5 Hz, $^3J_{5e9a}$=1.9 Hz, $^4J_{5e1e}$=1.8 Hz, $H_e^5$), 2.31 (dddd, 1H, $^2J$=13.0 Hz, $^3J_{9e5e}$=3.5 Hz, $^3J_{9e1e}$=3.3 Hz, $^4J_{9e6e}$= 2.9 Hz, $H_e^9$), 2.32 (br.s., 1H, OH), 2.42 (dddd, 1H, $^2J$=13.8 Hz, $^3J_{6e7a}$=6.1 Hz, $^3J_{6e5e}$=$^4J_{6e9e}$=2.9 Hz, $H_e^6$), 3.08 (m, 2H, $CH_2C^{13}H_2S$), 3.17 (d, 1H, $^2J$=13.8 Hz, $H^{12}$), 3.37 (br.d, 1H, $^2J$=13.8 Hz, $H'^{12}$), 4.00 (ddd, 1H, $^3J_{1e9e}$=3.5 Hz, $^3J_{1e9a}$=2.5 Hz, $^4J_{1e5e}$=1.8 Hz, $H_e^1$), 5.68 (dd, 1H, $^3J_{7a6a}$=12.0 Hz, $^3J_{7a6q}$=6.1 Hz, $H_a^7$), 7.48 (m, 2H, $2HC^{m-benz.}$), 7.61 (m, 1H, $HC^{p-benz.}$), 8.02 (m, 2H, $2HC^{o-benz.}$). $^{13}C$ NMR (63 MHz, $CDCl_3$, δ): 13.52 ($Me^{16}$), 21.16 ($Me^{11}$), 21.68 ($C^{15}H_2$), 23.23 ($C^9H_2$), 24.13 ($C^{14}H_2$), 24.36 ($Me^{10}$), 29.33 ($C^6H_2$), 33.79 ($C^5H$), 56.19 ($C^{13}H_2$), 56.57 ($C^{12}H_2$), 72.71 ($C^8$), 74.44 ($C^7H$), 82.53 ($C^4$), 83.73 ($C^1H$), 128.60 ($2CH^{m-benz.}$), 129.49 ($2CH^{o-benz.}$), 129.87 ($C^{1-benz.}$), 133.36 ($CH^{p-benz.}$), 165.79 (C=O). More polar isomer 30a, a colorless solid, mp 140–142° C., $R_f$ 0.25 (hexane-EtOAc, 60:40). $^1H$ NMR (400 MHz, $CDCl_3$, δ): 0.98 (t, 3H, $^3J$=7.4 Hz, $Me^{16}CH_2$), 1.43 (s, 3H, $Me^{10}$), 1.49 (tq, 2H, $^3J$=$^3J$=7.4 Hz, $MeC^{15}H_2CH_2$), 1.64 (s, 3H, $Me^{11}$), 1.83–1.91 (m, 2H, $CH_2C^{14}H_2CH_2S$), 1.85 (ddd, $^2J$=13.5 Hz, $^3J_{6a7a}$=11.7 Hz, $^3J_{6a5e}$=3.5 Hz, $H_a^6$), 2.25 (m, 2H, $H_a^9$+$H_e^9$), 2.31 (m, 1H, $^3J_{5e6a}$=$^3J_{5e9e}$=3.5 Hz, $^3J_{5e6e}$=$^3J_{5e9a}$=2.5 Hz, $H_e^5$), 2.40 (br.s., 1H, OH), 2.38 (ddddd, 1H, $^2J$=13.5 Hz, $^3J_{6e7a}$=6.1 Hz, $^3J_{6e5e}$≈2.5 Hz, $^4J_{6e9e}$≈J≈1.6 Hz, $H_e^6$), 3.08 (m, 2H, $CH_2C^{13}H_2S$), 3.50 (d, 1H, $^2J$=14.3 Hz, $H^{12}$), 3.76 (br.d, 1H, $^2J$=13.8 Hz, $H'^{12}$), 4.01 (br.dd, 1H, $^3J_{1e9e}$=$^3J_{1e9a}$=2.5 Hz, $H_e^1$), 5.72 (dd, 1H, $^3J_{7a6a}$=11.7 Hz, $^3J_{7a6e}$=6.2 Hz, $H_a^7$), 7.48 (m, 2H, $2HC^{m-benz.}$), 7.60 (m, 1H, $HC^{p-benz.}$), 8.03 (m, 2H, $2HC^{o-benz.}$). $^{13}C$ NMR (63 MHz, $CDCl_3$, δ): 13.55 ($Me^{16}$), 21.70 ($C^{15}H_2$), 22.46 ($Me^{11}$), 23.86 ($C^{14}H_2$), 24.12 ($C^9H_2$), 24.40 $Me^{10}$), 29.06 ($C^6H_2$), 32.84 ($C^5H$), 55.41 ($C^{13}H_2$), 56.64 ($C^{12}H_2$), 72.71 ($C^8$), 74.36 ($C^7H$), 81.95 ($C^4$), 83.12 ($C^1H$), 128.57 ($2CH^{m-benz.}$), 129.51 ($2CH^{o-benz.}$), 129.90 ($C^{1-benz.}$), 133.33 ($CH^{p-benz.}$), 165.58 (C=O). Anal. Calcd for $C_{21}H_{30}O_7S$: C, 59.14; H, 7.09; S, 7.52. Found: C, 59.34; H, 7.17; S, 7.22.

EXAMPLE 24

Preparation of (1S,4S,5S,7R,8S)-7-benzoyloxy-4,8-dimethyl-4-phenylsulfonylmethyl-2,3-dioxabicyclo[3.3.1]nonan-8-ol (31a) and (1S,4R,5S,7R,8S)-7-benzoyloxy-4,8-dimethyl-4-phenylsulfonylmethyl-2,3-dioxabicyclo[3.3.1]nonan-8-ol (31b) (Scheme 9).

To a solution of sulfides 6a and 6b (19.5 mg of ca. 94% purity, 0.0435 mmol, ca. 65:35) in EtOAc (1.2 mL) at rt was added MCPBA (32 mg of ca. 60%, 0.108 mmol) in EtOAc (2 mL). The mixture was stirred for 5 h at rt, poured into satruated $NaHCO_3$ (10 mL), extracted with hexane-EtOAc (30 mL, 3:2). The organic extract was dried ($Na_2SO_4$, $NaHCO_3$), evaporated and MPLC (hexane-EtOAc, 60:40) of the residue afforded the diastereomeric sulfones 31a (11.0 mg) and 31b (6.3 mg) (total 89% yield). Less polar isomer 31b, a colorless solid, mp 160–162° C. (dec.). $^1H$ NMR 400 MHz, $CDCl_3$, δ): 1.37 (s, 3H, $Me^{10}$), 1.86 (s, 3H, $Me^{11}$), 1.97 (br.s., 1H, OH), 2.08 (ddd, 1H, $^2J$=13.6 Hz, $^3J_{9a5e}$=3.0 Hz, $^3J_{9a1e}$=1.6 Hz, $H_a^9$), 2.21 (ddd, 1H, $^2J$=16.0 Hz, $^3J_{6a5e}$= 4.4 Hz, $^3J_{6a7e}$=2.0 Hz, $H_a^6$), 2.32 (m, 1H, $H_e^5$), 2.34–2.42 (m, 2H, $H_e^6$+$H_e^9$), 3.11 (d, 1H, $^2J$=14.0 Hz, $H^{12}$), 3.58 (br.d, 1H, $^2J$=14.0 Hz, $H'^{12}$), 3.94 (dd, 1H, $^3J_{1e9e}$=3.6 Hz, $^3J_{1e9a}$= 1.6 Hz, $H_e^1$), 5.27 (dd, 1H, $^3J_{7e6e}$=6.3 Hz, $^3J_{7e6a}$=2.0 Hz, $H_e^7$), 7.34 (m, 4H), 7.49 (m, 2H), 7.68 (m, 1H), 7.64 (m, 2H), 7.97 (m, 2H). $^{13}C$ NMR (100 MHz, $CDCl_3$, δ): 21.89 ($Me^{11}$), 22.83 ($C^9H_2$), 23.33 ($Me^{10}$), 29.32 ($C^6H_2$), 32.20 ($C^5H$), 60.85 ($C^{12}H_2$), 73.33 ($C^8$), 74.80 ($C^7H$), 81.87 ($C^1H$), 82.04 ($C^4$), 127.02 ($2C^{14}H$), 128.48 ($2CH^{m-benz.}$), 129.17 ($2C^{15}H$), 129.65 ($2CH^{o-benz.}$), 129.83 ($C^{1-benz.}$), 133.18 ($CH^{p-benz.}$), 133.55 ($C^{16}H$), 140.88 ($C^{13}$), 166.08 (C=O). More polar isomer 31a, a colorless solid, mp 71–73° C. $^1H$ NMR (400 MHz, $CDCl_3$, δ): 1.39 (s, 3H, $Me^{10}$), 1.51 (s, 3H, $Me^{11}$), 1.94 (br.s., 1H, OH), 2.14 (ddd, 1H, $^2J$=14.0 Hz, $^3J_{9a5e}$=5.0 Hz, $^3J_{9a1e}$=2.4 Hz, $H_a^9$), 2.15 (ddd, 1H, $^2J$=16.0 Hz, $^3J_{6a5e}$=4.7 Hz, $^3J_{6a7e}$=1.6 Hz, $H_a^6$), 2.35 (ddd, 1H, $^2J$=16.0 Hz, $^3J_{6e5e}$=6.5 Hz, $^3J_{6a7e}$=5.0 Hz, $H_e^6$), 2.36 (m, 1H, $H_e^9$), 2.50 (m, 1H, $H_e^5$), 3.36 (d, 1H, $^2J$=14.3 Hz, $H^{12}$), 3.83 (dd, 1H, $^3J_{1e9e}$=3.6 Hz, $^3J_{1e9a}$=1.6 Hz, $H_e^1$), 4.34 (br.d, 1H, $^2J$=14.3 Hz, $H'^{12}$), 5.29 (dd, 1H, $^3J_{7e6e}$=6.5 Hz, $^3J_{7e6a}$=1.6 Hz, $H_e^7$), 7.44 (m, 2H), 7.55–7.62 (m, 3H), 7.68 (m, 1H), 7.97 (m, 2H), 8.10 (m, 2H). $^{13}C$ NMR (100 MHz, $CDCl_3$, δ): 23.23 ($Me^{11}$), 23.41 ($Me^{10}$) 23.97 ($C^9H_2$), 28.71 ($C^6H_2$), 30.15 ($C^5H$), 60.89 ($C^{12}H_2$), 73.35 ($C^8$), 74.14 ($C^7H$), 81.21 ($C^1H$), 81.71 ($C^4$), 127.58 ($2C^{14}H$), 128.48 ($2CH^{m-benz.}$), 129.42 ($2C^{15}H$), 129.90 ($2CH^{o-benz.}$), 130.11 ($C^{1-benz.}$), 133.15 ($CH^{p-benz.}$), 133.83 ($C^{16}H$), 141.10 ($C^{13}$), 166.20 (C=O). DCI HRMS:obsd 447.15100, calcd for $C_{23}H_{27}O_7S$ (M+1) 447.14775.

EXAMPLE 25

Preparation of (1R,4R,5R,8R)-8-acetoxy-4,8-dimethyl-4-phenylsulfonylmethyl-2,3-dioxabicyclo[3.3.1]nonane (23a) (Scheme 10).

To a solution of hydroxysulfone 21a (230 mg, 0.705 mmol) and 2,6-lutidine (193 mg, 1.80 mmol) in $CH_2Cl_2$ (5 mL) at −30° C. was added TfOTMS (354 mg, 1.50 mmol). Temperature was slowly raised to 0° C. (30 min) and the mixture was stirred at 0° C. for 1.5 h. The resulting solution was poured into ice-cold saturated $NaHCO_3$ (30 mL), extracted with hexane-EtOAc (9:1, 150 mL), dried ($Na_2SO_4$) and evaporated to give the crude TMS-derivative 32a, containing 2,6-lutidine as an impurity (305 mg, 1:0.35), a colorless oil, $R_f$ 0.36 (hexane-EtOAc 85:15). $^1H$ NMR (250 MHz, $CDCl_3$, δ): 0.12 (s, 9H, $Me_3S$), 1.37 (s, 3H, $Me^{10}$), 1.51 (br.s, 3H, $Me^{11}$), 1.66 (ddd, 1H, $^2J$=13.6 Hz, $^3J_{9a5e}$=$^3J_{9a1e}$=3.4 Hz, $H_a^9$), 1.79–1.90 (m, 1H, $H_a^6$+$H_e^6$), 2.11–2.22 (m, 3H, $H_e^7$+$H_a^7$+$H_e^9$) 2.25 (m, 1H, $H_e^5$), 3.27 (d, 1H, $^2J$=14.2 Hz, $H^{12}$), 3.61 (dd, $^3J_{1e9e}$=$J_{1e9a}$=3.4 Hz, $H_e^1$), 4.24 (br.d, 1H, $^2J$=14.2 Hz, $H'^{12}$), 7.59 (m, 2H, $H^{15, 15'}$), 7.68 (m, 1H, $H^{16}$), 7.96 (m, 2H, $H^{14, 14'}$); $^{13}C$ NMR (63 MHz, $CDCl_3$, δ): 2.46 ($Me_3Si$), 22.93 ($Me^{11}$), 23.49 ($C^6H_2$), 24.33 ($C^9H_2$), 27.15 ($Me^{10}$), 30.03 ($C^5H$), 35.97 ($C^7H_2$), 61.09 ($C^{12}H_2$), 74.40 ($C^8$), 82.45 ($C^1H$), 82.65 ($C^4$), 127.54 ($2C^{14}H$), 129.31 ($2C^{15}H$), 133.65 ($C^{16}H$), 141.22 ($C^{13}$).

The mixture of crude TMS-derivative 32a (285 mg) and AcCl (3 mL) was stirred at rt for 45 h, evaporated in vacuo, the residue was dissolved in EtOAc (20 mL) and poured into saturated $NaHCO_3$ (30 mL). After addition of hexane (40 mL) the organic layer was separated and the water layer was extracted with hexane-EtOAc (7:3, 60 mL). The combined organic extract was dried ($Na_2SO_4$), evaporated and purified by flash chromatography (hexane-EtOAc, 80:20) to give the sulfone 23a (230 mg, 95%), mp 98–99° C. The NMR spectrum of the sulfone 23a is identical to that of sulfone 23a prepared as described in Example 15.

EXAMPLE 26

Preparation of (1R,4R,5R,8R)-4,8-dimethyl-8-phenoxyacetoxy-4-phenylsulfonylmethyl-2,3-dioxabicyclo[3.3.1]nonane (33a) (Scheme 10).

A mixture of TMS-derivative 32a (prepared from 0.22 mmol of hydroxysulfone 21a as described in Example 25), phenoxyacetyl chloride (1.1 mL) and freshly oven-dried CsF (152 mg, 1.0 mmol) in acetonitrile (2.4 mL) was stirred at rt for a week. The mixture was poured into saturated NaHCO$_3$ (40 mL) and stirred for 1 h at rt. Hexane-EtOAc (75:25, 100 mL) was added, the organic layer was separated and washed with saturated NaHCO$_3$ (25 mL). The combined water washings were extracted with hexane-EtOAc (2:1, 75 mL). The combined organic extract was dried (Na$_2$SO$_4$+ NaHCO$_3$) and evaporated. MPLC (hexane-EtOAc, 80:20) of the residue gave the sulfone 33a (57 mg, 56% yield) as an oil. $^1$H NMR (CDCl$_3$, 400 MHz, δ): 1.50 (br.s, 3H, Me$^{11}$), 1.60 (m, 1H, H$_a^6$), 1.67 (s, 3H, Me$^{10}$), 1.74 (m, 1H, H$_a^9$), 1.86 (m, 1H, H$_e^6$), 2.16–2.27 (m, 4H, H$_e^5$+H$_e^7$+H$_a^7$+H$_e^9$), 3.24 (d, 1H, $^2$J=14.4 Hz, H$^{12}$), 4.19 (br.d, 1H, $^2$J=14.4 Hz, H$^{12'}$), 4.36 (br.d, 1H, $^3$J$_{1e9e}$=3.2 Hz, H$_e^1$), 4.57 (s, 2H, C$^{17}$H$_2$O), 6.89 (m, 2H, 2H$^{o\text{-}phen.}$), 7.00 (m, 1H, H$^{p\text{-}phen.}$), 7.30 (m, 2H, 2H$^{m\text{-}phen.}$), 7.58 (m, 2H, 2H$^{15}$), 7.66 (m, 1H, H$^{16}$), 7.94 (m, 2H, 2H$^{14}$). $^{13}$C NMR (100 MHz, CDCl$_3$, δ): 22.60 (Me$^{10}$), 23.02 (Me$^{11}$), 23.18 (C$^6$H$_2$), 24.36 (C$^9$H$_2$), 29.29 (C$^5$H), 32.97 (C$^7$H$_2$), 60.93 (C$^{12}$H$_2$), 65.52 (C$^{17}$H$_2$O), 77.84 (C$^1$H), 82.76 (C$^4$), 84.47 (C$^8$), 114.36 (2C$^{o\text{-}phen.}$H), 121.73 (C$^{p\text{-}phen.}$H), 127.53 (2C$^{14}$H), 129.37 (2C$^{15}$H), 129.58 (2C$^{m\text{-}phen.}$H), 133.78 (C$^{16}$H), 141.02 (C$^{13}$), 157.65 (C$^{1\text{-}phen.}$), 167.93 (C=O). DCI HRMS:obsd 461.16000, calcd for C$_{24}$H$_{29}$O$_7$S (M+1) 461.16340.

EXAMPLE 27

Preparation of (1R,4R,5R,8R)-4,8-dimethyl-8-(p-methoxybenzyloxy)-4-phenylsulfonylmethyl-2,3-dioxabicyclo[3.3.1]nonane (34a) (Scheme 11).

To a suspension of hydroxysulfone 21a (280 mg, 0.858 mmol) in ether (3 mL) at 0° C. was added a solution of O-(p-methoxybenzyl) trichloroacetimidate 44 (1.287 g of ca. 93%, 4.19 mmol) in CH$_2$Cl$_2$ (1.5 mL), the mixture was stirred for 10 min until homogeneous solution was formed. Then at 0° C. a solution of TfOH in ether (0.43 mL of 0.1M TfOH solution in abs. ether, 0.043 mmol) was added and the green-yellow mixture was stirred for 1.5 h at 0° C. and for 10 h at rt A second portion of TfOH solution (0.25 mL, 0.025 mmol) was added and the mixture was stirred for 12 h and then additional portions of imidate 44 (772 mg, 2.51 mmol) and TfOH solution (0.25 mL, 0.025 mmol) were added and the mixture was stirred for additional 8 h until consumption of 21a (TLC monitoring). The mixture was diluted with ether (15 mL) and hexane (15 mL), NaHCO$_3$ (0.6 g) and Na$_2$SO$_4$ (2 g) were added. After being stirred overnight the mixture was filtered, evaporated, fractionated by flash chromatography (hexane-EtOAc 75:25) and purified by a number of MPLC (hexane-EtOAc 78:22) to afford 34a (175 mg, 45.7%) as a pale yellowish oil, R$_f$ 0.40 (hexane-EtOAc 75:25). $^1$H NMR (400 MHz, CDCl$_3$, δ): 1.38 (s, 3H, Me$^{10}$), 1.53 (br.s, 3H, Me$^{11}$), 1.81 (dddd, 1H, $^2$J=$^3$J$_{6a7a}$ 14.0 Hz, $^3$J$_{6a5e}$=6.4 Hz, $^3$J$_{6a7e}$=3.3 Hz, H$_a^6$), 1.85 (m, 1H, H$_e^6$), 1.94 (br.dd, 1H, $^2$J=14.6 Hz, $^3$J$_{7e6e}$=5.0 Hz, H$_e^7$), 2.11 (ddd, 1H, $^2$J=$^3$J$_{7a6a}$=14.0 Hz, $^3$J$_{7a6e}$=6.4 Hz, H$_a^7$), 2.17 (m, 2H, H$_e^9$+ Ha$^9$), 2.27 (br.dddd, 1H, $^3$J$_{5e6e}$≈$^3$J$_{5e6a}$=6.4 Hz, $^3$J$_{5e9e}$≈$^3$J$_{5e9a}$=3.2 Hz, H$_e^5$), 3.29 (d, 1H, $^2$J=14.3 Hz, H$^{12}$), 3.81 (s, 3H, MeO), 3.825 (br.dd, 1H, $^3$J$_{1e9e}$=$^3$J$_{1e9a}$=3.0 Hz, H$_e^1$), 4.24 (br.d, 1H, $^2$J=14.3 Hz, H$^{12'}$), 4.29 and 4.41 (ABq, 2H, $^2$J=10.7 Hz, CH$^{17}$H$^{17'}$O), 6.88 (ddd, 2H, $^3$J=8.7 Hz, $^4$J$_1$=$^4$J$_2$=2.0 Hz, 2H$^{m\text{-}benz.}$), 7.24 (br.d, $^3$J=8.7 Hz, 2H$^{o\text{-}benz.}$), 7.58 (dddd, 2H, $^3$J$_{15,14}$=$^3$J$_{15,16}$=7.3 Hz, $^4$J$_{1514}$=$^4$J$_{15'14}$=1.4 Hz, H$^{15,15'}$), 7.66 (dddd, 1H, $^3$J$_{16,15}$=$^3$J$_{16,15'}$=7.3 Hz, $^4$J$_{1614}$= $^4$J$_{1614'}$=1.4 Hz, H$^{16}$), 7.95 (br.d, 2H, $^3$J$_{14,15}$=7.3 Hz, H$^{14,14'}$); $^{13}$C NMR (100 MHz, CDCl$_3$, δ): 22.16 (Me$^{10}$), 22.92 (Me$^{11}$), 23.53 (C$^6$H$_2$), 24.57 (C$^9$H$_2$), 19.86 (C$^5$H), 30.76 (C$^7$H$_2$), 61.10 (C$^{12}$H$_2$), 62.91 (C$^{17}$H$_2$O), 75.94 (C$^8$), 80.84 (C$^1$H), 82.71 (C$^4$), 113.78 (2C$^{m\text{-}benz.}$H), 127.55 (2C$^{14}$H), 128.72 (2C$^{o\text{-}benz.}$H), 129.33 (2C$^{15}$H), 131.26 (C$^{1\text{-}benz.}$), 133.68 (C$^{16}$H), 141.17 (C$^{13}$), 158.92 (C$^{p\text{-}benz.}$). DCI HRMS: obsd 447.18690, calcd for C$_{24}$H$_{31}$O$_6$S (M+1) 447.18414.

EXAMPLE 28

Preparation of (1R,4R,5R,8R)-4,8-dimethyl-8-(γ,γ-dimethylallyloxy)-4-phenylsulfonylmethyl-2,3dioxabicyclo [3.3.1]nonane (35a) (Scheme 11).

To a suspension of hydroxysulfone 21a (95 mg, 0.32 mmol) in ether (1 mL) at 0° C. was added a solution of O-(γ,γ-dimethylallyl)trichloroacetimidate 45 (240 mg of ca. 96%, 1.0 mmol) in CH$_2$Cl$_2$ (0.5 mL), the mixture was stirred for 10 min to form a clear solution. A solution of TfOH in ether (0.1 mL of 0.1M TfOH solution in abs. ether, 0.01 mmol) at 0° C. was added and the green-yellow mixture was stirred for 4 h at 0° C. Subsequently additional portions of imidate 45 (240 mg, 1.0 mmol) and TfOH solution (0.1 mL, 0.01 mmol) were added and the mixture was stirred for 2 h, and then additional imidate 45 (240 mg, 1.0 mmol) and TfOH solution (0.1 mL, 0.01 mmol) were added. After being stirred for additional 2 h at 0° C. the mixture was diluted with EtOAc (15 mL) and hexane (60 mL), NaHCO$_3$ (2 g) and Na$_2$SO$_4$ (10 g) were added and the mixture was stirred overnight. The mixture was filtered, evaporated, the residue was fractionated by flash chromatography (hexane-EtOAc 84:16) and purified by MPLC (hexane-EtOAc 84:16) to give 35a (58 mg, 50.5%) as a colorless oil, R$_f$ 0.42 (hexane-EtOAc 80:20). $^1$H NMR (400 MHz, CDCl$_3$, δ): 1.29 (s, 3H, Me$^{10}$), 1.50 (br.s, 3H, Me$^{11}$), 1.65 (m, 3H, Me$^{20}$), 1.73 (m, 3H, Me$^{21}$), 1.78 (dddd, 1H, $^2$J=$^3$J$_{6a7a}$ 14.0 Hz, $^3$J$_{6a5e}$=6.0 Hz, $^3$J$_{6a7e}$=3.5 Hz, H$_a^6$), 1.82 (m, 1H, H$_e^6$), 1.85 (br.dd, 1H, $^2$J=14.0 Hz, $^3$J$_{7e6e}$=5.5 Hz, H$_e^7$), 2.06 (ddd, 1H, $^2$J≈$^3$J$_{7a6a}$= 14.0 Hz, $^3$J$_{7a6e}$=6.1 Hz, H$_a^7$), 2.10–2.18 (m, 2H, H$_e^9$+Ha$^9$), 2.27 (dddd, 1H, $^3$J$_{5e6e}$≈$^3$J$_{5e9e}$=6.0 Hz, $^3$J$_{5e6a}$≈$^3$J$_{5e9a}$=3.0 Hz, H$_e^5$), 3.27 (d, 1H, $^2$J=14.3 Hz, H$^{12}$), 3.77 (br.s, 1H, H$_e^1$), 3.80 and 3.90 (dABq, 2H, $^2$J=10.8 Hz, $^3$J$_{17,18}$=$^3$J$_{17',18}$=6.8 Hz, H$^{17}$ and H$^{17'}$), 4.22 (d.d, 1H, $^2$J=14.3 Hz, $^4$J=0.3 Hz, H$^{12'}$), 5.27 (ddqq, $^3$J$_{18,17}$=$^3$J$_{18,17'}$=6.8 Hz, $^3$J$_{18,20}$=$^3$J$_{18,20}$=1.4 Hz, HC$^{18}$ =), 7.56 (dddd, 2H, $^3$J$_{15,14}$=$^3$J$_{15,16}$=7.5 Hz, $^4$J$_{1514}$= $^4$J$_{15'14}$=1.4 Hz, H$^{15,15'}$), 7.65 (dddd, 1H, $^3$J$_{16,15}$=$^3$J$_{16,15'}$=7.5 Hz, $^4$J$_{1614}$=$^4$J$_{1614'}$=1.4 Hz, H$^{16}$), 7.94 (ddd, 2H, $^3$J$_{14,15}$=7.4 Hz, $^4$J$_{14,16}$=$^4$J$_{14'16}$=1.4 Hz, H$^{14,14'}$); $^{13}$C NMR (100 MHz, CDCl$_3$, δ): 17.94 (Me$^{20}$C=), 22.04 (Me$^{10}$), 22,87 (Me$^{11}$), 23.49 (C$^6$H$_2$), 24.48 (C$^9$H$_2$), 29.84 (C$^5$H), 30.97 (C$^7$H$_2$), 57.78 (C$^{17}$H$_2$O), 61.09 (C$^{12}$H$_2$), 75.47 (C$^8$), 80.70 (C$^1$H), 82.63 (C$^4$), 121.78 (HC$^{18}$=), 127.53 (2C$^{14}$H), 129.29 (2C$^{15}$H), 133.64 (C$^{16}$H), 135.90 (C$^{19}$=), 141.17 (C$^{13}$). DCI HRMS: obsd 395.18590, calcd for C$_{21}$H$_{31}$O$_5$S (M+1) 395.18922; obsd 377.17500, calcd for C$_{21}$H$_{29}$O$_4$S (M+1– H$_2$O) 377.17866.

EXAMPLE 29

Preparation of (1R,4R,5R,8R)-8-(trans-cinnamyloxy)-4, 8-dimethyl-4-phenylsulfonylmethyl-2,3-dioxabicyclo [3.3.1]nonane (36a) (Scheme 11).

To a suspension of hydroxysulfone 21a (113 mg, 0.345 mmol) in ether (1.2 mL) at 0° C. a solution of iminoester 46 (406 mg of ca. 97%, 1.41 mmol) in CH$_2$Cl$_2$ (0.7 mL) was added, the mixture was stirred for 10 min and a clear solution was formed. Then at 0° C. a solution of TfOH in ether (0.15 mL of 0.1M TfOH solution in abs. ether, 0.015 mmol) was added and the green-yellow mixture was stirred for 1 h at 0° C. and for 6 h at rt A second portion of iminoester 46 (406 mg, 1.41 mmol, neat) and a solution of TfOH (0.15 mL, 0.015 mmol) were added and the mixture was stirred for 12 h. A third portion of imidate 46 (406 mg, 1.41 mmol) and TfOH solution (0.15 mL, 0.015 mmol) were added and the mixture was stirred for 12 h followed by a fourth addition of TfOH solution (0.15 ml, 0.015 mmol) and stirring for additional 30 h. The mixture was diluted with hexand-EtOAc (3:1, 100 mL), NaHCO$_3$ (2 g) and Na$_2$SO$_4$ (5 g) were added. After being stirred overnight the mixture was filtered, evaporated, fractionated by flash chromatography (hexane-EtOAc, 75:25) and further purified by MPLC (hexane-EtOAc 80:20) to give 36a (49 mg, 32%) as a pale yellowish gum, R$_f$ 0.46 (hexane-EtOAc 75:25). $^1$H NMR (400 MHz, CDCl$_3$, δ): 1.34 (s, 3H, Me$^{10}$), 1.53 (br.s, 3H, Me$^{11}$), 1.84 (dddd, 1H, $^2J=^3J_{6a7a}$ 14.0 Hz, $^3J_{6a5a}$=5.6 Hz, $^3J_{6a7a}$=3.6 Hz, H$_a{}^6$), 1.84–1.93 (m, 2H, H$_e{}^6$+H$_e{}^7$), 2.10 (ddd, 1H, $^2J=^3J_{7a6a}$=14.0 Hz, $^3J_{7a6e}$=6.4 Hz, H$_a{}^7$), 2.15–2.22 (m, 2H, H$_e{}^9$+Ha$^9$), 2.27 (dddd, 1H, $^3J_{5e6e}=^3J_{5e6a}$=5.6 Hz, $^3J_{5e9e}=^3J_{5e9a}$=3.0 Hz, H$_e{}^5$), 3.29 (d, 1H, $^2J$=14.3 Hz, H$^{12}$), 3.82 (br.s, 1H, H$_e{}^1$), 3.80 and 3.90 (ddABq, 2H, $^2J$=12.6 Hz, $^3J_{17,18}=^3J_{17',18}$=5.8 Hz, $^4J_{17,19}=^4J_{17',19}$=1.5 Hz, H$^{17}$ and H$^{17'}$), 4.24 (br.d, 1H, $^2J$=14.3 Hz, H$^{'12}$), 6.25 (ddd, $^3J_{18,19}$=15.9 Hz, $^3J_{18,17}=^3J_{18,17'}$=5.8 Hz, HC$^{18}$=), 6.60 (br.d, $^3J_{19,18}$=15.9 Hz, HC$^{19}$=), 7.22–7.40 (m, 5H, PhCH=), 7.58 (m, 2H, H$^{15,15'}$), 7.66 (m, 1H, H$^{16}$), 7.96 (m, 2H, H$^{14,14'}$); $^{13}$C NMR (100 MHz, CDCl$_3$, δ): 22.11 (Me$^{10}$), 22.93 (Me$^{11}$), 23.53 (C$^6$H$_2$), 24.58 (C$_9$H$_2$), 29.90 (C$_5$H), 31.00 (C$^7$H$_2$), 61.15 (C$^{12}$H$_2$), 61.94 (C$_{17}$H$_2$O), 75.96 (C$^8$), 80.78 (C$^1$H), 82.75 (C$^4$), 126.40 (2C$^{o\text{-}phen.}$H), 127.12 (HC$^{18}$=), 127.52 (C$^{p\text{-}phen.}$H), 127.59 (2C$^{14}$H), 128.52 (2C$^{m\text{-}phen.}$H), 129.34 (2C$^{15}$H), 130.99 (HC$^{19}$=), 133.69 (C$^{1\text{-}phen.}$), 136.85 (C$^{1\text{-}phen.}$), 141.24 (C$^{13}$). DCI HRMS: obsd 443.19150, calcd for C$_{25}$H$_{31}$O$_5$S (M+1) 443:18922.

EXAMPLE 30

Preparation of (1R,4R,5R)-4,8-dimethyl-4-phenylsulfonylmethyl-2,3-dioxabicyclo[3.3.1]non-7-ene (37a) and (1R,4R,5R)-4-methyl-8-methylidene-4-phenylsulfonylmethyl-2,3-dioxabicyclo[3.3.1]nonane (38a) (Scheme 12).

To a mixture of SOCl$_2$ (395 mg, 3.32 mmol) and pyridine (656 mg, 8.30 mmol) in CH$_2$Cl$_2$ (40 mL) at 0° C. for 30 min a solution of hydroxysulfone 21a (270 mg, 0.827 mmol) in CH$_2$Cl$_2$ (15 mL) was added. The mixture was stirred at 0° C. for 2 h and for additional 4 h at rt, poured into ice-cold 0.2 N HCl (100 mL) and extracted with hexane-EtOAc (3:1, 2×200 mL). The combined organic extract was washed with saturated NaHCO$_3$ (30 mL), dried (Na$_2$SO$_4$), filtered and evaporated. Flash chromatogaphy (hexane-EtOAc, 80:20) afforded a colorless solid mixture of 37a and 38a (243 mg, 95.5%, 37a/38a ca. 86:14). More polar isomer 37a of ca. 97.5% purity was obtained by several sequential MPLC (hexane-EtOAc, 85:15) as a colorless solid, mp 111–112° C. $^1$H NMR (400 MHz, CDCl$_3$, δ): 1.47 (d, 3H, $^4J$=0.6 Hz, Me$^{11}$), 1.72 (ddd, 1H, $^2J$=13.3 Hz, $^3J_{9a5e}$=2.8 Hz, $^3$=J$_{9a1e}$=2.0 Hz, H$_a{}^9$), 1.78 (ddd, 3H, $^4J_{10,7}$=2.7 Hz, $^5J_{10,6a}\approx^5J_{10,6e}$=1.7 Hz, Me$^{10}$), 2.26 (dddq, 1H, $^2J$=19.1 Hz, $^3J_{6a7}$=5.4 Hz, $^3J_{6a5e}\approx^5J_{6a10}$=1.7 Hz, H$_a{}^6$), 2.39 (dddq, 1H, $^2J$=19.1 Hz, $^3J_{6e7}$=3.2 Hz, $^3J_{6e5e}\approx^5J_{6e10}$=1.7 Hz, H$_e{}^6$), 2.46 (m, 1H, H$_e{}^5$), 2.50 (dddd, 1H, $^2J$=13.3 Hz, $^3J_{9e5e}=^3J_{9e1e}$=3.5 Hz, $^{4\ or\ 5}J$=1.6 Hz, H$_e{}^9$), 3.29 (d, 1H, $^2J$=14.3 Hz, H$^{12}$), 4.12 (m, 1H, H$_e{}^1$), 4.31 (dd, 1H, $^2J$=14.3 Hz, $^4J$=0.6 Hz, H$^{'12}$), 5.77 (m, 1H, H$^7$), 7.58 (m, 2H, H$^{15,\ 15'}$), 7.66 (m, 1H, H$^{16}$), 7.95 (m, 2H, H$^{14,14'}$); $^{13}$C NMR (100 MHz, CDCl$_3$, δ): 21.16 (Me$^{10}$), 23.62 (Me$^{11}$), 26.83 (C$^9$H$_2$), 27.48 (C$^6$H$_2$), 29.54 (C$^5$H), 61.23 (C$^{12}$H$_2$), 76.70 (C$^1$H), 82.35 (C$^4$), 127.28 (C$^7$H), 127.55 (2C$^{14}$H), 129.35 (2C$^{15}$H), 131.15 (C$^8$=), 133.71 (C$^{16}$H), 141.20 (C$^{13}$). Anal. Calcd. for C$_{16}$H$_{20}$O$_4$S: C, 62,31; H, 6.54; S, 10.40. Found: C, 62.17; H, 6.57; S, 10.47. Less polar isomer 38a (ca. 95% purity) was isolated as a colorless semi-solid by semi-preparative DP HPLS (column—LiChrospher® Si 60 (10 μm) 250-10; eluent i-PrOH-hexane 2:98). $^1$H NMR (400 MHz, CDCl$_3$, δ): 1.57 (d, 3H, $^4J$=0.6 Hz, Me$^{11}$), 1.65 (ddd, 1H, $^2J$=13.7 Hz, $^3J_{9a5e}$=3.2 Hz, $^3J_{9a1e}$=1.7 Hz, H$_a{}^9$), 1.73 (dddd, 1H, $^2J\approx^3J_{6a7a}$=14.2 Hz, $^3J_{6a5e}$=6.4 Hz, $^3J_{6a7e}$=3.8 Hz, H$_a{}^6$), 2.15 (br.ddd, 1H, $^2J$=14.2 Hz, $^3J_{6e7e}$=6.6 Hz, $^3J_{6e5e}$=3.2 Hz, H$_e{}^6$), 2.39 (br.dd, 1H, $^2J$=14.2 Hz, $^3J_{7e6e}$=6.6 Hz, H$_e{}^7$), 2.46 (dddd, 1H, $^3J_{5e6a}\approx^3J_{5e9e}$=6.4 Hz, $^3J_{5e6e}\approx^3J_{5e9a}$=3.2 Hz, H$_e{}^5$), 2.57 (ddd, 1H, $^2J$=13.7 Hz, $^3J_{9e5e}$=6.4 Hz, $^3J_{9e1e}$=3.6 Hz, H$_e{}^9$), 2.99 (m, 1H, $^2J\approx^3J_{6a7a}$=14.2 Hz, H$_e{}^7$), 3.29 (d, 1H, $^2J$=14.3 Hz, H$^{12}$), 4.30 (br.dd, 1H, $^2J$=14.3 Hz, $^4J$=0.6 Hz, H$^{'12}$), 4.36 (br.dd, 1H, $^3J_{1e9e}$=3.6 Hz, $^3J_{1e9a}$=1.7 Hz, H$_e{}^1$), 4.92 (br.dd, 1H, $^2J\approx^4J_{10,7a}$=2.2 Hz, H$^{10}$), 4.95 (br.ddd, 1H, $^2J\approx^4J_{10',7a}$=2.2 Hz, $^4J$=0.6 Hz, H$^{'10}$), 7.59 (m, 2H, H$^{15,15'}$), 7.67 (m, 1H, H$^{16}$), 7.96 (m, 2H, H$^{14,14'}$); $^{13}$C NMR (100 MHz, CDCl$_3$, δ): 23.32 (Me$^{11}$), 27.02 (C$^6$H$_2$), 30.39 (C$^5$H), 30.50 (C$^9$H$_2$), 30.52 (C$^7$H$_2$), 61.27 (C$^{12}$H$_2$), 80.77 (C$^1$H), 82.96 (C$^4$), 113.59 (=C$^{10}$H$_2$), 127.57 (2C$^{14}$H), 129.36 (2C$^{15}$H), 131.15 (C$^8$=), 133.74 (C$^{16}$H), 141.18, (C$^{13}$), 146.21 (C$^8$). DCI HRMS obsd 309.11930, calcd for C$_{16}$H$_{21}$O$_4$S (+H) 309.11606.

EXAMPLE 31

Preparation of (1R,4R,5R,7R,8R)-7,8-epoxy-4,8-dimethyl-4-phenylsulfonylmethyl-2,3-dioxabicyclo[3.3.1] nonane (39a) (Scheme 13).

To a solution of unsaturated sulfone 37a (36.0 mg of ca. 97.5% purity, 0.114 mmol) in CH$_2$Cl$_2$ (0.5 mL) at 0° C. a suspension of MCPBA (38.0 mg of ca. 60%, 0.13 mmol) in CH$_2$Cl$_2$ (1.5 mL) was added. The mixture was stirred at rt for 12 h, diluted with hexane-EtOAc (40 mL, 3:1), washed with saturated NaHCO$_3$ (2×5 mL), the water washings were extracted with hexane-EtOAc (20 mL, 3:1). The combined organic extract was dried (Na$_2$SO$_4$+NaHCO$_3$) and evaporated. The residue was purified by flash chromatography (hexane-EtOAc, 4:1) to afford the epoxide 39a (35.5 mg. 96%) as a colorless solid, mp 130–131° C. $^1$H NMR (400 MHz, CDCl$_3$, δ): 1.44 (s, 3H, Me$^{10}$), 1.50 (d, 3H, $^4J$=0.5 Hz, Me$^{11}$), 1.91 (ddd, 1H, $^2J$=14.0 Hz, $^3J_{9a5e}$=2.3 Hz, $^3J_{9a1e}$=1.8 Hz, H$_a{}^9$), 2.01 (dd, 1H, $^2J$=16.5 Hz, $^3J_{6a5e}$=2.3 Hz, H$_a{}^6$), 2.15 (ddd, 1H, $^2J$=14.0 Hz, $^3J_{9e5e}$=6.6 Hz, $^{3J9e1e}$=3.8 Hz, H$_e{}^9$), 2.21–2.32 (m, 2H, H$_e{}^5$+H$_e{}^6$), 3.19 (br.d, 1H, $^3J_{7e6e}$=5.5 Hz, H$_e{}^7$), 3.29 (d, 1H, $^2J$=14.3 Hz, H$^{12}$), 4.18 (br.dd, 1H, $^3J_{1e9e}$=3.8 Hz, $^3J_{1e9a}$=1.8 Hz, H$_e{}^1$), 4.22 (d.d, 1H, $^2J$=14.3 Hz, $^4J$=0.5 Hz, H$^{'12}$), 7.59 (m, 2H, H$^{15,15'}$), 7.68 (m, 1H, H$^{16}$), 7.94 (m, 2H, H$^{14,14'}$); $^{13}$C NMR (63 MHz, CDCl$_3$, δ): 18.64 (Me$^{10}$), 22.57 (C$^9$H$_2$), 23.38 (Me$^{11}$), 25.27 (C$^6$H$_2$), 28.74 (C$^5$H), 57.10 (C$^8$), 59.00 (C$^7$H), 60.93 (C$^{12}$H$_2$), 78.29 (C$^1$H), 82.15 (C$^4$), 127.50 (2C$^{14}$H), 129.36 (2C$^{15}$H), 133.79 (C$^{16}$H), 140.99 (C$^{13}$). Anal. Calcd for C$_{16}$H$_{20}$O$_5$S: C, 59.74; H, 6.21; S, 9.88. Found: C, 59.54; H, 6.21; S, 9.46.

EXAMPLE 32

Preparation of 1R,4R,5R,8R)-4,8-dimethyl-4-phenylsulfinylmethyl-2,3-dioxabicyclo[3.3.1]nonan-8-ols (40a,a') and (1R,4S,5R,8R)-4,8-dimethyl-4-phenylsulfinylmethyl-2,3-dioxabicyclo[3.3.1]nonan-8-ols (40b,b') (Scheme 14).

To a solution of sulfides 2a,b (468 mg, 1.59 mmol, ratio 2a/2b ca. 55:45) in EtOAc (25 mL) at −50° C. was added a solution of MCPBA (478 mg of ca. 60%, ca. 1.65 mmol) in EtOAc (20 mL). The mixture was stirred at −30÷−40° C. for 1 h, poured into saturated NaHCO$_3$ (75 mL), extracted with EtOAc (33×60 mL), dried (Na$_2$SO$_4$+NaHCO$_3$) and evaporated. Flash chromatography on silica gel (eluent hexane-EtOAc, 1:4) afforded the mixture of diastereomeric sulfoxides 40a,a',b,b' (438 mg, total yield 89%, ratio a:a':b:b'~21:31.5:20:27.5 according to the integration in 400 MHz $^1$H NMR spectrum). The sulfoxides were separated by MPLC (hexane-EtOAc, 22:78) to obtain the individual diastereomers (listed below according the order of polarity). Isomer 40b, colorless solid, $R_f$ 0.38 (hexane-EtOAc 1:4). $^1$H NMR (400 MHz, CDCl$_3$, δ): 1.36 (s, 3H, Me$^{10}$), 1.62 (br.dd, 1H, $^2J$=13.9 Hz, $^3J_{7e6e}$=5.8 Hz, H$_e^7$), 1.79 (br.s, 3H, Me$^{11}$), 1.81 (m, 1H, H$_e^6$), 1.96 (dddd, 1H, $^2J \approx ^3J_{6a7a}$=13.9 Hz, $^3J_{6a5e}$=6.0 Hz, $^3J_{6a7e}$=3.5 Hz, H$_a^6$), 2.00 (m, 1H, H$_e^5$), 2.13 (ddd, 1H, $^2J$=13.5 Hz, $^3J_{9a5e}$=2.9 Hz, $^3J_{9a1e}$=2.0 Hz, H$_a^9$), 2.29 (ddd, 1H, $^2J \approx ^3J_{7a6a}$=13.9 Hz, $^3J_{7a6e}$=6.2 Hz, H$_a^7$), 2.35 (br.ddd, 1H, $^2J$=13.5 Hz, $^3J_{9e5e}$=6.4 Hz, $^3J_{9e1e}$=3.6 Hz, H$_e^9$), 2.77 (dd, 1H, $^2J$=13.5 Hz, $^4J$=0.6 Hz, H'$^{12}$), 2.91 (d, 1H, $^2J$=13.5 Hz, H$^{12}$), 3.73 (m, $^3J_{1e9e}$=3.6 Hz, J$_{1e9a}$=2.0 Hz, H$_e^1$), 7.50–7.56 (m, 3H, H$^{15,15'}$+H$^{16}$), 7.63–7.66 (m, 2H, H$^{14,14'}$); $^{13}$C NMR (100 MHz, CDCl$_3$, δ): 22.93 (Me$^{11}$), 23.70 (C$^6$H$_2$), 24.00 (C$^9$H$_2$), 28.04 (Me$^{10}$), 31.20 (C$^5$H), 35.47 (C$^7$H$_2$), 65.57 (C$^{12}$H$_2$), 71.32 (C$^8$), 82.20 (C$^1$H), 82.61 (C$^4$), 123.77 (2C$^{14}$H), 129.49 (2C$^{15}$H), 131.34 (C$^{16}$H), 144.73 (C$^{13}$). Isomer 40a, colorless solid, R$_f$ 0.35 (hexane-EtOAc 1:4). $^1$H NMR (250 MHz, (CDCl$_3$, δ): 1.41 (s, 3H, Me$^{10}$), 1.47 (br.s, (Me$^{10}$), 32.16 (C$^5$H), 35.46 (C$^7$H$_2$), 65.94 (C$^{12}$H$_2$), 71.38 (C$^8$), 82.35 (C$^1$H), 82.73 (C$^4$), 3H, Me$^{11}$), 1.60–1.73 (m, 1H), 1.92–2.04 (m, 2H), 2.17–2.24 (m, 3H, H$_e^5$+H$_e^7$+H$_e^9$), 2.41 (ddd, 1H, $^2J$=14.2 Hz, $^3J_{7a6a}$=12.6 Hz, $^3J_{7a6e}$=7.6 Hz, H$_a^7$), 3.13 (d, 1H, $^2J$=13.9 Hz, H$^{12}$), 3.61 (dd, 1H, $^2J$=13.9 Hz, $^4J_{12',11}$=0.4 Hz, H'$^{12}$), 3.75 (m, 1H, H$_e^1$), 7.52–7.58 (m, 3H, H$^{15,15'}$+H$^{16}$), 7.67–7.71 (m, 2H, H$^{14,14'}$). Isomer 40b', colorless solid, mp 138–140° C. (dec.), R$_f$ 0.34 (hexane-EtOAc 1:4). $^1$H NMR (250 MHz, CDCl$_3$, δ): 1.36 (s, 3H, Me$^{10}$), 1.57 (br.dd, 1H, $^2J_{7e7a}$=13.4 Hz, $^3J_{7e6e}$=5.5 Hz, H$_e^7$), 1.83 (m, 1H, H$_a^6$), 1.88–1.99 (m, 2H, H$_e^5$+H$_e^6$), 1.89 (br.s, 3H, Me$^{11}$), 2.08 (ddd, 1H, $^2J$=13.4 Hz, $^3J_{9a5e}$=2.9 Hz, $^3J_{9a1e}$=2.0 Hz, H$_a^9$), 2.17 (br.ddd, 1H, $^2J_{7a7e} \approx ^3J_{7a6a}$=14.8 Hz, $^3J_{7a6e}$=5.6 Hz, H$_a^7$), 2.35 (br.ddd, 1H, $^2J$=13.4 Hz, $^3J_{9e5e}$=6.1 Hz, $^3J_{9e1e}$=3.6 Hz, H$_e^9$), 2.72 (d, 1H, $^2J$=13.7 Hz, H$^{12}$), 3.11 (d, 1H, $^2J$=13.7 Hz, H$^{12}$), 3.75 (m, $^3J_{1e9e}$=3.6 Hz, $^3J_{1e9a}$=2.0 Hz, H$_e^1$), 7.52–7.57 (m, 3H, H$^{15,15'}$+H$^{16}$), 7.65–7.69 (m, 2H, H$^{14,14'}$); $^{13}$C NMR (63 MHz, CDCl$_3$, δ): 21.97 (Me$^{11}$), 23.48 (C$^6$H$_2$), 23.94 (C$^9$H$_2$), 28.04 123.82 (2C$^{14}$H), 129.39 (2C$^{15}$H), 131.12 (C$^{16}$H), 144.85 (C$^{13}$). Isomer 40a', a colorless solid, mp 153–155° C., R$_f$ 0.32 (hexane-EtOAc 1:4). $^1$H NMR (400 MHz, (CDCl$_3$, δ): 1.40 (s, 3H, Me$^{10}$), 1.55 (br.s, 3H, Me$^{11}$), 1.63 (br.dd, 1H, $^2J$=14.0 Hz, $^3J_{7e6e}$=5.6 Hz, H$_e^7$), 1.83 (m, 1H, H$_e^5$), 1.86 (dddd, 1H, $^2J \approx ^3J_{6a7a}$=14.0 Hz, $^3J_{6a5e}$=5.9 Hz, $^3J_{6a7e}$=3.4 Hz, H$_a^6$), 1.96 (m, 1H, $^2J \approx$14.0 Hz, H$_e^6$), 2.06 (ddd, 1H, $^2J$=13.8 Hz, $^3J_{9a5e}$=2.8 Hz, $^3J_{9a1e}$=2.0 Hz, H$_a^9$), 2.18 (ddd, 1H, $^2J$=13.8 Hz, $^3J_{9e5e}$=6.4 Hz, $^3J_{9a1e}$=3.6 Hz, H$_e^9$), 2.37 (br.ddd, 1H, $^2J \approx ^3J_{7a6a}$=14.0 Hz, $^3J_{7a6e}$=6.5 Hz, H$_a^7$), 3.31 and 3.35 (ABq, 2H, $^2J$=14.0 Hz, H$^{12}$+H'$^{12}$), 3.70 (m, 1H, $^3J_{1e9e}$=3.6 Hz, $^3J_{1e9a}$=2.0 Hz, H$_e^1$), 7.47–7.56 (m, 3H, H$^{15,15'}$+H$^{16}$), 7.64–7.69 (m, 2H, H$^{14,14'}$); $^{13}$C NMR (100 MHz, CDCl$_3$, δ): 22.08 (Me$^{11}$), 23.47 (C$^6$H$_2$), 24.37 (C$^9$H$_2$), 28.06 (Me$^{10}$), 31.56 (C$^5$H), 35.77 (C$^7$H$_2$), 66.08 (C$^{12}$H$_2$), 71.42 (C$^8$), 81.94 (C$^1$H), 82.25 (C$^4$), 123.83 (2C$^{14}$H), 129.32 (2C$^{15}$H), 130.87 (C$^{16}$H), 144.91 (C$^{13}$).

EXAMPLE 33

Preparation of (1R,4R,5R,8R)-8-acetoxy-4,8-dimethyl-4-phenylsulfinylmethyl-2,3-dioxabicyclo[3.3.1]nonanes (41a, a') and (1R,4S,5R,8R)-8-acetoxy-4,8-dimethyl-4-phenylsulfinylmethyl-2,3-dioxabicyclo[3.3.1]nonanes (41b, b') (Scheme 14).

To a solution of sulfides 13a,b (376 mg, 1.12 mmol, ratio 13a/13b ca. 55:45) in EtOAc (25 mL) at −50° C. was added a solution of MCPBA (330 mg of ca. 60%, ca. 1.15 mmol) in EtOAc (15 mL). The mixture was stirred at −30÷40° C. for 3 h, poured into saturated NaHCO$_3$ (50 mL), extracted with hexane-EtOAc (4:6, 3×60 mL), dried (Na$_2$SO$_4$+ NaHCO$_3$) and evaporated. The sulfoxides were separated by MPLC (hexane-EtOAc, 1:1), total yield 364 mg (1.02 mmol, 91%). The least polar isomer 41b, 68 mg (0.193 mmol), a colorless solid, mp 116–118° C., R$_f$ 0.41 (hexane-EtOAc 1:1). IR (neat): 2980, 2929, 1734 v.s, 1445, 1372 v.s, 1257 v.s, 1232 v.s, 1186, 1153, 1086 v.s, 1056, 1022 v.s, 933, 826, 753, 735, 694 cm$^{-1}$. $^1$H NMR (400 MHz, CDCl$_3$, δ): 1.65 (s, 3H, Me$^{10}$), 1.80 (d, 3H, $^4J$=0.65 Hz, Me$^{11}$), 1.82–1.89 (m, 2H, H$_e^6$+H$_a^6$), 1.89 (ddd, 1H, $^2J$=13.6 Hz, $^3J_{9a5e}$=3.2 Hz, $^3J_{9a1e}$=1.8 Hz, H$_a^9$), 2.02 (m, 1H, H$_e^5$), 2.03 (s, 3H, Me$^{17}$CO), 2.18–2.29 (m, 2H, H$_a^7$+H$_e^7$), 2.39 (br.ddd, 1H, $^2J$=13.6 Hz, $^3J_{9e5e}$=5.7 Hz, $^3J_{9e1e}$=3.8 Hz, H$_e^9$), 2.77 (dd, 1H, $^2J$=13.4 Hz, $^4J$=0.65 Hz, H'$^{12}$), 2.92 (d, 1H, $^2J$=13.4 Hz, H$^{12}$), 4.47 (br.dd, $^3J_{1e9e}$=3.8 Hz, J$^{1e9a}$=1.8 Hz, H$_e^1$), 7.52–7.57 (m, 3H, H$^{15,15'}$+H$^{16}$), 7.64–7.67 (m, 2H, H$^{14,14'}$); $^{13}$C NMR (100 MHz, CDCl$_3$, δ): 22.38 (Me$^{17}$CO), 22.45 (Me$^{10}$), 22.88 (Me$^{11}$), 23.52 (C$^6$H$_2$), 23.76 (C$^9$H$_2$), 30.55 (C$^5$H), 32.77 (C$^7$H$_2$), 65.45 (C$^{12}$H$_2$), 78.02 (C$^1$H), 82.50 (C$^8$), 82.57 (C$^4$), 123.69 (2C$^{14}$H), 129.45 (2C$^{15}$H), 131.33 (C$^{16}$H), 144.57 (C$^{13}$), 170.08 (C=O). Isomer 41a (78 mg, 0.221 mmol), a colorless oil, R$_f$ 0.40 (hexane-EtOAc 1:1). $^1$H NMR (400 MHz, (CDCl$_3$, δ): 1.44 (br.s, 3H, Me$^{11}$), 1.65 (s, 3H, Me$^{10}$), 1.86 (dddd, 1H, $^2J \approx ^3J_{6a7a}$=14.0 Hz, $^3J_{6a5e}$=6.0 Hz, $^3J_{6a7e}$=3.5 Hz, H$_a^6$), 1.95–2.00 (m, 1H, H$_e^6$), 1.96 (ddd, 1H, $^2J$=14.0 Hz, $^3J_{9a5e}$=4.0 Hz, $^3J_{9a1e}$=1.7 Hz, H$_a^9$), 2.01 (s, 3H, Me$^{17}$CO), 2.18–2.25 (m, 3H, H$_e^5$+H$_e^7$+H$_e^9$), 2.31 (ddd, 1H, $^2J \approx ^3J_{7a6a}$=14.0 Hz, $^3J_{7a6e}$=6.0 Hz, H$_a^7$), 3.08 (d, 1H, $^2J$=13.8 Hz, H$^{12}$), 3.61 (dd, 1H, $^2J$=13.8 Hz, $^4J_{12',11}$=0.6 Hz, H'$^{12}$), 4.52 (m, 1H, H$_e^1$), 7.50–7.58 (m, 3H, H$^{15,15'}$+H$^{16}$), 7.66–7.68 (m, 2H, H$^{14,14'}$). $^{13}$C NMR (100 MHz, CDCl$_3$, δ): 22.36 (Me$^{17}$CO), 22.43 (Me$^{10}$), 23.36 (C$^6$H$_2$), 23.55 (Me$^{11}$), 24.16 (C$^9$H$_2$), 29.09 (C$^5$H), 32.98 (C$^7$H$_2$), 64.54 (C$^{12}$H$_2$), 77.58 (C$^1$H), 82.37 (C$^8$), 82.53 (C$^4$), 123.65 (2C$^{14}$H), 129.35 (2C$^{15}$H), 131.10 (C$^{16}$H), 144.38 (C$^{13}$), 170.10 (C=O). Isomer 41b' (96 mg, 0.272 mmol), a colorless solid, mp 105–107° C., R$_f$ 0.36 (hexane-EtOAc 1:1). $^1$H NMR (400 MHz, CDCl$_3$, δ): 1.62 (s, 3H, Me$^{10}$), 1.76 (dddd, 1H, $^3J_{6a7a}$=14.2 Hz, $^2J_{6a6e}$=12.5 Hz, $^3J_{6a5e}$=7.2 Hz, $^3J_{6a7e}$=3.3 Hz, H$_a^6$), 1.83 (ddd, 1H, $^2J$=13.6 Hz, $^3J_{9a5e}$=3.3 Hz, $^3J_{9a1e}$=1.8 Hz, H$_a^9$), 1.89 (br.s, 3H, Me$^{11}$), 1.90 (m, 1H, H$_e^5$), 1.93–2.02 (m, 1H, $^2J_{6e6a} \approx$12.5 Hz, H$_e^6$), 2.02 (s, 3H, Me$^{17}$CO), 2.07 (m, 1H, $^2J_{7a7e}$=14.8 Hz, $^3J_{7a6a}$=14.2 Hz, $^3J_{7a6e}$=5.6 Hz, H$_a^7$), 2.14 (m, 1H, $^2J_{7e7a} \approx$14.8 Hz, $^3J_{7e6e} \approx$6.6 Hz, H$_e^7$), 2.35 (br.ddd, 1H, $^2J$=13.6 Hz, $^3J_{9e5e}$=6.8 Hz, $^3J_{9e1e}$=3.3 Hz, H$_e^9$), 2.67 (br.d, 1H, $^2J$=13.6 Hz, H$^{12}$), 3.10 (d, 1H, $^2J$=13.6 Hz, H'$^{12}$), 4.49 (br.d, $^3J_{1e9e}$=3.3 Hz, H$_e^1$), 7.49–7.57 (m, 3H, H$^{15,15'}$+H$^{16}$), 7.63–7.67 (m, 2H, H$^{14,14'}$); $^{13}$C NMR (100 MHz, CDCl$_3$, δ): 22.05 (Me$^{10}$), 22.47 (Me$^{17}$CO), 22.59 (Me$^{11}$), 23.46 (C$^6$H$_2$), 23.80 (C$^9$H$_2$), 31.60 (C$^5$H), 32.92 (C$^7$H$_2$), 65.82 (C$^{12}$H$_2$), 78.34 (C$^1$H), 82.64 (C$^8$), 82.81 (C$^4$), 123.81 (2C$^{14}$H), 129.42 (2C$^{15}$H), 131.16 (C$^{16}$H), 144.90 (C$^{13}$), 170.22 (C=O). The most polar isomer 41a' (122 mg, 0.346 mmol), a colorless solid, mp 98–100° C., R$_f$ 0.29 (hexane-EtOAc 1:1). $^1$H NMR (400 MHz, CDCl$_3$, δ): 1.56 (br.s, 3H, Me$^{11}$), 1.68 (s, 3H, Me$^{10}$), 1.78 (dddd, 1H, $^2J \approx ^3J_{6a7a}$=14.0 Hz, $^3J_{6a5e}$=6.0 Hz, $^3J_{6a7e}$=3.2 Hz, H$_a^6$), 1.80–1.88 (m, 2H, H$_a^5$+H$_a^9$), 1.95 (m, 1H, $^2J \approx$14.0 Hz, H$_e^6$), 2.01 (s, 3H, Me$^{17}$CO), 2.20 (br.dd, 1H, $^2J \approx$14.8 Hz, $^3J_{7e6e}$=6.2 Hz, H$_e^7$), 2.30 (ddd, 1H, $^2J$=14.8 Hz, $^3J_{7a6e}$=5.9 Hz, H$_a^7$), 3.31 and 3.355 (ABq, 2H, $^2J$=14.0 Hz, H$^{12}$+H'$^{12}$), 4.47 (br.d, $^3J_{1e9e}$=3.6 Hz, H$_e^1$), 7.48–7.57 (m, 3H, H$^{15,15'}$+H$^{16}$), 7.66–7.69 (m, 2H, H$^{14,14'}$). $^{13}$C NMR (100 MHz, CDCl$_3$, δ): 22.23 (Me$^{11}$), 22.48 (Me$^{17}$CO), 22.53

(Me$^{10}$), 23.42 (C$^6$H$_2$), 24.17 (C$^9$H$_2$), 30.90 (C$^5$H), 33.20 (C$^7$H$_2$), 66.04 (C$^{12}$H$_2$), 77.75 C$^1$H), 82.25 (C$^8$), 82.67 (C$^4$), 123.82 (2C$^{14}$H), 129.35 (2C$^{15}$H), 130.92 (C$^{16}$H), 144.86 (C$^{13}$), 170.22 (C=O).

EXAMPLE 34

Preparation of (1R,4R,5R)-4,8-dimethyl-4-phenylsulfinylmethyl-2,3-dioxabicyclo[3.3.1]non-7-enes (42a,a'), (1R,4S,5R)-4,8-dimethyl-4-phenylsulfinylmethyl-2,3-dioxabicyclo[3.3.1]non-7-enes (42b,b'), (1R,4R,5R)-4-methyl-8-methylidene-4-phenylsulfinylmethyl-2,3-dioxabicyclo[3.3.1]nonanes (43a,a') and (1R,4S,5R)-4-methyl-8-methylidene-4-phenylsulfinylmethyl-2,3-dioxabicyclo[3.3.1]nonanes (43b,b') (Scheme 15).

To a solution of sulfides 9a,b and 10a,b (138 mg, 0.50 mmol) in EtOAc (10 mL) at −30÷−35° C. was added a solution of MCPBA (128 mg of ca. 70%, ca. 0.52 mmol) in EtOAc (8 mL). The mixture was stirred at −30÷−40° C. for 1 h, poured into saturated NaHCO$_3$ (50 mL), extracted with EtOAc (3×30 mL), dried (Na$_2$SO$_4$+NaHCO$_3$) and evaporated. The mixture of eight sulfoxides was fractionated by MPLC (hexane-EtOAc, from 1:4 to 1:1) to give 3 fractions of sulfoxides, total yield 135 mg (0.462 mmol, 92.3%). (i) The least polar fraction, separated 18 mg (total 0.061 mmol), a colorless solid, mp 136–139° C., R$_f$ 0.49 (hexane-EtOAc 1:1), consisted of 42b and 43b (42b/43b ca. 85:15). $^1$H NMR (400 MHz, CDCl$_3$, δ): 1.625 (ddd, $^2$J=13.4 Hz, $^3$J$_{9a5e}$=3.1 Hz, $^3$J$_{9a1e}$=1.9 Hz, H$_a^9$ 42b) and 1.70 (ddd, $^2$J=13.1 Hz, $^3$J$_{9a5e}$=3.0 Hz, $^3$J$_{9a1e}$=2.2 Hz, H$_a^9$ 43b), total 1H; 1.79 (br.dd, ca. 2.5H, $^4$J$_{10,7}$=2.8 Hz, $^5$J$_{10,6e}$=2.0 Hz, Me$^{10}$ 42b); 1.810 (br.d, $^4$J=0.55 Hz, Me$^{11}$ 43b), 1.816 (br.d, $^4$J=0.65 Hz, Me$^{11}$ 42b), total 3H; 2.08 (m, ca. 0.15H, H$_e^6$ 43b); 2.16 (m, H$_e^5$ 43b) and 2.19 (m, H$_e^5$ 42b), total 1H; 2.27–2.42 (m, total ca. 2.3H); 2.60 (dddd, ca. 0.85H, $^2$J=13.2 Hz, $^3$J$_{9e5e}$=$^3$J$_{9e1e}$=3.5 Hz, $^4$J$_{9e6e}$=1.2 Hz, H$_e^9$ 42b); 2.67 (m, ca. 0.15H, H$^7$ 43b); 2.77 (dd, $^2$J=13.5 Hz, $^4$J=0.65 Hz, H'$^{12}$ 42b) and 2.855 (dd, $^2$J=13.4 Hz, $^4$J=0.55 Hz, H'$^{12}$ 43b), total 1H; 2.88 (d, $^2$J=13.5 Hz, H$^{12}$ 42b) and 2.97 (d, $^2$J=13.4 Hz, H$^{12}$ 43b), total 1H; 4.17 (br.dd, $^3$J$_{1e9e}$=3.5 Hz, $^3$J$_{1e9a}$=1.9 Hz, H$_e^1$ 42b) and 4.44 (br.dd, $^3$J$_{1e9e}$=3.5 Hz, $^3$J$_{1e9a}$=1.5 Hz, H$_e^1$ 43b), total 1H; 4.930 (br.s, H$^{10}$ 43b) and 4.936 (br.s, H'$^{10}$ 43b), total ca. 0.3H; 5.73 (m, ca. 0.85H, H$^7$ 42b); 7.47–7.56 (m, total 3H, H$^{15,15'}$+H$^{16}$), 7.62–7.68 (m, total 2H, H$^{14,14'}$); $^{13}$C NMR (100 MHz, CDCl$_3$, δ): 21.15 (Me$^{10}$ 42b), 23.17 (Me$^{11}$ 43b), 43b), 26.29 (C$^9$H$_2$ 42b), 27.20 (C$^6$H$_2$ 43b), 27.94 (C$^6$H$_2$ 42b), 29.80 (C$^9$H$_2$ 42b), 30.28 (C$^7$H$_2$ 43b), 30.35 (C$^5$H 42b), 31.58 (C$^5$H 43b), 65.47 (C$^{12}$H$_2$ 43b), 65.50 (C$^{12}$H$_2$ 42b), 76.83 (C$^1$H 42b), 80.77 (C$^1$H 43b), 82.19 (C$^4$ 42b), 113.31 (=C$^{10}$H$_2$ 43b), 123.74 (2C$^{14}$H) 42b), 123.80 (2C$^{14}$H 43b), 126.00 (=C$^7$H 42b), 129.44 (2C$^{15}$H 42b), 129.51 (2C$^{15}$H 43b), 131.29 (C$^{16}$H 42b), 131.35 (C$^{16}$H 43b), 131.80 (C$^8$= 42b), 144.68 (C$^{13}$ 42b), 146.1 (C$^{13}$ 43b). The following fraction, separated 61 mg (total 0.209 mmol), colorless oil, R$_f$ 0.43 (hexane-EtOAc 1:1). The fraction consisted of 42a, 43a, 42b' and 43b' (42/43 ca. 94: 6; 42a/42b' ca. 55:45). $^1$H NMR (400 MHz, CDCl$_3$, δ): 1.39 (br.d, $^4$J=0.7 Hz, Me$^{11}$ 42a); 1.875 (br.s, Me$^{11}$ 43b'), 1.895 (br.s, Me$^{11}$ 42b'), total 3H; 1.56 (m, H$_a^9$ 43b'), 1.63 (ddd, $^2$J=13.1 Hz, $^3$J$_{9a5e}$=3.2 Hz, $^3$J$_{9a1e}$=2.1 Hz, H$_a^9$ 42b') and 1.75 (ddd, $^2$J=13.4 Hz, $^3$J$_{9a5e}$≈$^3$J$_{9a1e}$=2.4 Hz, H$_a^9$ 42a), total ca. 1H; 1.765 (m, Me$^{10}$ 42b') and 1.79 (m, Me$^{10}$ 42a), total ca. 3H; 1.99 (m, ca. 0.5H, H$_e^5$ 42a); 2.20 (m, ca. 0.5H, H$_a^6$ 42a), 2.26–2.34 (m, total ca. 1H, H$_e^5$+H$_a^6$ 42b'); 2.36–2.48 (m, total ca. 2H); 2.53–2.59 (m, total ca. 0.5H, H$_e^9$ 42b',43b'); 2.55 (d, $^2$J=13.8 Hz, H$^{12}$ 42b') and 3.13 (d, $^2$J=13.9 Hz, H$^{12}$ 42a), total 1H; 3.08 (br.d, $^2$J=13.8 Hz, H'$^{12}$ 42b'), 3.13 (br.d, $^2$J=13.8 Hz, H'$^{12}$ 43b') and 3.66 (dd, $^2$J=13.9 Hz, $^4$J=0.7 Hz, H'$^{12}$ 42a), total 1H; 4.15 (m, H$_e^1$ 42a, 42b') and 4.43 (br.d, H$_e^1$ 43a, 43b'), total 1H; 4.895 (br.s, H$^{10}$ 43a,b') and 4.90 (br.s, H'$^{10}$ 43a,b'), total ca. 0.12H; 5.68 (m, H$^7$ 42b') and 5.78 (m, H$^7$ 42a), total ca. 0.95H; 7.46–7.56 (m, total 3H, H$^{15,15'}$+H$^{16}$), 7.61–7.68 (m, total 2H, H$^{14,14'}$); $^{13}$C NMR (100 MHz, CDCl$_3$, δ): 21.08 (Me$^{10}$ 42a, 42b'), 21.87 (Me$^{11}$ 42b'), 22.10 (Me$^{11}$ 43b'), 24.09 (Me$^{11}$ 42a), 26.20 (C$^9$H$_2$ 42b'), 26.50 (C$^9$H$_2$ 42a) 27.38 (C$^6$H$_2$ 42a), 27.78 (C$^6$H$_2$ 42b'), 29.21 (C$^5$H 42b'), 31.53 (C$^5$H 42a), 64.83 (C$^{12}$H$_2$ 42a), 66.19 (C$^{12}$H$_2$ 42b'), 76.42 (C$^1$H 42a), 77.05 (C$^1$H 42b'), 80.94 (C$^1$H 43a,b'), 81.94 (C$^4$ 42a), 82.11 (C$^4$ 42b'), 113.10 (=C$^{10}$H$_2$ 43a,b'), 123.72 (2C$^{14}$H 42a), 123.76 (2C$^{14}$H 42b'), 126.60 (=C$^7$H 42b'), 126.93 (=C$^7$H 42a), 129.29 (2C$^{15}$H 42b'), 129.34 (2C$^{15}$H 42a), 130.99 (C$^8$=42b'), 131.01 (C$^{16}$H 42b'), 131.06 (C$^{16}$H 42a), 131.09 (C$^8$=42a), 144.60 (C$^{13}$ 42a), 144.77 (C$^{13}$ 42b'), 146.28 (C$^{13}$ 43a,b'). The most polar fraction, 56 mg (total 0.192 mmol), a colorless oil, R$_f$ 0.35 (hexane-EtOAc 1:1). The fraction consisted of 42a' and 43a' (42a'/43a'ca. 91:9). The isomers 42a' and 43a' were separated by additional MPLC (hexane-EtOAc 2:3) of the last fraction. Less polar isomer 43a' (ca. 95% purity) was isolated as a colorless waxy solid, mp 78–82° C. $^1$H NMR (400 MHz, CDCl$_3$, δ): 1.58 (m, 1H, H$_a^9$), 1.61 (br.s, 3H, Me$^{11}$), 1.72 (dddd, 1H, $^2$J=$^3$J$_{6a7a}$=13.8 Hz, $^3$J$_{6a5e}$=6.4 Hz, $^3$J$_{6a7e}$=3.7 Hz, H$_a^6$), 2.04 (dddd, 1H, $^3$J$_{5e6a}$=$^3$J$_{5e9e}$=6.4 Hz, $^3$J$_{5e6e}$=$^3$J$_{5e9a}$=3.2 Hz, H$_e^5$), 2.18 (m, 1H, $^2$J=13.8 Hz, H$_e^6$), 2.41 (br.dd, 1H, $^2$J=15.2 Hz, $^3$J$_{7e6e}$=6.0 Hz, H$_e^7$), 2.51 (br.ddd, 1H, $^2$J=13.6 Hz, $^3$J$_{9e5e}$=6.4 Hz, $^3$J$_{9e1e}$=3.5 Hz, H$_e^9$), 3.06 (m, 1H, H$_a^7$), 3.28 (br.d, 1H, $^2$J=14.0 Hz, H$^{12}$), 3.50 (br.d, 1H, $^2$J=14.0 Hz, H'$^{12}$), 4.37 (br.dd, 1H, $^3$J$_{1e9e}$=3.5 Hz, $^3$J$_{1e9a}$=1.5 Hz, H$_e^1$), 4.93 (br.dd, 1H, $^2$J=$^4$J$_{10,7a}$=2.2 Hz, H$^{10}$), 4.96 (m, 1H, H'$^{10}$), 7.52 (m, 1H, H$^{16}$), 7.55 (m, 2H, H$^{15,15'}$), 7.69 (m, 2H, H$^{14, 14'}$); $^{13}$C NMR (100 MHz, CDCl$_3$, δ): 22.48 (Me$^{11}$), 27.00 (C$^6$H$_2$), 30.05 (C$^9$H$_2$), 30.47 (C$^7$H$_2$), 31.69 (C$^5$H), 66.24 (C$^{12}$H$_2$), 80.61 (C$^1$H), 82.49 (C$^4$), 113.64 (=C$^{10}$H$_2$), 123.85 (2C$^{14}$H), 129.33 (2C$^{15}$H), 130.91 (C$^{16}$H), 146.22 (C$^{13}$), 154.64 (C$^8$). More polar isomer 42a', a colorless solid, mp 90–92° C. $^1$H NMR (400 MHz, CDCl$_3$, δ): 1.51(br.s, 3H, Me$^{11}$), 1.64 (ddd, 1H, $^2$J=13.3 Hz, $^3$J$_{9a5e}$=3.0 Hz, $^3$J$_{9a1e}$=2.2 Hz, H$_a^9$), 1.79 (ddd, 3H, $^4$J$_{10,7}$=2.7 Hz, $^5$J$_{10,6a}$=$^5$J$_{10,6e}$=1.6 Hz, Me$^{10}$), 1.99 (m, 1H, H$_e^5$), 2.23 (dddq, 1H, $^2$J=19.2 Hz, $^3$J$_{6a7}$=5.4 Hz, $^3$J$_{6a5e}$=$^5$J$_{6a10}$=1.6 Hz, H$_a^6$), 2.37–2.47 (m, 2H, H$_e^6$+H$_e^9$), 3.30 (d, 1H, $^2$J=14.0 Hz, H$^{12}$), 3.44 (dd, 1H, $^2$J=14.0 Hz, $^4$J=0.35 Hz, H'$^{12}$), 4.12 (m, 1H, $^3$J$_{1e9a}$=$^3$J$_{1e9a}$=2.2 Hz, H$_e^1$), 5.78 (m, 1H, H$^7$), 7.50 (m, 1H, H$^{16}$), 7.53 (m, 2H, H$^{15, 15'}$), 7.68 (m, 2H, H$^{14, 14'}$); $^{13}$C NMR (100 MHz, CDCl$_3$, δ): 21.10 (Me$^{10}$), 22.70 (Me$^{11}$), 26.47 (C$^9$H$_2$), 27.35 (C$^6$H$_2$), 30.95 (C$^5$H), 66.09 (C$^{12}$H$_2$), 76.54 (C$^1$H), 81.77 (C$^4$), 123.79 (2C$^{14}$H), 126.98 (C$^7$H), 129.27 (2C$^{15}$H), 130.82 (C$^{16}$H), 131.56 (C$^8$=), 144.93 (C$^{13}$).

EXAMPLE 35

Determination of in vitro antimalarial activity of the compounds A.

the protozoan *Plasmodium falciparum* is a causative agent of malaria. The antimalarial activity of 2,3-dioxabicyclo [3.3.1]nonanes of type A was determined by measuring the incorporation of [$^3$H]hypoxanthine, by the methods of Desjardins[9] and Milhous,[10] into chloroquinone-sensitive *Plasmodium falciparum* (NF54)[11] in the presence of varying drug concentrations. Dose-response response curves that were fit to the experimental data by means of the Marquardt algorithm[12] were solved for the drug concentration that kills 50% of parasites (IC$_{50}$), and were analyzed for accuracy of fit (R$^2$ value, typically ≧0.99). Provisional IC$_{50}$ values were obtained in a survey of seven 5-fold dilutions (in triplicate) of stock solutions of chromatographically-purified or recrystalized test compound. Assay were later expanded to include ten concentrations (in quadruplicate) of ~1.8-fold dilutions, which flank the provisional $IC_{50}$.

Tables 1–3 present tabulations of a number of compounds that have been synthesized along with the $IC_{50}$ (in nM).

TABLE 1

In vitro antimalarial activity of (1R, 5R)-2,3-dioxabicyclo[3.3.1]nonanes against chloroquine-sensitive *P. falciparum* (NF 54)

| Compound No. | Absolute Configuration | M | Y | Z | $IC_{50}$ (nM) |
|---|---|---|---|---|---|
| 21a | 1R, 4R, 5R, 8R | OH | $PhSO_2$ | H | 55[e] |
| 21b | 1R, 4S, 5R, 8R | OH | H | $PhSO_2$ | 89[e] |
| 40a' | 1R, 4R, 5R, 8R | OH | PhSO | H | 150[e] |
| 23a | 1R, 4R, 5R, 8R | OAc | $PhSO_2$ | H | 17[e] |
| 23b | 1R, 4S, 5R, 8R | OAc | H | $PhSO_2$ | 17[e] |
| 41a | 1R, 4R, 5R, 8R | OAc | PhSO | H | 40[e] |
| 41a' | 1R, 4R, 5R, 8R | OAc | PhSO | H | 14[e] |
| 41b | 1R, 4S, 5R, 8R | OAc | H | PhSO | 71[e] |
| 24a | 1R, 4R, 5R, 8R | $OCO)CH_2Ac$ | $PhSO_2$ | H | 46[e] |
| 24b | 1R, 4S, 5R, 8R | $OC(O)CH_2Ac$ | H | $PhSO_2$ | 73[e] |
| 25a | 1R, 4R, SR, 8R | $OC(O)C(O)OEt$ | $PhSO_2$ | H | 170[e] |
| 25b | 1R, 4S, 5R, 8R | $OC(O)C(O)OEt$ | H | $PhSO_2$ | 140[e] |
| 26a | 1R, 4R, 5R, 8R | $OC(O)C(O)NBn_2$ | $PhSO_2$ | H | 21[3] |
| 26b | 1R, 4S, 5R, 8R | $OC(O)C(O)NBn_2$ | H | $PhSO_2$ | 81[e] |
| 27a | 1R, 4R, 5R, 8R | $OC(O)OPh$ | $PhSO_2$ | H | 47[e] |
| 27b | 1R, 4S, 5R, 8R | $OC(O)OPh$ | H | $PhSO_2$ | 150[e] |
| 34a | 1R, 4R, 5R, 8R | $OCH_2C_6H_4OMe$-p | $PhSO_2$ | H | 14[e] |
| 35a | 1R, 4R 5R, 8R | $OCH_2CH=CMe_2$ | $PhSO_2$ | H | 35[e] |
| 36a | 1R, 4R, 5R, 8R | $OCH_2CH=CHPh$-trans | $PhSO_2$ | H | 32[e] |
| 22a | 1R, 4R, 5R, 8S | H | $PhSO_2$ | H | 17[e] |
| 22b | 1R, 4S, 5R, 8S | H | H | $PhSO_2$ | 24[e] |

Notes:
[e]Expansion data.

TABLE 2

In vitro antimalarial activity of (1S, 5S)-2,3-dioxabicyclo[3.3.1] nonanes against chloroquine-sensitive *P. falciparum* (NF 54)

| Compound No. | Absolute configuration | Y | Z | $IC_{50}$ (nM) |
|---|---|---|---|---|
| 4a | 1S, 4S, 5S, 7S, 8S | PhS | H | 110[s] |
| 29a | 1S, 4S, 5S, 7S, 8S | $PhSO_2$ | H | 250[s] |
| 30a | 1S, 4S, 5S, 7S, 8S | n-$BuSO_2$ | H | 300[s] |

TABLE 2-continued

In vitro antimalarial activity of (1S, 5S)-2,3-dioxabicyclo[3.3.1] nonanes against chloroquine-sensitive *P. falciparum* (NF 54)

| Compound No. | Absolute configuration | Y | Z | $IC_{50}$ (nM) |
|---|---|---|---|---|

Notes:
[s]Survey data.

TABLE 3

In vitro antimalarial activity of unsaturated and 7,8-epoxy2,3-dioxabicyclo[3.3.1]nonanes against chloroquine-sensitive *P. falciparum* (NF 54)

| 37a Y = PhSO$_2$ | 43a' | 39a |
| 42a' Y = PhSO | | |

| Compound No. | Absolute configuration | IC$_{50}$ (nM) |
| --- | --- | --- |
| 37a | 1R, 4R, 5R | 490[s] |
| 42a' | 1R, 4R, 5R | 350[e] |
| 43a' | 1R, 4R, 5R | 340[e] |
| 39a | 1R, 4R, 5R, 7R, 8R | 92[e] |

Notes:
[e]Expansion data.
[s]Survey data.

The results summarized in Tables 1–3 indicate that several of these compounds exhibit in vitro antimalarial activity of the same order of magnitude as that recorded under the same conditions for artemisin (IC$_{50}$=11 nM).[13]

EXAMPLE 36

Determination of in vivo antimalarial activity of the 2,3-dioxabicyclo[3.3.1]nonanes of formula A Based on the in vitro antimalarial activity of compounds of type A, the in vivo antimalarial activity of two representatives, namely of compounds 23a and 34a, were tested. The results are described in Table 4.

TABLE 4

In vivo antimalarial activity of (1R, 4R, 5R, 8R)-2,3-dioxabicyclo[3.3.1]nonanes 23a and 34a against chloroquine-sensitive parasites *Plasmodium berghei* (N strain) and chloquine-resistant parasites *Plasmodium yoelii* (ssp. NS) in mg/kg).*

| Compound | | P. berghei (N strain) | | P. yoelii (ssp. NS) | |
| --- | --- | --- | --- | --- | --- |
| No. | M | ED$_{50}$ | ED$_{90}$ | ED$_{50}$ | ED$_{90}$ |
| 23a | OAc | 3.7 | 7.3 | 12.5 | 28.0 |
| 34a | OPMB | 1.3 | 2.3 | 4.8 | 8.3 |

*ED$_{50}$ and ED$_{90}$ are given as the daily dose in mg/Kg, repeated every 4 days. Substances were administered to mice subcutaneously and tested by the four-day test.[14,15]

In vivo antimalarial activity of compounds 23a and 34a is similar to that of artemisinin (ED$_{50}$=0.95; and ED$_{90}$=2.5 against *P. bergheri* and ED$_{50}$=5.8; and ED$_{90}$=10.0 against *P. yoclii*)[15] and of arteflene (ED$_{50}$=2.7; and ED$_{90}$=3.9 against *P. berghei*).[16]

REFERENCES (1) TDR *News* (News from the WHO Division of Control of Tropical Diseases), 1994, 46, 5.

(2) Cumming, J. N.; Ploypradith, P.; Posner, G. H. *Advances in Pharmacology* 1997, 37, 253.

(3) Ong, H. H.; Allen, R. C. *Ann. Rep. Med. Chem.* 1988, 23, 325.

(4) Tang, W.; Eisenbrand, G. In "Chinese Drugs of Plant Origin. Chmistry, Pharmacology, and use of Traditional and Modern Medicine" Springer-Verlag: Berlin, 1992; pp 159–174.

(5) Hofheinz, W.; Schmid, G.; Stohler, H. Eur. Pat. Appl. 311955, 1989; C. A. 112, 1990, 20999.

(6) Hofheinz, W.; Burgin, H.; Gocke, E.; Jaquet, C.; Masciadri, R.; Schmid, G.; Stohler, H.; Urwyler, H. *Trop. Med. Parasitol.* 1994, 45, 261.

(7) Jaquet, C.; Stohler, H. R.; Chollet, J.; Peters, W. *Trop. Med. Parasitol.* 1994, 45, 266.

(8) Kamchonwongpaisan, S.; McKeever, P.; Hossler, P.; Ziffer, H.; Meshnick, S. R. *Am. J. Trop. Med. Hyg.*, 1997, 56,7.

(9) Dejardins, R. E.; Canfield, C. J.; Haynes, J. D.; Chulay, J. D. *Antimicrob. Agents Chemother,* 1979, 16, 710.

(10) Milhous, W. K.; Weatherly, N. F.; Bowdre, J. H.; Desjardins, R. *Antimicrob. Agents Chemother,* 1985,27, 525.

(11) Ponnudurai, T.; Leeuwenberg, A. D. E. M.; Meuwissen, J. H. E. T. *Trop Georgr. Med.* 1981, 33, 50.

(12) Bard, Y. *Nonlinear Parameter Estimation;* Academic Press; New York, 1974, p.94.

(13) Posner, G. H.; Park, S. B.; González, L.; Wang, D.; Cumming, J. N.; Klinedinst, D.; Shapiro, T. A.; Bachi, M. D. *J. Am. Chem. Soc.* 1996, 118, 3537.

(14) Peters, W.; Robinson, B. L.; Rossier, J. C.; Jefford C. W. *Ann. Trop. Med. Parasitol,* 1993, 87, 1.

(15) Jefford, C. W.; Kohmoto, S.; Jaggi, D.; Timari, G.; Rossier, J. -C.; Rudaz, M. Barbuzzi, O.; Gerard, D.; Burger, U.; Kamalaprija, P.; Mareda, J.; Bernardinelli, G.; Manzanares, I.; Canfield, C. J.; Fleck, S. L.; Robinson, B. L.; Peters, W. *Helv. Chim Acta,* 1995, 78, 647.

(16) Jaquet, C.; Stohler, R. H.; Chollet, J.; Peters, W. *Trop Med. Parasitol.* 1994, 45, 266.

What is claimed is:

1. A 2,3-dioxabicyclo[3.3.1]nonane derivative, carrying, at position 4, a sulfur-containing functionality selected from the group consisting of sulfonyl, sulfinyl and sulfenyl, adhered to C(4) via methylene group, repreesented by the general structural formula A.

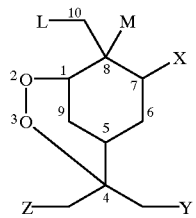

A wherein

X is hydrogen; hydroxy; alkoxy, optionally substituted by alkoxy or acyloxy; aralkoxy or acyloxy optionally substituted by alkoxy or aryloxy; and M is hydrogen; hydroxy; alkoxy; alkenyloxy; acyloxy optionally substituted by acyl or acyloxy; aralkoxy; arylalkenyloxy; oxalyloxy substituted by alkoxy, di(alkyl)amino or alkyl(aryl)amino; di(aralalkyl)amino or carbonyloxy substituted by aryloxy, di(alkyl)amino. di(aralkyl)amino and alkyl(aryl)amino; or X and M together represent a carbon-carbon bond or an oxygen atom;

L is hydrogen or L and M together represent a carbon-carbon bond; and either Z is a radical R—S($=$O)$_n$-and Y is hydrogen, or Y is R—S($=$O)$_n$-and Z is hydrogen, wherein R is alkyl optionally substituted by alkoxy or alkoxycarbonyl; cycloalkyl; or aryl or aralkyl optionally substituted by alkyl, halogen or $CF_3$; and n is 0, 1 or 2.

2. A compound according to claim 1 wherein R is a radical selected from: n-buty; tert-butyl; cyclohexyl; 3-octyl; n-dodecyl; octyloxyethyl; ethoxy-carbonylmethyl; phenyl; biphenyl; 4-fluorophenyl; 2,4-dichlorophenyl; 2,4-difluorophenyl; 2-naphthyl; benzyl; 4-phenylbutyl; 4'-(trifluoromethyl)-benzyl; (triphenyl)methyl; 4-methylphenyl; 4-(trifluoromethyl)phenyl; 2,4-dimethylphenyl; 2,4-phenyl; 3,5-phenyl.

3. A compound according to claim 1 wherein X is selected from: methoxy; hexyloxy; dodecyloxy; (butoxy)ethoxy; acetyloxy; benzoyloxy; diphenylacetyloxy; (hexanoyloxy) ethoxy; butanoyloxy; octanoyloxy; dodecanoyloxy; phenethyloxy; methoxyacetyloxy; phenoxyaceyloxy; biphenyl-4-carbonoyloxy.

4. A compound according to claim 1 wherein M is selected from: methoxy; octyloxy; allyloxy; 3-(methyl)but-2-enyloxy; 4-(methoxy)benzyloxy; cinnamyloxy; acetyloxy; acetylacetyloxy; 3-(acetyloxy)but-2-enoyloxy; ethoxy-oxalyloxy; (methyl)phenylaminooxalyloxy; di(benzyl)aminooxalyloxy; phenoxycarbonyloxy.

5. A compound according to claim 1 of structure I characterized by stereogenic centers (1R, 5R) of the formula:

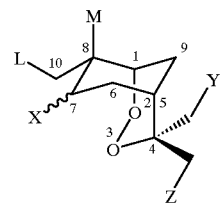

I wherein L, M, X, Y and Z are as defined in claim 1.

6. A compound according to claim 1 of structure II characterized by stereogenic centers (1S, 5S) of the formula:

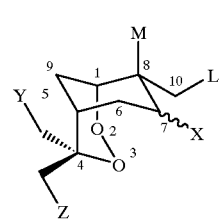

II wherein L, M, X, Y and Z are as defined in claim 1.

7. A compound according to claim 5 of structure Ia characterized by stereogenic centers (4R) of the formula:

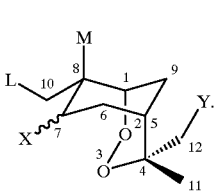

Ia

8. A compound according to claim 5 of structure Ib characterized by stereogenic centers (4S) of the formula:

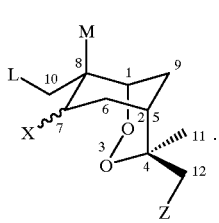

Ib

9. A compound according to claim 6 of structure IIA characterized by stereogenic centers (4S) of the formula:

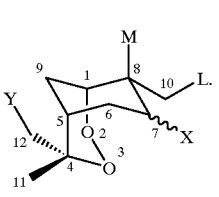

IIa

10. A compound according to claim 6 of structure IIb characterized by stereogenic centers (4R) of the formula:

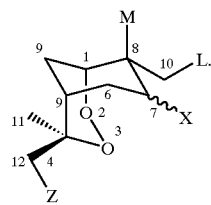

11. A compound according to claim 1 selected from (1R,4R,5R,8R)-4,8-dimethyl-4-phenylsulfonylmethyl-2,3-dioxabicyclo [3.3.1]nonan-8-ol (21a); (1R,4R,5R,8S)-4,8-dimethyl-4-phenylsulfonylmethyl-2,3-dioxabicyclo [3.3.1] nonane (22a); (1R,4S,5R,8S)-4,8-dimethyl-4-phenylsulfonylmethyl-2,3-dioxabicyclo[3.3.1]nonane (22b); (1R,4R,5R,8R)-8-acetoxy-4,8-dimethyl-4-phenylsulfonylmethyl-2,3-dioxabicyclo [3.3.1]nonane (23a); (1R,4S,5R,8R)-8-acetoxy-4,8-dimethyl-4-phenylsulfonylmethyl-2,3-dioxabicyclo[3.3.1]nonane (23b); (1R,4R,5R,8R)-8-acetylacetoxy-4,8-dimethyl-4-phenylsulfonylmethyl-2,3-dioxabicyclo[3.3.1]nonane (24a); (1R,4R,5R,8R)-8-dibenzylaminooxalyloxy-4,8-dimethyl-4-phenylsulfonylmethyl-2,3-dioxabicyclo[3.3.1]nonane (26a); (1R,4R,5R,8R)-4,8-dimethyl-8-phenoxycarbonyloxy-4-phenylsulfonylmethyl-2,3-dioxabicyclo[3.3.1]nonane (27a); (1R,4R,5R,8R)-4,8-dimethyl-8-phenoxy-acetoxy-4-phenylsulfonylmethyl-2,3-dioxabicyclo[3.3.1]nonane (33a); (1R,4R,5R,8R)-4,8-dimethyl-8-(p-methoxybenzyloxy)-4-phenylsulfonyl-methyl-2,3-dioxabicyclo[3.3.1]nonane (34a); (1R,4R,5R,8R)-4,8-dimethyl-8-(γ,γ-dimethylallyloxy)-4-phenylsulfonylmethyl-2,3-dioxabicyclo [3.3.1]nonane (35a); (1R,4R,5R,8R)-8-(trans-cinnamyloxy)-4,8-dimethyl-4-phenylsulfonylmethyl-2,3-dioxabicyclo [3.3.1]nonane (36a); (1R,4R,5R,8R)-8-acetoxy-4,8-dimethyl-4-phenylsulfinylmethyl-2,3-dioxabicyclo[3.3.1]nonanes (41a, a'); (1R,4S,5R,8R)-8-acetoxy-4,8-dimethyl-4-phenylsulfinylmethyl-2,3-dioxabicyclo[3.3.1]nonane (41b').

12. A pharmaceutical composition for the prevention and/or treatment of malaria comprising a compound of formula A in claim 1, and a pharmaceutically acceptable carrier.

\* \* \* \* \*